United States Patent [19]
Ciccarone et al.

[11] Patent Number: 5,977,134
[45] Date of Patent: *Nov. 2, 1999

[54] INHIBITORS OF FARNESYL-PROTEIN TRANSFERASE

[75] Inventors: Terrence M. Ciccarone, Telford; Wasyl Halczenko, Lansdale; John H. Hutchinson, Philadelphia; William C. Lumma, Jr., Pennsburg; Gerald E. Stokker, Gwynedd Valley; Craig A. Stump, Schwenksville; Theresa M. Williams, Harleysville, all of Pa.

[73] Assignee: Merck & Co., Inc., Rahway, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/985,320

[22] Filed: Dec. 4, 1997

Related U.S. Application Data

[60] Provisional application No. 60/032,579, Dec. 5, 1996.
[51] Int. Cl.$^6$ .......................... C07D 401/02; A61K 31/47; A61K 31/415
[52] U.S. Cl. .......................... 514/307; 514/314; 514/339; 514/394; 514/397; 546/139; 546/146; 546/148; 546/149; 546/152; 546/273.4; 546/277.1; 548/304.7; 548/335.5
[58] Field of Search ...................................... 546/118, 130, 546/152, 146, 148, 277.1, 273.4, 149; 548/304.7, 454, 335.5; 514/303, 307, 314, 393, 394, 414, 339, 397

[56] References Cited

U.S. PATENT DOCUMENTS

| | | | |
|---|---|---|---|
| 5,141,851 | 8/1992 | Brown et al. | 435/15 |
| 5,238,922 | 8/1993 | Graham et al. | 514/18 |
| 5,340,828 | 8/1994 | Graham et al. | 514/357 |
| 5,352,705 | 10/1994 | Deana et al. | 514/630 |
| 5,439,918 | 8/1995 | de Solms et al. | 514/307 |
| 5,504,212 | 4/1996 | De Solms et al. | 546/336 |
| 5,569,768 | 10/1996 | Boyd et al. | 548/253 |
| 5,571,835 | 11/1996 | Anthony et al. | 514/428 |

FOREIGN PATENT DOCUMENTS

| | | |
|---|---|---|
| 0 618 221 A2 | 10/1994 | European Pat. Off. . |
| 0 675 112 A1 | 10/1995 | European Pat. Off. . |
| 0 696 593 A2 | 2/1996 | European Pat. Off. . |
| 96/00736 | 1/1996 | WIPO . |
| 96/24612 | 8/1996 | WIPO . |
| 97/18813 | 5/1997 | WIPO . |
| 97/30053 | 8/1997 | WIPO . |

OTHER PUBLICATIONS

Gibbs, J.B. et al., "Selective Inhibition of Farnesyl–Protein Transferase Blocks Ras Processing in Vivo," The Journal of Biological Chemistry, vol. 268, No. 11, pp. 7617–7620 (1993).

Goldstein, J.L. et al., "Nonfarnesylated Tetrapeptide Inhibitors of Protein Farnesyltransferase," The Journal of Biological Chemistry, vol. 266, No. 24, pp. 15575–15578 (1991).

Graham, S.L., "Inhibitors of protein farnesylation: a new approach to cancer chemotherapy ," Exp. Opin. Ther. Patents vol. 5 (12), pp. 1269–1285 (1995).

James, G.L. et al., "Benzodiazepine Peptidomimetics: Potent Inhibitors of Ras Farnesylation in Animal Cells," Science, vol. 260 pp. 1937–1942 (1993).

James, G.L. et al., "Benzodiazepine Peptidomimetic BZA–5B Interrupts the MAP Kinase Activation Pathway in H–Ras–transformed Rat–1 Cells, but Not in Untransformed Cells," The Journal of Biological Chemistry, vol. 269, No. 44, pp. 27705–27714 (1994).

James, G., et al., "Polylysine and CVIM Sequences of K–RasB Dictate Specificity of Prenylation and Confer Resistance to Benzodiazepine Peptidomimetic in Vitro," The Journal of Biological Chemistry, vol. 270, No. 11, pp. 6221–6226 (1995).

Kohl, N.E., et al., "Inhibition of farnesyltransferase induces regression of mammary and salivary carcinomas in ras transgenic mice," Nature Medicine, vol. 1, No. 8, pp. 792–797 (1995).

Kohl, N.E. et al., "Protein farnesyltransferase inhibitors block the growth of ras–dependent tumors in nude mice", Proc. Natl. Acad. Sci. USA, Med. Sciences, vol. 91, pp. 9141–9145 (1994).

Kohl, N.E. et al., "Selective Inhibition of ras–Dependent Transformation by a Farnesyltransferase Inhibitor", Science, vol. 260, pp. 1934–1937 (1993).

Pompliano, D.L., "Steady–State Kinetic Mechanism of Ras Farnesyl:Protein Transferase," Biochemistry, vol. 31, pp. 3800–3807 (1992).

Sepp–Lorenzino, L., et al., "A Peptidomimetic Inhibitor of Farnesyl:Protein Transferase Blocks the Anchorage–dependent and –independent Growth of Human Tumor Cell Lines," Cancer Research, vol. 55, pp. 5302–5309 (1995).

*Primary Examiner*—Zinna Northington Davis
*Attorney, Agent, or Firm*—Dianne Pecoraro; David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

49 Claims, No Drawings

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
       (A) LENGTH: 15 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:1:

Gly Lys Lys Lys Lys Lys Ser Lys Thr Lys Cys Val Ile Met
 1               5                  10                  15

(2) INFORMATION FOR SEQ ID NO:2:

(i) SEQUENCE CHARACTERISTICS:
       (A) LENGTH: 86 base pairs
       (B) TYPE: nucleic acid
       (C) STRANDEDNESS: single
       (D) TOPOLOGY: linear (ii) MOLECULE TYPE: Genomic DNA (xi) SEQUENCE DESCRIPTION: SEQ ID NO:2:

TCTCCTCGAG GCCACCATGG GGAGTAGCAA GAGCAAGCCT AAGGACCCCA GCCAGCGCCG     60

GATGACAGAA TACAAGCTTG TGGTGG                                         86

(2) INFORMATION FOR SEQ ID NO:3:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: Genomic DNA (xi) SEQUENCE DESCRIPTION: SEQ ID NO:3:

CACATCTAGA TCAGGACAGC ACAGACTTGC AGC                                 33

(2) INFORMATION FOR SEQ ID NO:4:

(i) SEQUENCE CHARACTERISTICS:
       (A) LENGTH: 41 base pairs
       (B) TYPE: nucleic acid
       (C) STRANDEDNESS: single
       (D) TOPOLOGY: linear (ii) MOLECULE TYPE: Genomic DNA (xi) SEQUENCE DESCRIPTION: SEQ ID NO:4:

TCTCCTCGAG GCCACCATGA CAGAATACAA GCTTGTGGTG G                        41

(2) INFORMATION FOR SEQ ID NO:5:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (ii) MOLECULE TYPE: Genomic DNA (xi) SEQUENCE DESCRIPTION: SEQ ID NO:5:

CACTCTAGAC TGGTGTCAGA GCAGCACACA CTTGCAGC                                  38

(2) INFORMATION FOR SEQ ID NO:6:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:6:

GAGAGAATTC GCCACCATGA CGGAATATAA GCTGGTGG                                  38

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:7:

GAGAGTCGAC GCGTCAGGAG AGCACACACT TGC                                       33

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:8:

CCGCCGGCCT GGAGGAGTAC AG                                                   22

(2) INFORMATION FOR SEQ ID NO:9:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:9:

GAGAGAATTC GCCACCATGA CTGAGTACAA ACTGGTGG                                  38

(2) INFORMATION FOR SEQ ID NO:10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:10:

GAGAGTCGAC TTGTTACATC ACCACACATG GC                                        32

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:11:

GTTGGAGCAG TTGGTGTTGG G                            21

(2) INFORMATION FOR SEQ ID NO:12:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:12:

GAGAGGTACC GCCACCATGA CTGAATATAA ACTTGTGG            38

(2) INFORMATION FOR SEQ ID NO:13:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:13:

CTCTGTCGAC GTATTTACAT AATTACACAC TTTGTC              36

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:14:

GTAGTTGGAG CTGTTGGCGT AGGC                      24

INHIBITORS OF FARNESYL-PROTEIN TRANSFERASE

DOMESTIC PRIORITY CLAIM

This application claims priority from the U.S. Provisional Application No. 60/032,579, filed on Dec. 5, 1996.

BACKGROUND OF THE INVENTION

The Ras protein is part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, Ann. Rev. Biochem. 62:851–891 (1993)). Mutated ras genes are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., Nature 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., Ann. Rev. Biochem. 61:355–386 (1992); W. R. Schafer and J. Rine, Ann. Rev. Genetics 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., J. Biol. Chem. 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., Science, 260:1934–1937 (1993) and G. L. James et al., Science, 260:1937–1942 (1993). Recently, it has been shown that an inhibitor of farnesyl-protein transferase blocks the growth of ras-dependent tumors in nude mice (N. E. Kohl et al., Proc. Natl. Acad. Sci U.S.A., 91:9141–9145 (1994) and induces regression of mammary and salivary carcinomas in ras transgenic mice (N. E. Kohl et al., Nature Medicine, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., Science 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., Cell, 62:81–88 (1990); Schaber et al., J. Biol. Chem., 265:14701–14704 (1990); Schafer etal., Science, 249:1133–1139 (1990); Manne et al., Proc. Natl. Acad. Sci USA, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., PNAS, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., Science, 260:1934–1937 (1993); Graham, et al., J. Med. Chem., 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been shown that farnesyl-protein transferase inhibitors are inhibitors of proliferation of vascular smooth muscle cells and are therefore useful in the prevention and therapy of arteriosclerosis and diabetic disturbance of blood vessels (JP H7-112930). It has also recently been disclosed that certain 1,2,3,4-tetrahydroisoquinoline peptidomimetic compounds, some of which incorporate an imidazole moiety, are inhibitors of FPTase (U.S. Pat. No. 5,439,918, EP 0 618 221 A2 and EP 0 675 112 A1).

It is, therefore, an object of this invention to develop novel peptidomimetic compounds that do not have a thiol moiety, and that will inhibit farnesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention comprises peptidomimetic 1,2,3,4-tetrahydroisoquinolines and homologous compounds which inhibit farnesyl-protein transferase. Furthermore, these compounds differ from such heterocyclic compounds previously described as inhibitors of farnesyl-protein transferase with respect to the alkyl or heteroatom containing linker between the tetrahydroisoquinoline nitrogen and the imidazolyl moiety, and with respect to the lack of a thiol moiety in the instant compounds. Further contained in this invention are chemotherapeutic compositions containing these farnesyl transferase inhibitors and methods for their production.

The compounds of this invention are illustrated by the formulae I and A:

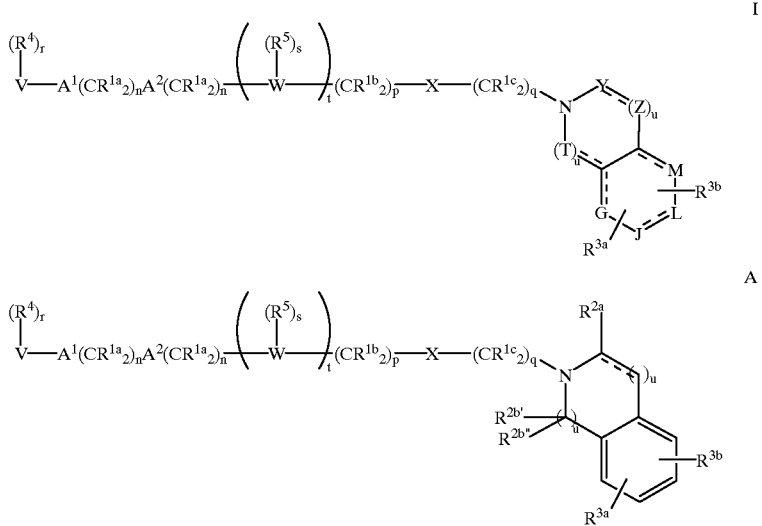

DETAILED DESCRIPTION OF THE INVENTION

The compounds of this invention are useful in the inhibition of farnesyl-protein transferase and the farnesylation of the oncogene protein Ras. In a first embodiment of this invention, the inhibitors of farnesyl-protein transferase are illustrated by the formula I:

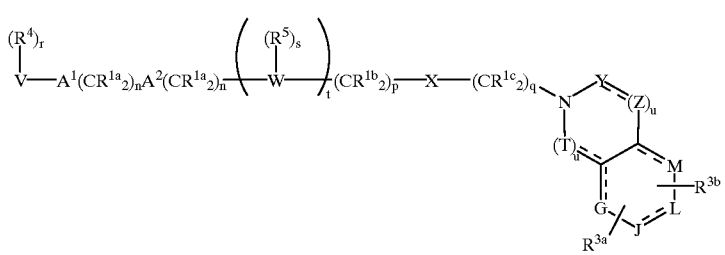

wherein:

$R^{1a}$, $R^{1b}$ and $R^{1c}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, $N_3$, —$N(R^8)_2$, or $R^9OC(O)NR^8$—,
c) $C_1$–$C_6$ alkyl unsubstituted or substituted by unsubstituted or substituted aryl, heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)$—$NR^8$—, provided that $R^{1a}$ is not unsubstituted or substituted imidazolyl;

$R^{2a}$, $R^{2b'}$ and $R^{2b''}$ are independently hydrogen, $NH_2$ or —$(CR^{11}_2)_\nu A^3(CR^{12}_2)_w R^{13}$; or
$R^{2b'}$ and $R^{2b''}$ are combined as O;

$R^{3a}$ and $R^{3b}$ are independently selected from:
a) hydrogen,
b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8_2N$—$C(NR^8)$—, CN, $NO_2$, $R^8C(O)$—, $N_3$, —$N(R^8)_2$, or $R^9OC(O)NR^8$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8_2N$—$C(NR^8)$—, CN, $R^8C(O)$—, $N_3$, —$N(R^8)_2$, and $R^9OC(O)$—$NR^8$—;

$R^4$ is independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $R^8_2N$—$C(NR^8)$—, $R^8C(O)$—, $R^8OC(O)$—, $N_3$, —$N(R^8)_2$, or $R^9OC(O)NR^8$—, and
c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, CN, $H_2N$—C(NH)—, $R^8C(O)$—, $R^8OC(O)$—, $N_3$, —$N(R^8)_2$, or $R^8OC(O)NH$—, provided that $R^4$ is not unsubstituted or substituted imidazolyl;

$R^5$ is independently selected from:
a) hydrogen,
b) $C_2$–$C_6$ alkenyl, $C_2$–$C_6$ alkynyl, $C_3$–$C_6$ cycloalkyl, perfluoroalkyl, F, Cl, Br, $R^8O$—, $R^9S(O)_m$—, $R^8C(O)NR^8$—, CN, $NO_2$, $(R^8)_2N$—C—$(NR^8)$—, $R^8C(O)$—, $R^8OC(O)$—, $N_3$, —$N(R^8)_2$, or $R^9OC(O)NR^8$—, and
c) $C_1$–$C_6$ alkyl, unsubstituted or substituted by perfluoroalkyl, F, Cl, Br, $R^8O$—, $R^9S(O)_m$—, $R^8C(O)NR^8$—, CN, $(R^8)_2N$—C$(NR^8)$—, $R^8C(O)$—, $R^8OC(O)$—, $N_3$, —$N(R^8)_2$, or $R^9OC(O)NR^8$—;

$R^8$ is independently selected from hydrogen, $C_1$–$C_6$ alkyl, benzyl, 2,2,2-trifluoroethyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:
a) $C_{1-4}$ alkoxy,
b) aryl or heterocycle,
c) halogen,
d) HO, e) 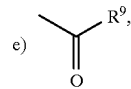

f) 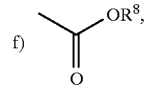

g) 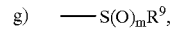

h) $N(R^8)_2$, or
i) $C_{3-6}$ cycloalkyl;

$R^{11}$ and $R^{12}$ are independently selected from:
a) hydrogen,
b) $C_1$–$C_6$ alkyl unsubstituted or substituted by $C_2$–$C_{20}$ alkenyl, $R^8O$—, $R^9S(O)_m$—, $R^8C(O)NR^8$—, CN, $N_3$, $(R^8)_2N$—C$(NR^8)$—, $R^8C(O)$—, —$N(R^8)_2$, or $R^9OC(O)NR^8$—,
c) unsubstituted or substituted aryl, unsubstituted or substituted heterocycle, $C_3$–$C_{10}$ cycloalkyl, $C_2$–$C_{20}$ alkenyl, halogen, $R^8O$—, $R^9S(O)_m$—, $R^8C(O)NR^8$—, CN, $NO_2$, $(R^8)_2N$—C$(NR^8)$—, $R^8C(O)$—, $N_3$, —$N(R^8)_2$, or $R^9OC(O)NR^8$—, and
d) $C_1$–$C_6$ alkyl substituted with an unsubstituted or substituted group selected from aryl, heterocyclic and $C_3$–$C_{10}$ cycloalkyl;

$R^{13}$ is selected from:
a) hydrogen, b) substituted or unsubstituted aryl, substituted or unsubstituted heterocycle, $C_3$–$C_{10}$ cycloalkyl, $C_2$–$C_{20}$ alkenyl, $C_2$–$C_{20}$ alkynyl, $C_1$–$C_{20}$ perfluoroalkyl, allyloxy, F, Cl, Br, $R^8O$—, $R^9S(O)_m$—, $R^8C(O)NR^8$—, CN, $NO_2$, $R^8{}_2N$—C$(NR^8)$—, $R^8C(O)$—, $N_3$, —$N(R^8)_2$, $(R^9)_2NC(O)$— or $R^9OC(O)NR^8$—, and
c) $C_1$–$C_6$ alkyl unsubstituted or substituted by substituted or unsubstituted aryl, substituted or unsubstituted heterocycle, $C_3$–$C_{10}$ cycloalkyl, $C_2$–$C_{20}$ alkenyl, $C_2$–$C_{20}$ alkynyl, $C_2$–$C_{20}$ perfluoroalkyl, F, Cl, Br, $R^8O$—, $R^9S(O)_m$—, $R^8C(O)NH$—, CN, $H_2N$—C(NH)—, $R^8C(O)$—, $N_3$, —$N(R^8)_2$, or $R^9OC(O)NH$—;

$A^1$ and $A^2$ are independently selected from: a bond, —CH=CH—, —C≡C—, —C(O)—, —C(O)$NR^8$—, —$NR^8C(O)$—, O, —$N(R^8)$—, —$S(O)_2N(R^8)$—, —$N(R^8)S(O)_2$—, or —$S(O)_m$;

$A^3$ are independently selected from: a bond, —CH=CH—, —C≡C—, —C(O)—, —C(O)$NR^{10}$—, —$NR^{10}C(O)$—, O, —$N(R^{10})$—, —$S(O)_2N(R^{10})$—, —$N(R^{10})S(O)_2$—, or $S(O)_m$;

G, J, L and M are independently selected from: CHy or N;

T is selected from: N, $CR^{2b'}$ or $CR_{2b}R_{2b''}$;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

and provided that V is not imidazolyl;

W is a heterocycle;
X is a bond, —$S(O)_m$—, O or —C(=O)—;
Y is selected from: $CR^{2a}$, C=O, C=NH or N;
Z is selected from: $CR^{2a}$, C=O or N;
m is 0, 1 or 2;
n is 0, 1, 2, 3 or 4;
p is 0, 1, 2, 3 or 4;
q is 0, 1, 2, 3 or 4, provided that q is not 0 or 1 if X is O;
r is 0 to 5, provided that r is 0 when V is hydrogen;
s is 1 or 2;
t is independently 0 or 1;
u is independently 0,1 or 2;
v is 0, 1, 2, 3 or 4, provided that v is not 0 when $A^3$ is —$NR^{10}C(O)$—, O, —$N(R^{10})$—, —$S(O)_2N(R^{10})$—, —$N(R^{10})S(O)_2$—, or $S(O)_m$;
w is 0, 1, 2, 3 or 4; and
y is 1 or 2;
the dashed lines represent optional double bonds;

or an optical isomer or a pharmaceutically acceptable salt thereof.

In another embodiment of this invention, the inhibitors of farnesyl-protein transferase are illustrated by the formula A:

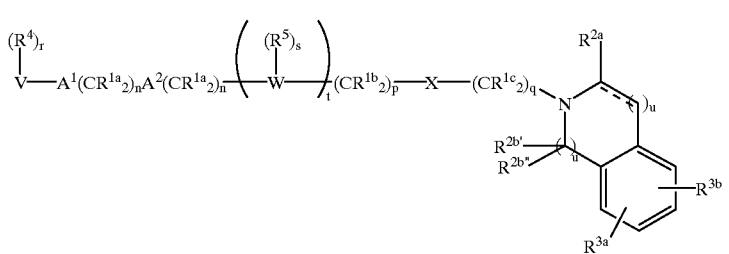

wherein:

$R^{1a}$, $R^{1b}$ and $R^{1c}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, $N_3$, —$N(R^8)_2$, or $R^9OC(O)NR^8$—,
c) $C_1$–$C_6$ alkyl unsubstituted or substituted by unsubstituted or substituted aryl, heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)$—$NR^8$—, provided that $R_{1a}$ is not unsubstituted or substituted imidazolyl;

$R^{2a}$, $R^{2b'}$ and $R^{2b''}$ are independently hydrogen or —$(CR^{11}_2)_v A^3(CR^{12}_2)_w R^{13}$; or $R^{2b'}$ and $R^{2b''}$ are combined as O;

$R^{3a}$ and $R^{3b}$ are independently selected from:
a) hydrogen,
b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8_2N$—$C(NR^8)$—, CN, $NO_2$, $R^8C(O)$—, $N_3$, —$N(R^8)_2$, or $R^9OC(O)NR^8$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8_2N$—$C(NR^8)$—, CN, $R^8C(O)$—, $N_3$, —$N(R^8)_2$, and $R^9OC(O)$—$NR^8$—;

$R^4$ is independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $R^8_2N$—$C(NR^8)$—, $R^8C(O)$—, $R^8OC(O)$—, $N_3$, —$N(R^8)_2$, or $R^9OC(O)NR^8$—, and
c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, CN, $H_2N$—$C(NH)$—, $R^8C(O)$—, $R^8OC(O)$—, $N_3$, —$N(R^8)_2$, or $R^8OC(O)NH$—, provided that $R^4$ is not unsubstituted or substituted imidazolyl;

$R^5$ is independently selected from:
a) hydrogen,
b) $C_2$–$C_6$ alkenyl, $C_2$–$C_6$ alkynyl, $C_3$–$C_6$ cycloalkyl, perfluoroalkyl, F, Cl, Br, $R^8O$—, $R^9S(O)_m$—, $R^8C(O)NR^8$—, CN, $NO_2$, $(R^8)_2N$—$C$—$(NR^8)$—, $R^8C(O)$—, $R^8OC(O)$—, $N_3$, —$N(R^8)_2$, or $R^9OC(O)NR^8$—, and
c) $C_1$–$C_6$ alkyl, unsubstituted or substituted by perfluoroalkyl, F, Cl, Br, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)NR^8$—;

$R^8$ is independently selected from hydrogen, $C_1$–$C_6$ alkyl, benzyl, 2,2,2-trifluoroethyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:
a) $C_{1-4}$ alkoxy,
b) aryl or heterocycle,
c) halogen,
d) HO, e) 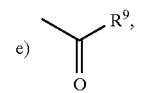

f) 

g) 

h) $N(R^8)_2$, or
i) $C_{3-6}$ cycloalkyl;

$R^{11}$ and $R^{12}$ are independently selected from:
a) hydrogen,
b) $C_1$–$C_6$ alkyl unsubstituted or substituted by $C_2$–$C_{20}$ alkenyl, $R^8O$—, $R^9S(O)_m$—, $R^8C(O)NR^8$—, CN, $N_3$, $(R^8)_2N$—$C(NR^8)$—, $R^8C(O)$—, —$N(R^8)_2$, or $R^9OC(O)NR^8$—,
c) unsubstituted or substituted aryl, unsubstituted or substituted heterocycle, $C_3$–$C_{10}$ cycloalkyl, $C_2$–$C_{20}$ alkenyl, halogen, $R^8O$—, $R^9S(O)_m$—, $R^8C(O)NR^8$—, CN, $NO_2$, $(R^8)_2N$—$C(NR_8)$—, $R^8C(O)$—, $N_3$, —$N(R^8)_2$, or $R^9OC(O)NR^8$—, and
d) $C_1$–$C_6$ alkyl substituted with an unsubstituted or substituted group selected from aryl, heterocyclic and $C_3$–$C_{10}$ cycloalkyl;

$R^{13}$ is selected from:
a) hydrogen,
b) substituted or unsubstituted aryl, substituted or unsubstituted heterocycle, $C_3$–$C_{10}$ cycloalkyl, $C_2$–$C_{20}$ alkenyl, $C_2$–$C_{20}$ alkynyl, $C_1$–$C_{20}$ perfluoroalkyl, allyloxy, F, Cl, Br, $R^8O$—, $R^9S(O)_m$—, $R^8C(O)NR^8$—, CN, $NO_2$, $R^8{}_2N$—$C(NR^8)$—, $R^8C(O)$—, $N_3$, —$N(R^8)_2$, $(R^9)_2NC(O)$— or $R^9OC(O)NR^8$—, and
c) $C_1$–$C_6$ alkyl unsubstituted or substituted by substituted or unsubstituted aryl, substituted or unsubstituted heterocycle, $C_3$–$C_{10}$ cycloalkyl, $C_2$–$C_{20}$ alkenyl, $C_2$–$C_{20}$ alkynyl, $C_2$–$C_{20}$ perfluoroalkyl, F, Cl, Br, $R^8O$—, $R^9S(O)_m$—, $R^8C(O)NH$—, CN, $H_2N$—$C(NH)$—, $R^8C(O)$—, $N_3$, —$N(R^8)_2$, or $R^9OC(O)NH$—;

$A^1$ and $A^2$ are independently selected from: a bond, —CH=CH—, —C≡C—, —C(O)—, —C(O)NR$^8$—, —NR$^8$C(O)—, O, —N(R$^8$)—, —S(O)$_2$N(R$^8$)—, —N(R$^8$)S(O)$_2$—, or —S(O)$_m$—;

$A^3$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl,
provided that V is not hydrogen if $A^1$ is $S(O)_m$ and V is not hydrogen if $A^1$ is a bond, n is 0 and $A^2$ is $S(O)_m$; and provided that V is not imidazolyl;

W is a heterocycle;
X is a bond, —$S(O)_m$—, O or —C(=O)—;
m is 0,1 or 2;
n is 0, 1, 2, 3 or 4;
p is 0, 1, 2, 3 or 4;
q is 0, 1, 2, 3 or 4, provided that q is not 0 or 1 if X is O;
r is 0 to 5, provided that r is 0 when V is hydrogen;
s is 1 or 2;
t is 0 or 1;
u is independently 0,1 or 2;
v is 0, 1, 2, 3 or 4, provided that v is not 0 when $A^3$ is —NR$^{10}$C(O)—, O, —N(R$_{10}$), —S(O)$_2$N(R$_{10}$)—, —N(R$^{10}$)S(O)$_2$—, or S(O)$_m$;
w is 0, 1, 2, 3 or 4; and
the dashed lines represent optional double bonds;

or an optical isomer or a pharmaceutically acceptable salt thereof.

A preferred embodiment of the compounds of this invention is illustrated by the following formula:

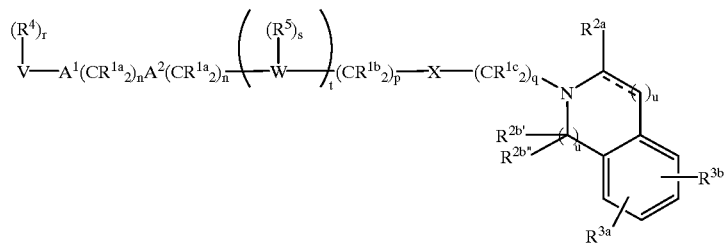

A wherein:
$R^{1a}$ and $R^{1c}$ are independently selected from: hydrogen, $C_3$–$C_{10}$ cycloalkyl, $R^8O$—, —$N(R^8)_2$, F or $C_1$–$C_6$ alkyl;

$R^{1b}$ is independently selected from:
a) hydrogen,
b) unsubstituted or substituted aryl, unsubstituted or substituted heterocycle, $C_3$–$C_6$ cycloalkyl, $R^8O$—, —$N(R^8)_2$ or $C_2$–$C_6$ alkenyl,
c) $C_1$–$C_6$ alkyl unsubstituted or substituted by unsubstituted or substituted aryl, heterocycle, $C_3$–$C_6$ cycloalkyl, $C_2$–$C_6$ alkenyl, $R^8O$—, or —$N(R^8)_2$;

$R^{2a}$ and $R_{2b'}$ are independently selected from: H; $C_1$–$C_6$ alkyl,

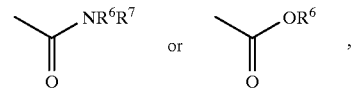

$R^{3a}$ and $R_{3b}$ are independently selected from:
a) hydrogen,
b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8{}_2N$—$C(NR^8)$—, CN, $NO_2$, $R^8C(O)$—, $N_3$, —$N(R^8)_2$, or $R^9OC(O)NR^8$—,
c) unsubstituted $C_1$–$C_6$ alkyl,
d) substituted $C_1$–$C_6$ alkyl wherein the sub stituent on the substituted $C_1$–$C_6$ alkyl is selected from unsubstituted or substituted aryl, unsubstituted or substituted heterocyclic, $C_2$–$C_6$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8{}_2N$—$C(NR^8)$—, CN, $R^8C(O)$—, $N_3$, —$N(R^8)_2$, and $R^9OC(O)$—$NR^8$—;

$R^4$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$, or $R^9OC(O)NR^8$—;

$R^5$ is selected from:
 a) hydrogen,
 b) $C_2$–$C_6$ alkenyl, $C_2$–$C_6$ alkynyl, $C_3$–$C_6$ cycloalkyl, $C_1$–$C_6$ perfluoroalkyl, F, Cl, $R^8O$—, $R^9S(O)_m$—, $R^8C(O)NR^8$—, CN, $(R^8)_2N$—$C(NR^8)$—, $R^8C(O)$—, $R^8OC(O)$—, —$N(R^8)_2$, or $R^9OC(O)NR^8$—, and
 c) $C_1$–$C_6$ alkyl unsubstituted or substituted by $C_1$–$C_6$ perfluoroalkyl, F, Cl, $R^8O$—, $R^9S(O)_m$—, $R^8C(O)NR^8$—, CN, $(R^8)_2N$—$C(NR^8)$—, $R^8C(O)$—, $R^8OC(O)$—, —$N(R^8)_2$, or $R^9OC(O)NR^8$—;

$R^6$ and $R^7$ are independently selected from:
 H; $C_{1-4}$ alkyl, $C_{3-6}$ cycloalkyl, aryl, heterocycle, unsubstituted or substituted with one or two:
  a) $C_{1-4}$ alkoxy,
  b) halogen, or
  c) substituted or unsubstituted aryl or substituted or unsubstituted heterocycle, $R^8$ is independently selected from hydrogen, $C_1$–$C_6$ alkyl, benzyl, 2,2,2-trifluoroethyl and aryl;

$R^9$ is independently selected from $C_1$–$C_6$ alkyl and aryl;

$A^1$ and $A^2$ are independently selected from: a bond, —CH=CH—, —C≡C—, —C(O)—, —C(O)NR^8—, O, —$N(R^8)$—, or —$S(O)_m$;

V is selected from:
 a) heterocycle selected from pyrrolidinyl, imidazolyl, pyridinyl, thiazolyl, indolyl, quinolinyl, isoquinolinyl, and thienyl, and
 b) aryl;

W is a heterocycle selected from pyrrolidinyl, triazolyl, imidazolyl, pyridinyl, thiazolyl, indolyl, quinolinyl, or isoquinolinyl;

X is a bond, —$S(O)_m$—, O or —C(=O)—;

m is 0, 1 or 2;

n is 0, 1, 2, 3 or 4;

p is 1, 2 or 3;

q is 0, 1 or 2, provided that q is not 0 or 1 if X is O;

r is 0 to 5, provided that r is 0 when V is hydrogen;

s is 1 or 2;

t is 1; and u is independently 0 or 1;

or an optical isomer or a pharmaceutically acceptable salt thereof.

In another more preferred embodiment of this invention, the inhibitors of farnesyl-protein transferase are illustrated by the formula A1:

b) unsubstituted or substituted aryl, unsubstituted or substituted heterocycle, $C_3$–$C_6$ cycloalkyl, $R^8O$—, —$N(R^8)_2$ or $C_2$–$C_6$ alkenyl,
c) $C_1$–$C_6$ alkyl unsubstituted or substituted by unsubstituted or substituted aryl, heterocycle, $C_3$–$C_6$ cycloalkyl, $C_2$–$C_6$ alkenyl, $R^8O$—, or —$N(R^8)_2$;

$R^{2a}$ is selected from: H; $C_1$–$C_6$ alkyl, $NH_2$ $R^{3a}$ and $R^{3b}$ are independently selected from:
 a) hydrogen,
 b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8{}_2N$—$C(NR^8)$—, CN, $NO_2$, $R^8C(O)$—, $N_3$, —$N(R^8)_2$, or $R^9OC(O)NR^8$—,
 c) unsubstituted $C_1$–$C_6$ alkyl,
 d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8{}_2N$—$C(NR^8)$—, CN, $R^8C(O)$—, $N_3$, —$N(R^8)_2$, and $R^9OC(O)$—$NR^8$—;

$R^4$ is independently selected from:
 a) hydrogen,
 b) $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
 c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$, or $R^9OC(O)NR^8$—;

$R^5$ is selected from:
 a) hydrogen,
 b) $C_2$–$C_6$ alkenyl, $C_2$–$C_6$ alkynyl, $C_3$–$C_6$ cycloalkyl, $C_1$–$C_6$ perfluoroalkyl, F, Cl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
 c) $C_1$–$C_6$ alkyl unsubstituted or substituted by $C_1$–$C_6$ perfluoroalkyl, F, Cl, $R^8O$—, $R^9S(O)_m$—, $R^8C(O)$

A1 wherein
$R^{1a}$ and $R^{1c}$ are independently selected from: hydrogen, $C_3$–$C_{10}$ cycloalkyl, $R^8O$—, —$N(R^8)_2$, F or $C_1$–$C_6$ alkyl;

$R^{1b}$ is independently selected from:
 a) hydrogen, $NR^8$—, CN, $(R^8)_2N$—$C(NR^8)$—, $R^8C(O)$—, $R^8OC(O)$—, —$N(R^8)_2$, or $R^9OC(O)NR^8$—;

$R^6$ and $R^7$ are independently selected from:
 H; $C_{1-4}$ alkyl, $C_{3-6}$ cycloalkyl, aryl, heterocycle, unsubstituted or substituted with one or two:
  a) $C_{1-4}$ alkoxy, b) halogen, or
c) substituted or unsubstituted aryl or substituted or unsubstituted heterocycle, $R^8$ is independently selected from hydrogen, $C_1$–$C_6$ alkyl, benzyl, 2,2,2-trifluoroethyl and aryl;

$R^9$ is independently selected from $C_1$–$C_6$ alkyl and aryl;

$A^1$ and $A^2$ are independently selected from: a bond, —CH=CH—, —C≡C—, —C(O)—, —C(O)NR$^8$—, —NR$^8$C(O)—, O, —N(R$^8$)—, —S(O)$_2$N(R$^8$)—, —N(R$^8$)S(O)$_2$—, or —S(O)$_m$;

G and M are independently selected from: CHy or N;

V is selected from:
a) heterocycle selected from pyrrolidinyl, imidazolyl, pyridinyl, thiazolyl, indolyl, quinolinyl, isoquinolinyl, and thienyl, and
b) aryl;

W is a heterocycle selected from pyrrolidinyl, triazolyl, imidazolyl, pyridinyl, thiazolyl, indolyl, quinolinyl, or isoquinolinyl;

X is a bond, —S(O)$_m$—, O or —C(=O)—;

Y is selected from: $CR^{2a}$, C=O, C=NH or N;

Z is selected from: $CR^{2a}$, C=O or N;

m is 0, 1 or 2;

n is 0, 1, 2, 3 or 4;

p is 1, 2 or 3;

q is 0, 1 or 2, provided that q is not 0 or 1 if X is O;

r is 0 to 5, provided that r is 0 when V is hydrogen;

s is 1 or 2;

t is 1; and y is 1 or 2;

or an optical isomer or a pharmaceutically acceptable salt thereof.

Another preferred embodiment of the compounds of this invention are illustrated by the formula B:

$R^{2a}$ and $R_{2b'}$ are independently selected from selected from: H; $C_1$–$C_6$ alkyl,

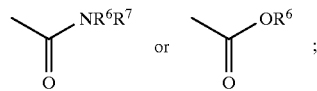

$R^{3a}$ and $R_{3b}$ are independently selected from:
a) hydrogen,
b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8_2N$—C(NR$^8$)—, CN, NO$_2$, $R^8C(O)$—, N$_3$, —N(R$^8$)$_2$, or $R^9OC(O)NR^8$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8_2N$—C(NR$^8$)—, CN, $R^8C(O)$—, N$_3$, —N(R$^8$)$_2$, and $R^9OC(O)$—NR$^8$—;

$R^4$ is independently selected from:
a) hydrogen,
b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, NO$_2$, $(R^8)_2N$—C(NR$^8$)—, $R^8C(O)$—, —N(R$^8$)$_2$, or $R^9OC(O)NR^8$—, and
c) $C_1$–$C_6$ alkyl substituted by $C_1$–$C_6$ perfluoroalkyl, $R^8O$—, $R^8C(O)NR^8$—, $(R^8)_2N$—C(NR$^8$)—, $R^8C(O)$—, —N(R$^8$)$_2$, or $R^9OC(O)NR^8$—;

$R^{5a}$ and $R_{5b}$ are independently hydrogen, $C_1$–$C_6$ alkyl, cyclopropyl, trifluoromethyl and halogen;

B

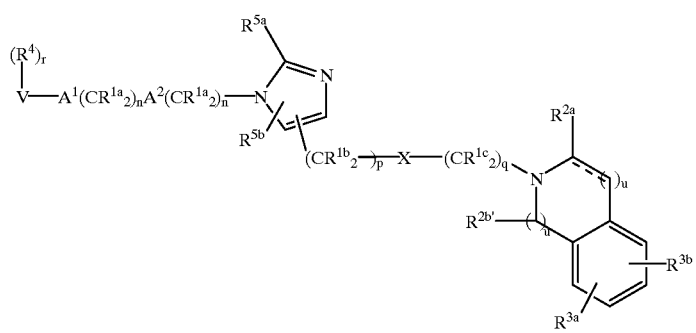

wherein:
$R^{1a}$ and $R_{1c}$ are independently selected from: hydrogen, $C_3$–$C_{10}$ cycloalkyl, $R^8O$—, —N(R$^8$)$_2$, F or $C_1$–$C_6$ alkyl;

$R^{1b}$ is independently selected from:
a) hydrogen,
b) aryl, heterocycle, $C_3$–$C_{10}$ cycloalkyl, $R^8O$—, —N(R$^8$)$_2$, F or $C_2$–$C_6$ alkenyl,
c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^8O$— and —N(R$^8$)$_2$;

$R^6$ and $R^7$ are independently selected from:
H; $C_{1-4}$ alkyl, $C_{3-6}$ cycloalkyl, aryl, heterocycle, unsubstituted or substituted with one or two:
a) $C_{1-4}$ alkoxy,
b) halogen, or
c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$A^1$ and $A^2$ are independently selected from: a bond, —CH=CH—, —C≡C—, —C(O)—, —C(O)NR$^8$—, O, —N(R$^8$)—, or —S(O)$_m$;

V is selected from:
a) hydrogen,
b) heterocycle selected from pyrrolidinyl, imidazolinyl, pyridinyl, thiazolyl, oxazolyl, indolyl, quinolinyl, isoquinolinyl, triazolyl and thienyl,
c) aryl,
d) $C_1-C_{20}$ alkyl wherein from 0 to 4 carbon atoms are replaced with a a heteroatom selected from O, S, and N, and
e) $C_2-C_{20}$ alkenyl, and provided that V is not hydrogen if $A^1$ is $S(O)_m$ and V is not hydrogen if $A^1$ is a bond, n is 0 and $A^2$ is $S(O)_m$;

X is a bond, $—S(O)_m—$, O or $—C(=O)—$;

m is 0, 1 or 2;

n is 0, 1, 2, 3 or 4;

p is 0, 1, 2, 3 or 4;

q is 0, 1 or 2, provided that q is not 0 or 1 if X is O;

r is 0 to 5, provided that r is 0 when V is hydrogen; and u is independently 0 or 1;

or an optical isomer or pharmaceutically acceptable salt thereof.

In another more preferred embodiment of this invention, the inhibitors of farnesyl-protein transferase are illustrated by the formula B1:

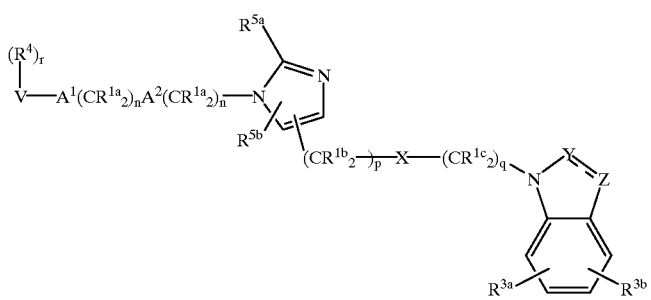

B1 wherein $R^{1a}$ and $R^{1c}$ are independently selected from: hydrogen, $C_3-C_{10}$ cycloalkyl, $R^8O—$, $—N(R^8)_2$, F or $C_1-C_6$ alkyl;

$R^{1b}$ is independently selected from:
a) hydrogen,
b) aryl, heterocycle, $C_3-C_{10}$ cycloalkyl, $R^8O—$, $—N(R^8)_2$, F or $C_2-C_6$ alkenyl,
c) unsubstituted or substituted $C_1-C_6$ alkyl wherein the substituent on the substituted $C_1-C_6$ alkyl is selected from unsubstituted or substituted aryl, heterocycle, $C_3-C_{10}$ cycloalkyl, $C_2-C_6$ alkenyl, $R^8O—$ and $—N(R^8)_2$;

$R_{2a}$ is selected from selected from: H; $C_1-C_6$ alkyl,

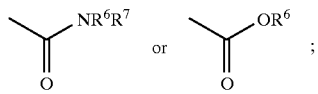

$R_{3a}$ and $R_{3b}$ are independently selected from:
a) hydrogen,
b) unsubstituted or substituted aryl, unsubstituted or substituted heterocycle, unsubstituted or substituted $C_3-C_{10}$ cycloalkyl, unsubstituted or substituted $C_2-C_6$ alkenyl, $C_2-C_6$ alkynyl, halogen, $C_1-C_6$ perfluoroalkyl, $R^9O—$, $R^9S(O)_m—$, $R^8C(O)NR^8—$, $(R^8)_2NC(O)—$, $R^9C(O)O—$, $R^8{}_2N—C(NR^8)—$, CN, $NO_2$, $R^8C(O)—$, $N_3$, $—N(R^8)_2$, or $R^9OC(O)NR^8—$,
c) unsubstituted $C_1-C_6$ alkyl,
d) substituted $C_1-C_6$ alkyl wherein the substituent on the substituted $C_1-C_6$ alkyl is selected from unsubstituted or substituted aryl, unsubstituted or substituted heterocyclic, $C_3-C_{10}$ cycloalkyl, $C_2-C_6$ alkenyl, $C_2-C_6$ alkynyl, $R^9O—$, $R^9S(O)_m—$, $R^8C(O)NR^8—$, $(R^8)_2NC(O)—$, $R^8{}_2N—C(NR^8)—$, CN, $R^8C(O)—$, $N_3$, $—N(R^8)_2$, and $R^9OC(O)—NR^8—$;

$R^4$ is independently selected from:
a) hydrogen,
b) aryl, substituted aryl, heterocycle, substituted heterocycle, $C_1-C_6$ alkyl, $C_2-C_6$ alkenyl, $C_2-C_6$ alkynyl, $C_1-C_6$ perfluoroalkyl, F, Cl, $R^8O—$, $R^8C(O)NR^8—$, CN, $NO_2$, $(R^8)_2N—C(NR^8)—$, $R^8C(O)—$, $—N(R^8)_2$, or $R^9OC(O)NR^8—$, and
c) $C_1-C_6$ alkyl substituted by $C_1-C_6$ perfluoroalkyl, $R^8O—$, $R^8C(O)NR^8—$, $(R^8)_2N—C(NR^8)—$, $R^8C(O)—$, $—N(R^8)_2$, or $R^9OC(O)NR^8—$;

$R^{5a}$ and $R^{5b}$ are independently hydrogen, $C_1-C_6$ alkyl, cyclopropyl, trifluoromethyl and halogen;

$R^6$ and $R^7$ are independently selected from:

H; $C_{1-4}$ alkyl, $C_{3-6}$ cycloalkyl, aryl, heterocycle, unsubstituted or substituted with one or two:
a) $C_{1-4}$ alkoxy,
b) halogen, or
c) substituted or unsubstituted aryl or substituted or unsubstituted heterocycle;

$R^8$ is independently selected from hydrogen, $C_1-C_6$ alkyl, 2,2,2-trifluoroethyl, benzyl and aryl;

$R^9$ is independently selected from $C_1-C_6$ alkyl and aryl;

$A^1$ and $A^2$ are independently selected from: a bond, $—CH=CH—$, $—C\equiv C—$, $—C(O)—$, $—C(O)NR^8—$, O, $—N(R^8)—$, or $—S(O)_m$;

V is selected from:
a) hydrogen,
b) heterocycle selected from pyrrolidinyl, imidazolinyl, pyridinyl, thiazolyl, oxazolyl, indolyl, quinolinyl, isoquinolinyl, triazolyl and thienyl,
c) aryl,
d) $C_1-C_{20}$ alkyl wherein from 0 to 4 carbon atoms are replaced with a a heteroatom selected from O, S, and N, and
e) $C_2-C_{20}$ alkenyl, and provided that V is not hydrogen if $A^1$ is $S(O)_m$ and V is not hydrogen if $A^1$ is a bond, n is 0 and $A^2$ is $S(O)_m$;

X is a bond, —S(O)$_m$—, O or —C(=O)—;
Y is selected from: CR$^{2a}$, C=O, C=NH or N;
Z is selected from: CR$^{2a}$, C=O or N;
m is 0, 1 or 2;
n is 0, 1, 2, 3 or 4;
p is 1, 2 or 3;
q is 0, 1 or 2, provided that q is not 0 or 1 if X is O;
r is 0 to 5, provided that r is 0 when V is hydrogen; and
y is 1 or 2;
or an optical isomer or pharmaceutically acceptable salt thereof.

Another preferred embodiment of the compounds of this invention are illustrated by the formula C:

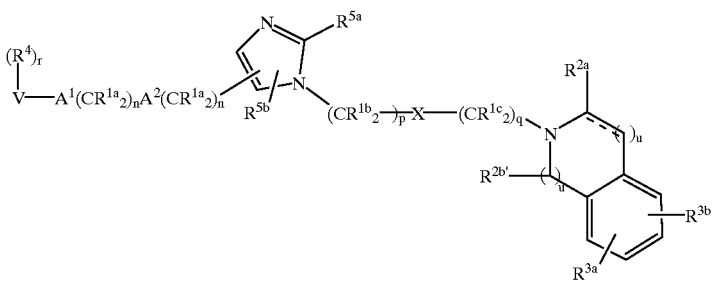

wherein:
R$^{1a}$ and R$^{1c}$ are independently selected from: hydrogen, C$_3$–C$_{10}$ cycloalkyl, R$^8$O—, —N(R$^8$)$_2$, F or C$_1$–C$_6$ alkyl;
R$^{1b}$ is independently selected from:
 a) hydrogen,
 b) aryl, heterocycle, C$_3$–C$_{10}$ cycloalkyl, R$^8$O—, —N(R$^8$)$_2$, F or C$_2$–C$_6$ alkenyl,
 c) unsubstituted or substituted C$_1$–C$_6$ alkyl wherein the substituent on the substituted C$_1$–C$_6$ alkyl is selected from unsubstituted or substituted aryl, heterocycle, C$_3$–C$_{10}$ cycloalkyl, C$_2$–C$_6$ alkenyl, R$^8$O— and —N(R$^8$)$_2$;
R$^{2a}$ and R$^{2b'}$ are independently selected from selected from: H; C$_1$–C$_6$ alcyl,

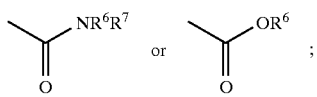

R$^{3a}$ and R$^{3b}$ are independently selected from:
 a) hydrogen,
 b) unsubstituted or substituted aryl, unsubstituted or substituted heterocycle, unsubstituted or substituted C$_3$–C$_{10}$ cycloalkyl, unsubstituted or substituted C$_2$–C$_6$ alkenyl, C$_2$–C$_6$ alkynyl, halogen, C$_1$–C$_6$ perfluoroalkyl, R$^9$O—, R$^9$S(O)$_m$—, R$^8$C(O)NR$^8$—, (R$^8$)$_2$NC(O)—, R$^9$C(O)O—, R$^8$$_2$N—C(NR$^8$)—, CN, NO$_2$, R$^8$C(O)—, N$_3$, —N(R$^8$)$_2$, or R$^9$OC(O)NR$^8$—,
 c) unsubstituted C$_1$–C$_6$ alkyl,
 d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^9$O—, R$^9$S(O)$_m$—, R$^8$C(O)NR$^8$—, (R$^8$)$_2$NC(O)—, R$^8$$_2$N—C(NR$^8$)—, CN, R$^8$C(O)—, N$_3$, —N(R$^8$)$_2$, and R$^9$OC(O)—NR$^8$—;

R$^4$ is independently selected from:
 a) hydrogen,
 b) aryl, substituted aryl, heterocycle, substituted heterocycle, C$_1$–C$_6$ alkyl, C$_2$–C$_6$ alkenyl, C$_2$–C$_6$ alkynyl, C$_1$–C$_6$ perfluoroalkyl, F, Cl, R$^8$O—, R$^8$C(O)NR$^8$—, CN, NO$_2$, (R$^8$)$_2$N—C(NR$^8$)—, R$^8$C(O)—, —N(R$^8$)$_2$, or R$^9$OC(O)NR$^8$—, and
 c) C$_1$–C$_6$ alkyl substituted by C$_1$–C$_6$ perfluoroalkyl, R$^8$O—, R$^8$C(O)NR$^8$—, (R$^8$)$_2$N—C(NR$^8$)—, R$^8$C(O)—, —N(R$^8$)$_2$, or R$^9$OC(O)NR$^8$—;

R$^{5a}$ and R$^{5b}$ are independently hydrogen, C$_1$–C$_6$ alkyl, cyclopropyl, trifluoromethyl and halogen;
R$^6$ and R$^7$ are independently selected from:
 H; C$_{1-4}$ alkyl, C$_{3-6}$ cycloalkyl, aryl, heterocycle, unsubstituted or substituted with one or two:
  a) C$_{1-4}$ alkoxy,
  b) halogen, or
  c) substituted or unsubstituted aryl or substituted or unsubstituted heterocycle;
R$^8$ is independently selected from hydrogen, C$_1$–C$_6$ alkyl, 2,2,2-trifluoroethyl, benzyl and aryl;
R$^9$ is independently selected from C$_1$–C$_6$ alkyl and aryl;
A$^1$ and A$^2$ are independently selected from: a bond, —CH=CH—, —C≡C—, —C(O)—, —C(O)NR$^8$—, O, —N(R$^8$)—, or —S(O)$_m$;
V is selected from:
 a) hydrogen,
 b) heterocycle selected from pyrrolidinyl, imidazolinyl, pyridinyl, thiazolyl, oxazolyl, indolyl, quinolinyl, isoquinolinyl, triazolyl and thienyl,
 c) aryl,
 d) C$_1$–C$_{20}$ alkyl wherein from 0 to 4 carbon atoms are replaced with a a heteroatom selected from O, S, and N, and
 e) C$_2$–C$_{20}$ alkenyl, and
provided that V is not hydrogen if A$^1$ is S(O)$_m$ and V is not hydrogen if A$^1$ is a bond, n is 0 and A$^2$ is S(O)$_m$;
X is a bond, —S(O)$_m$—, O or —C(=O)—;
m is 0, 1 or 2;
n is 0, 1, 2, 3 or 4;
p is 0, 1, 2, 3 or 4, provided that p is not 0 if X is a bond or O;
q is 0, 1 or 2, provided that q is not 0 or 1 if X is O;
r is 0 to 5, provided that r is 0 when V is hydrogen; and
u is independently 0 or 1;
or an optical isomer or pharmaceutically acceptable salt thereof.

In a more preferred embodiment of this invention, the inhibitors of farnesyl—protein transferase are illustrated by the formula D:

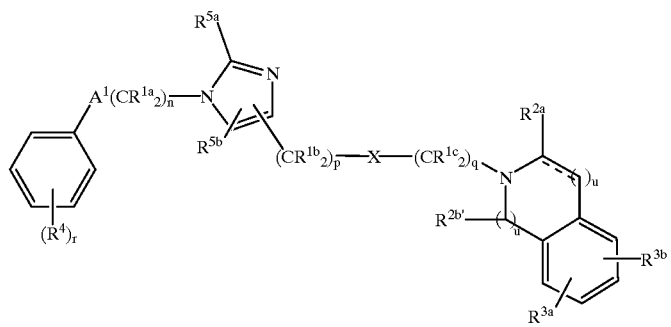

D wherein:

$R^{1a}$ and $R^{1c}$ are independently selected from: hydrogen, $C_3$–$C_{10}$ cycloalkyl or $C_1$–$C_6$ alkyl;

$R^{1b}$ is independently selected from:
a) hydrogen,
b) aryl, heterocycle, $C_3$–$C_{10}$ cycloalkyl, $R^8O$—, —$N(R^8)_2$, F or $C_2$–$C_6$ alkenyl,
c) $C_1$–$C_6$ alkyl unsubstituted or substituted by aryl, heterocycle, $C_3$–$C_{10}$ cycloalkyl, $C_2$–$C_6$ alkenyl, $R^8O$—, or —$N(R^8)_2$;

$R^{2a}$ and $R^{2b'}$ are independently selected from selected from: H; $C_1$–$C_6$ alkyl,

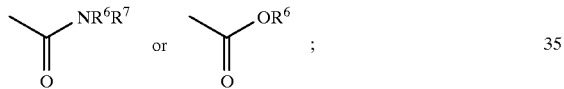

$R^{3a}$ and $R^{3b}$ are independently selected from:
a) hydrogen,
b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8_2N$—$C(NR^8)$—, CN, $NO_2$, $R^8C(O)$—, $N_3$, —$N(R^8)_2$, or $R^9OC(O)NR^8$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8_2N$—$C(NR^8)$—, CN, $R^8C(O)$—, $N_3$, —$N(R^8)_2$, and $R^9OC(O)$—$NR^8$—;

$R^4$ is independently selected from:
a) hydrogen,
b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, —$N(R^8)_2$, or $R^9OC(O)NR^8$—, and
c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —$N(R^8)_2$, or $R^9OC(O)NR^8$—;

$R^{5a}$ and $R^{5b}$ are independently hydrogen, ethyl, cyclopropyl or methyl;

$R^6$ and $R^7$ are independently selected from:
H; $C_{1-4}$ alkyl, $C_{3-6}$ cycloalkyl, aryl, heterocycle, unsubstituted or substituted with one or two:
a) $C_{1-4}$ alkoxy,
b) halogen, or
c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$A^1$ is selected from: a bond, —C(O)—, O, —$N(R^8)$—, or —$S(O)_m$;

X is a bond, —$S(O)_m$—, O or —C(=O)—;

n is 0, 1 or 2; provided that n is not 0 or 1 if $A^1$ is a bond, O, —$N(R^8)$—, or $S(O)_m$;

m is 0, 1 or 2;

p is 0, 1, 2, 3 or 4;

q is 0, 1 or 2, provided that q is not 0 or 1 if X is O;

r is 1 or 2; and is independently 0 or 1;

or an optical isomer or pharmaceutically acceptable salt thereof.

In another more preferred embodiment of this invention, the inhibitors of farnesyl—protein transferase are illustrated by the formula D1:

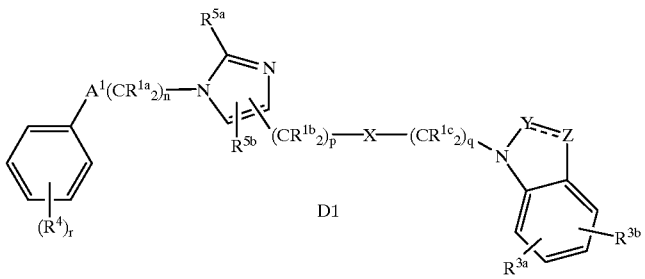

wherein $R^{1a}$ and $R^{1c}$ are independently selected from: hydrogen, $C_3$–$C_{10}$ cycloalkyl or $C_1$–$C_6$ alkyl;

$R^{1b}$ is independently selected from:
a) hydrogen,
b) aryl, heterocycle, $C_3$–$C_{10}$ cycloalkyl, $R^8O$—, —$N(R^8)_2$, F or $C_2$–$C_6$ alkenyl,
c) $C_1$–$C_6$ alkyl unsubstituted or substituted by aryl, heterocycle, $C_3$–$C_{10}$ cycloalkyl, $C_2$–$C_6$ alkenyl, $R^8O$—, or —$N(R^8)_2$;

$R^{2a}$ is selected from selected from: H; $C_1$–$C_6$ alkyl, $NH_2$,

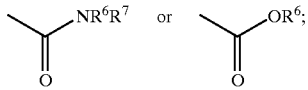

$R^{3a}$ and $R^{3b}$ are independently selected from:
a) hydrogen,
b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8{}_2N$—$C(NR^8)$—, CN, $NO_2$, $R^8C(O)$—, $N_3$, —$N(R^8)_2$, or $R^9OC(O)NR^8$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8{}_2N$—$C(NR^8)$—, CN, $R^8C(O)$—, $N_3$, —$N(R^8)_2$, and $R^9OC(O)$—$NR^8$—;

$R^4$ is independently selected from:
a) hydrogen,
b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, —$N(R^8)_2$, or $R^9OC(O)NR^8$—, and
c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —$N(R^8)_2$, or $R^9OC(O)NR^8$—;

$R^{5a}$ and $R^{5b}$ are independently hydrogen, ethyl, cyclopropyl or methyl;

$R^6$ and $R^7$ are independently selected from:
H; $C_{1-4}$ alkyl, $C_{3-6}$ cycloalkyl, aryl, heterocycle, unsubstituted or substituted with one or two:
a) $C_{1-4}$ alkoxy,
b) halogen, or
c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$A^1$ is selected from: a bond, —C(O)—, O, —$N(R^8)$—, or —$S(O)_m$;

X is a bond, —$S(O)_m$—, O or —C(=O)—;

Y is selected from: $CR^{2a}$, C=NH or N;

Z is selected from: $CR^{2a}$, or N; provided that at least Y or Z is N;

n is 0, 1 or 2; provided that n is not 0 or 1 if $A^1$ is a bond, O, —$N(R^8)$—, or $S(O)_m$;

m is 0, 1 or 2;

p is 0, 1, 2, 3 or 4;

q is 0, 1 or 2, provided that q is not 0 or 1 if X is O;

r is 1 or 2; and y is 1 or 2;

or an optical isomer or pharmaceutically acceptable salt thereof.

In another more preferred embodiment of this invention, the inhibitors of farnesyl-protein transferase are illustrated by the formula E:

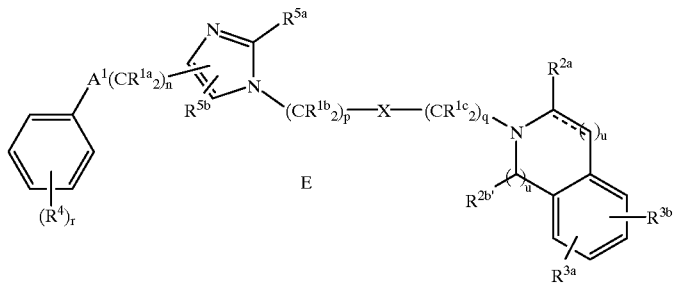

wherein:

R$^{1a}$ and R$^{1c}$ are independently selected from: hydrogen, R$^8$O—, —N(R$^8$)$_2$, F, C$_3$–C$_{10}$ cycloalkyl or C$_1$–C$_6$ alkyl;

R$^{1b}$ is independently selected from:
 a) hydrogen,
 b) aryl, heterocycle, C$_3$–C$_{10}$ cycloalkyl, R$^8$O—, —N(R$^8$)$_2$, F or C$_2$–C$_6$ alkenyl,
 c) C$_1$–C$_6$ alkyl unsubstituted or substituted by aryl, heterocycle, C$_3$–C$_{10}$ cycloalkyl, C$_2$–C$_6$ alkenyl, R$^8$O—, or —N(R$^8$)$_2$;

R$^{2a}$ and R$^{2b'}$ are independently selected from selected from: H; C$_1$–C$_6$ alkyl,

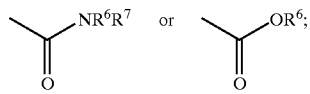

R$^{3a}$ and R$^{3b}$ are independently selected from:
 a) hydrogen,
 b) unsubstituted or substituted aryl, unsubstituted or substituted heterocycle, unsubstituted or substituted C$_3$–C$_{10}$ cycloalkyl, unsubstituted or substituted C$_2$–C$_6$ alkenyl, C$_2$–C$_6$ alkynyl, halogen, C$_1$–C$_6$ perfluoroalkyl, R$^9$O—, R$^9$S(O)$_m$—, R$^8$C(O)NR$^8$—, (R$^8$)$_2$NC(O)—, R$^9$C(O)O—, R$^8_2$N—C(NR$^8$)—, CN, NO$_2$, R$^8$C(O)—, N$_3$, —N(R$^8$)$_2$, or R$^9$OC(O)NR$^8$—,
 c) unsubstituted C$_1$–C$_6$ alkyl,
 d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^9$O—, R$^9$S(O)$_m$—, R$^8$C(O)NR$^8$—, (R$^8$)$_2$NC(O)—, R$^8_2$N—C(NR$^8$)—, CN, R$^8$C(O)—, N$_3$, —N(R$^8$)$_2$, and R$^9$OC(O)—NR$^8$—;

R$^4$ is independently selected from:
 a) hydrogen,
 b) aryl, substituted aryl, heterocycle, substituted heterocycle, C$_1$–C$_6$ alkyl, C$_2$–C$_6$ alkenyl, C$_2$–C$_6$ alkynyl, C$_1$–C$_6$ perfluoroalkyl, F, Cl, R$^8$O—, R$^8$C(O)NR$^8$—, CN, NO$_2$, (R$^8$)$_2$N—C(NR$^8$)—, R$^8$C(O)—, —N(R$^8$)$_2$, or R$^9$OC(O)NR$^8$—, and
 c) C$_1$–C$_6$ alkyl substituted by C$_1$–C$_6$ perfluoroalkyl, R$^8$O—, R$^8$C(O)NR$^8$—, (R$^8$)$_2$N—C(NR$^8$)—, R$^8$C(O)—, —N(R$^8$)$_2$, or R$^9$OC(O)NR$^8$—;

R$^{5a}$ and R$^{5b}$ are independently hydrogen, ethyl, cyclopropyl or methyl; R$^6$ and R$^7$ are independently selected from:
 H; C$_{1-4}$ alkyl, C$_{3-6}$ cycloalkyl, aryl, heterocycle, unsubstituted or substituted with one or two:
 a) C$_{1-4}$ alkoxy,
 b) halogen, or
 c) substituted or unsubstituted aryl or substituted or unsubstituted heterocycle;

R$^8$ is independently selected from hydrogen, C$_1$–C$_6$ alkyl, 2,2,2-trifluoroethyl, benzyl and aryl;

R$^9$ is independently selected from C$_1$–C$_6$ alkyl and aryl;

X is a bond, —S(O)$_m$—, O or —C(=O)—;

n is 0 or 1;

m is 0, 1 or 2;

p is 0, 1, 2, 3 or 4, provided that p is not 0 if X is a bond or O;

q is 0, 1 or 2, provided that q is not 0 or 1 if X is O;

r is 1 or 2; and u is independently 0 or 1;

or an optical isomer or pharmaceutically acceptable salt thereof.

In a further embodiment of this invention, the inhibitors of farnesyl-protein transferase are illustrated by the formula F:

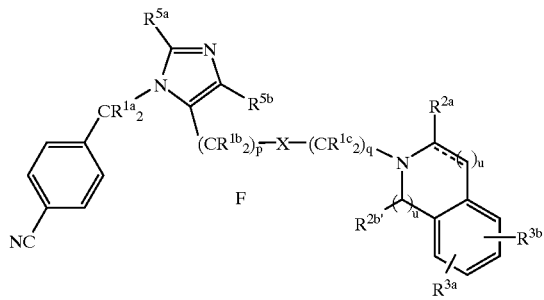

wherein:

R$^{1a}$ and R$^{1c}$ are independently selected from: hydrogen, C$_3$–C$_{10}$ cycloalkyl or C$_1$–C$_6$ alkyl;

R$^{1b}$ is independently selected from:
 a) hydrogen,
 b) aryl, heterocycle, C$_3$–C$_{10}$ cycloalkyl, R$^8$O—, —N(R$^8$)$_2$ or F,
 c) C$_1$–C$_6$ alkyl unsubstituted or substituted by aryl, heterocycle, C$_3$–C$_{10}$ cycloalkyl, R$^8$O—, or —N(R$^8$)$_2$;

R$^{2a}$ and R$^{2b}$ are independently selected from selected from: H; C$_1$–C$_6$ alkyl,

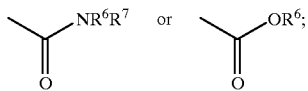

R$^{3a}$ and R$^{3b}$ are independently selected from:
a) hydrogen,
b) unsubstituted or substituted aryl, unsubstituted or substituted heterocycle, unsubstituted or substituted C$_3$–C$_{10}$ cycloalkyl, unsubstituted or substituted C$_2$–C$_6$ alkenyl, C$_2$–C$_6$ alkynyl, halogen, C$_1$–C$_6$ perfluoroalkyl, R$^9$O—, R$^9$S(O)$_m$—, R$^8$C(O)NR$^8$—, (R$^8$)$_2$NC(O)—, R$^9$C(O)O—, R$^8{}_2$N—C(NR$^8$)—, CN, NO$_2$, R$^8$C(O)—, N$_3$, —N(R$^8$)$_2$, or R$^9$OC(O)NR$^8$—,
c) unsubstituted C$_1$–C$_6$ alkyl,
d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^9$O—, R$^9$S(O)$_m$—, R$^8$C(O)NR$^8$—, (R$^8$)$_2$NC(O)—, R$^8{}_2$N—C(NR$^8$)—, CN, R$^8$C(O)—, N$_3$, —N(R$^8$)$_2$, and R$^9$OC(O)—NR$^8$—;

R$^{5a}$ and R$^{5b}$ are independently hydrogen, ethyl, cyclopropyl or methyl;

R$^6$ and R$^7$ are independently selected from:
H; C$_{1-4}$ alkyl, C$_{3-6}$ cycloalkyl, aryl, heterocycle, unsubstituted or substituted with one or two:
a) C$_{1-4}$ alkoxy,
b) halogen, or
c) substituted or unsubstituted aryl or substituted or unsubstituted heterocycle;

R$^8$ is independently selected from hydrogen, C$_1$–C$_6$ alkyl, 2,2,2-trifluoroethyl, benzyl and aryl;

R$^9$ is independently selected from C$_1$–C$_6$ alkyl and aryl;

X is a bond, —S(O)$_m$—, O or —C(=O)—;

m is 0, 1 or 2;

p is 0, 1, 2, 3 or 4;

q is 0, 1 or 2, provided that q is not 0 or 1 if X is O; and u is independently 0 or 1;

or an optical isomer or pharmaceutically acceptable salt thereof.

In a further embodiment of this invention, the inhibitors of farnesyl-protein transferase are illustrated by the formula G:

R$^{1b}$ is independently selected from:
a) hydrogen,
b) aryl, heterocycle or C$_3$–C$_{10}$ cycloalkyl,
c) C$_1$–C$_6$ alkyl unsubstituted or substituted by aryl, heterocycle, C$_3$–C$_{10}$ cycloalkyl, C$_2$–C$_6$ alkenyl, R$^8$O—, or —N(R$^8$)$_2$;

R$^{2a}$ and R$^{2b}$ are independently selected from selected from: H; C$_1$–C$_6$ alkyl,

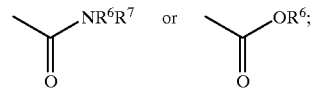

R$^{3a}$ and R$^{3b}$ are independently selected from:
a) hydrogen,
b) unsubstituted or substituted aryl, unsubstituted or substituted heterocycle, unsubstituted or substituted C$_3$–C$_{10}$ cycloalkyl, unsubstituted or substituted C$_2$–C$_6$ alkenyl, C$_2$–C$_6$ alkynyl, halogen, C$_1$–C$_6$ perfluoroalkyl, R$^9$O—, R$^9$S(O)$_m$—, R$^8$C(O)NR$^8$—, (R$^8$)$_2$NC(O)—, R$^9$C(O)O—, R$^8{}_2$N—C(NR$^8$)—, CN, NO$_2$, R$^8$C(O)—, N$_3$, —N(R$^8$)$_2$, or R$^9$OC(O)NR$^8$—,
c) unsubstituted C$_1$–C$_6$ alkyl,
d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^9$O—, R$^9$S(O)$_m$—, R$^8$C(O)NR$^8$—, (R$^8$)$_2$NC(O)—, R$^8{}_2$N—C(NR$^8$)—, CN, R$^8$C(O)—, N$_3$, —N(R$^8$)$_2$, and R$^9$OC(O)—NR$^8$—;

R$^{5a}$ and R$^{5b}$ are independently hydrogen, ethyl, cyclopropyl or methyl;

R$^6$ and R$^7$ are independently selected from:
H; C$_{1-4}$ alkyl, C$_{3-6}$ cycloalkyl, aryl, heterocycle, unsubstituted or substituted with one or two:
a) C$_{1-4}$ alkoxy,
b) halogen, or
c) substituted or unsubstituted aryl or substituted or unsubstituted heterocycle;

R$^8$ is independently selected from hydrogen, C$_1$–C$_6$ alkyl, 2,2,2-trifluoroethyl, benzyl and aryl;

R$^9$ is independently selected from C$_1$–C$_6$ alkyl and aryl;

A$^1$ is selected from: a bond, —C(O)—, O, —N(R$^8$)—, or —S(O)$_m$;

X is a bond, —S(O)$_m$—, O or —C(=O)—;

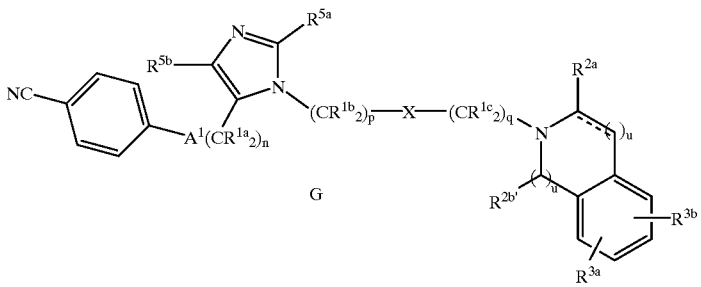

wherein:

R$^{1a}$ and R$^{1c}$ are independently selected from: hydrogen, R$^8$O—, —N(R$^8$)$_2$, F, C$_3$–C$_{10}$ cycloalkyl or C$_1$–C$_6$ alkyl;

m is 0, 1 or 2;

n is 0, 1 or 2; provided that n is not 0 if A$^1$ is a bond, O, —N(R$^8$)—, or S(O)$_m$;

p is 1, 2 or 3;

q is 0, 1 or 2, provided that q is not 0 or 1 if X is O; and u is independently 0 or 1;
or an optical isomer or pharmaceutically acceptable salt thereof.

The preferred compounds of this invention are as follows:

7-Bromo-2-(1-(4-cyanobenzyl)-5-imidazolylmethyl)-1,2,3,4-tetrahydroisoquinoline
2-(1-(4-Cyanobenzyl)-5-imidazolylmethyl)-1,2,3,4-tetrahydroisoquinoline
5,7-Dichloro-2-(1-(4-cyanobenzyl)-5-imidazolylmethyl)-1,2,3,4-tetrahydroisoquinoline
3(S)-Carboethoxy-2-(1-(4-cyanobenzyl)-5-imidazolylmethyl)-1,2,3,4-tetrahydroisoquinoline
3(R)-Carboethoxy-2-(1-(4-cyanobenzyl)-5-imidazolylmethyl)-1,2,3,4-tetrahydroisoquinoline
7-Nitro-2-(1-(4-cyanobenzyl)-5-imidazolylmethyl)-1,2,3,4-tetrahydroisoquinoline
7-Amino-2-(1-(4-cyanobenzyl)-5-imidazolylmethyl)-1,2,3,4-tetrahydroisoquinoline tris
7-Acetamido-2-(1-(4-cyanobenzyl)-5-imidazolylmethyl)-1,2,3,4-tetrahydroisoquinoline
7-Iodo-2-(1-(4-cyanobenzyl)-5-imidazolylmethyl)-1,2,3,4-tetrahydroisoquinoline
5-Bromo-2-(1-(4-cyanobenzyl)-5-imidazolylmethyl)-1,2,3,4-tetrahydroisoquinoline
5-(2,4-Dichlorophenyl)-2-(1-(4-cyanobenzyl)-5-imidazolylmethyl)-1,2,3,4-tetrahydroisoquinoline
5-(4-Cyanobenzyl)-2-(1-(4-cyanobenzyl)-5-imidazolylmethyl)-1,2,3,4-tetrahydroisoquinoline
5-(2-(3-Tolyl)vinyl)-2-(1-(4-cyanobenzyl)-5-imidazolylmethyl)-1,2,3,4-tetrahydroisoquinoline
5-(2-(3-Tolyl)ethyl)-2-(1-(4-cyanobenzyl)-5-imidazolylmethyl)-1,2,3,4-tetrahydroisoquinoline
7-Phenyl-2-(1-(4-cyanobenzyl)-5-imidazolylmethyl)-1,2,3,4-tetrahydroisoquinoline
7-(2-Tolyl)-2-(1-(4-cyanobenzyl)-5-imidazolylmethyl)-1,2,3,4-tetrahydroisoquinoline
N-(2,3-Dimethylphenyl)-2-(1-(4-cyanobenzyl)-5-imidazolylmethyl)-1,2,3,4-tetrahydroisoquinoline-3(S)-carboxamide
N-(3-Chlorobenzyl) 2-(1-(4-cyanobenzyl)-5-imidazolylmethyl)-1,2,3,4-tetrahydroisoquinoline-3(S)-carboxamide
N-(3-Chlorobenzyl),N-methyl 2-(1-(4-cyanobenzyl)-5-imidazolylmethyl)-1,2,3,4-tetrahydroisoquinoline-3(S)-carboxamide
N-(2,3-Dimethylphenyl)-2-(1-(4-cyanobenzyl)-5-imidazolylmethyl)-1,2,3,4-tetrahydroisoquinoline-3(R)-carboxamide
3(S)-Carboethoxy-7-phenyl-2-(1-(4-cyanobenzyl)-5-imidazolylmethyl)-1,2,3,4-tetrahydroisoquinoline
3(S)-Carboxylic acid-7-phenyl-2-(1-(4-cyanobenzyl)-5-imidazolylmethyl)-1,2,3,4-tetrahydroisoquinoline
N-(3-chlorobenzyl) 7-phenyl-2-(1-(4-cyanobenzyl)-5-imidazolylmethyl)-1,2,3,4-tetrahydroisoquinoline-3(s)-carboxamide
3(S)-Hydroxymethyl-7-phenyl-2-(1-(4-cyanobenzyl)-5-imidazolylmethyl)-1,2,3,4-tetrahydroisoquinoline
1(R,S)-n-Butyl-7-bromo-2-(1-(4-cyanobenzyl)-5-imidazolylmethyl)-1,2,3,4-tetrahydroisoquinoline
1-(1-(4-Cyanobenzyl)-5-imidazolylmethyl)indole
5-Bromo-1-(1-(4-cyanobenzyl)-5-imidazolylmethyl)indole
4-Bromo-1-(1-(4-cyanobenzyl)-5-imidazolylmethyl)indole
4-Phenyl-1-(1-(4-cyanobenzyl)-5-imidazolylmethyl)indole
4-(2-Methylphenyl)-1-(1-(4-cyanobenzyl)-5-imidazolylmethyl)indole
6-Bromo-2-(1-(4-cyanobenzyl)-5-imidazolylmethyl)-3,4-dihydro-1(1H)-isoquinolinone
6-Bromo-2-(1-(4-cyanobenzyl)-5-imidazolylmethyl)-1,2,3,4-tetrahydroisoquinoline
7-Bromo-2-(1-(4-cyanobenzyl)-5-imidazolylacetyl)-1,2,3,4-tetrahydroisoquinoline
5-Chloro-2-carboethoxy-1-(1-(4-cyanobenzyl)-5-imidazolylmethyl)indole
1-(4-cyanobenzyl)-5-(1-indolinylmethyl)imidazole
1-(4-cyanobenzyl)-5-(1-indazolylmethyl)imidazole
1-(4-cyanobenzyl)-5-(1-tetrahydroquinolinylmethyl)imidazole
5-(1-benzotriazolylmethyl)-1-(4-cyanobenzyl)imidazole
5-(1-benzoimidazolylmethyl)-1-(4-cyanobenzyl)imidazole
5-[1-(7-azaindolyl)methyl]-1-(4-cyanobenzyl)imidazole
5-[1-(4-azabenzimidazolyl)methyl]-1-(4-cyanobenzyl)imidazole
1-(4-cyanobenzyl)-5-(2-tetrahydroisoquinolinylmethyl)imidazole
5-(2-benzotriazolylmethyl)-1-(4-cyanobenzyl)imidazole
1-(4-cyanobenzyl)-5-(1-isatinylmethyl)imidazole
5-[1-(5-azabenzimidazolyl)methyl]-1-(4-cyanobenzyl)imidazole
5-[3-(5-azabenzimidazolyl)methyl]-1-(4-cyanobenzyl)imidazole
4-{5-[4-(3-Bromophenyl)-4,5,6,7-tetrahydroimidazo[4,5-c]pyridin-1-ylmethyl]imidazol-1-ylmethyl}benzonitrile
6,7-Dimethoxy-2-(1-(4-cyanobenzyl)-5-imidazolylmethyl)1,2,3,4-tetrahydroisoquinoline
1(R,S)-(2-Phenethyl)-6-methoxy-2-(1-(4-cyanobenzyl)-5-imidazolylmethyl)-1,2,3,4-tetrahydroisoquinoline
1-(4-Cyanobenzyl)-5-(2-amino-1-benzimidazolylmethyl)imidazole
1-(4'-cyanobenzyl)-5-(2-amino-1-(3-benzyl-2-imino-1-benzimidazolylmethyl)imidazole or an optical isomer or a pharmaceutically acceptable salt thereof.

Specific examples of the compounds of the invention are:

3(R)-Carboethoxy-2-(1-(4-cyanobenzyl)-5-imidazolylmethyl)-1,2,3,4-tetrahydroisoquinoline 7-Phenyl-2-(1-(4-cyanobenzyl)-5-imidazolylmethyl)-1,2,3,4-tetrahydroisoquinoline N-(3-Chlorobenzyl) 2-(1-(4-cyanobenzyl)-5-imidazolylmethyl)-1,2,3,4-tetrahydroisoquinoline-3(S)-carboxamide

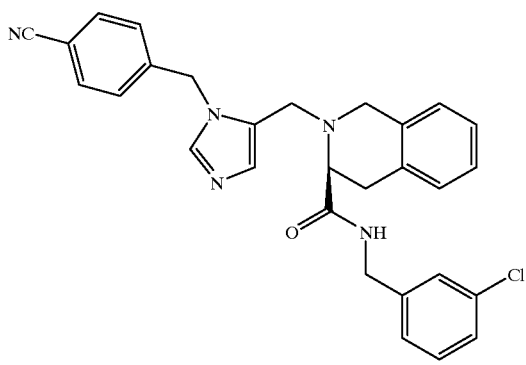

1(R,S)-n-Butyl-7-bromo-2-(1-(4-cyanobenzyl)-5-imidazolylmethyl)-1,2,3,4-tetrahydroisoquinoline

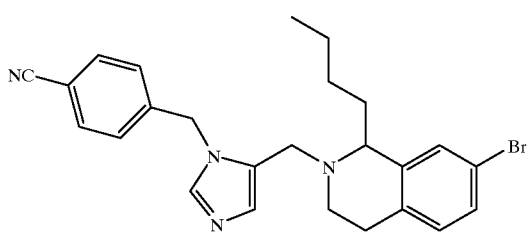

1-(1-(4-Cyanobenzyl)-5-imidazolylmethyl)indole

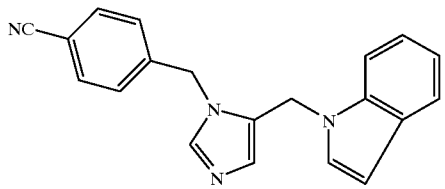

1-(4-cyanobenzyl)-5-(1-indolinylmethyl)imidazole

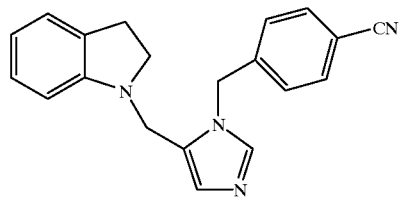

1-(4-cyanobenzyl)-5-(1-indazolylmethyl)imidazole

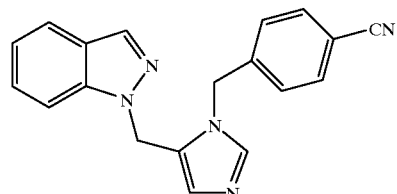

1-(4-cyanobenzyl)-5-(1-tetrahydroquinolinylmethyl)imidazole

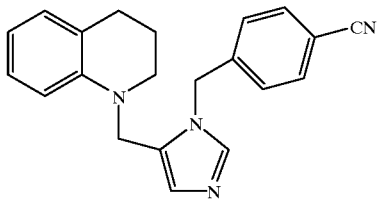

5-(1-benzoimidazolylmethyl)-1-(4-cyanobenzyl)imidazole

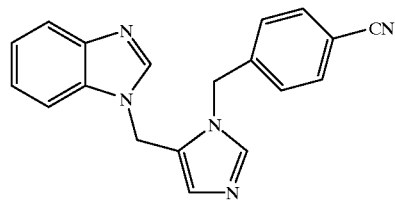

1-(4-cyanobenzyl)-5-(2-tetrahydroisoquinolinylmethyl)imidazole

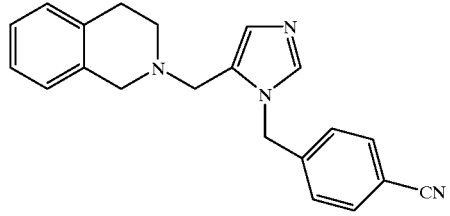

6,7-Dimethoxy-2-(1-(4-cyanobenzyl)-5-imidazolylmethyl)1,2,3,4-tetrahydroisoquinoline

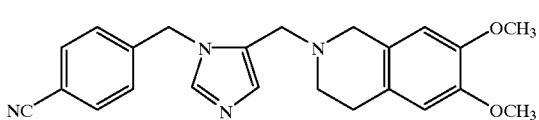

1-(4-Cyanobenzyl)-5-(2-amino-1-(3-benzyl-2-imino-1-benzimidazolylmethyl)imidazole

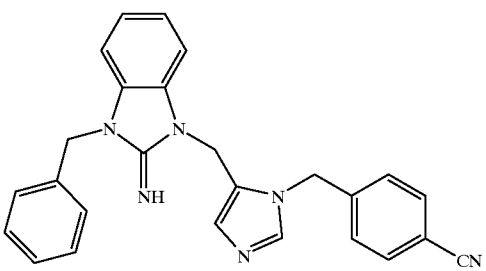

or an optical isomer or a pharmaceutically acceptable salt thereof.

The compounds of the present invention may have asymmetric centers and occur as racemates, racemic mixtures, and as individual diastereomers, with all possible isomers, including optical isomers, being included in the present invention. When any variable (e.g. aryl, heterocycle, $R^{1a}$, $R^4$ etc.) occurs more than one time in any constituent, its definition on each occurence is independent at every other occurence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

As used herein, "aryl" is intended to mean any stable monocyclic, bicyclic or tricyclic carbon ring of up to 7 members in each ring, wherein at least one ring is aromatic. Examples of monocyclic and bicyclic aryl elements include phenyl, naphthyl, tetrahydronaphthyl, indanyl, biphenyl, phenanthryl, anthryl or acenaphthyl. Examples of tricyclic aryl elements include 10,11-dihydro-5H-dibenzo[a,d] cyclohepten-5-yl (which is also known as dibenzylsuberyl), 9-fluorenyl and 9,10-dihydroanthracen-9-yl. Preferably, "aryl" is a monocyclic or bicyclic carbon ring.

The term heterocycle or heterocyclic, as used herein, represents a stable 5- to 7-membered monocyclic or stable 8- to 11-membered bicyclic heterocyclic ring or stable 13- to 15-membered tricyclic heterocyclic ring, which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of monocyclic and bicyclic heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopyrrolidinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. Examples of tricyclic heterocyclic elements include, but are not limited to, 6,11-dihydro-5H-benzo[5,6]cyclohepta[1,2-b]pyridine, 9,10-dihydro-4H-3-thia-benzo[f]azulen-4-yl and 9-xanthenyl. The 6,11-dihydro-5H-benzo[5,6]cyclohepta[1,2-b]pyridine moiety has the following structure:

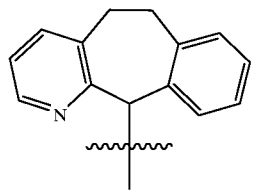

Preferably, "heterocyclic" is a monocyclic or bicyclic moiety.

As used herein, "heteroaryl" is intended to mean any stable monocyclic, bicyclic or tricyclic carbon ring of up to 7 members in each ring, wherein at least one ring is aromatic and wherein from one to four carbon atoms are replaced by heteroatoms selected from the group consisting of N, O, and S. Examples of monocyclic and bicyclic heteroaryl elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl. Examples of tricyclic heteroaryl elements include, but are not limited to, 6,11-dihydro-5H-benzo[5,6]cyclohepta[1,2-b]pyridine. Preferably, "heteroaryl" is a monocyclic or bicyclic moiety.

As used herein, the terms "substituted aryl", "substituted heterocycle" and "substituted cycloalkyl" are intended to include the cyclic group containing from 1 to 3 substitutents in addition to the point of attachment to the rest of the compound. Such substitutents are preferably selected from the group which includes but is not limited to F, Cl, Br, $CF_3$, $NH_2$, $N(C_1-C_6 \text{ alkyl})_2$, $NO_2$, CN, $(C_1-C_6 \text{ alkyl})O$—, —OH, $(C_1-C_6 \text{ alkyl})S(O)_m$—, $(C_1-C_6 \text{ alkyl})C(O)NH$—, $H_2N$—C(NH)—, $(C_1-C_6 \text{ alkyl})C(O)$—, $(C_1-C_6 \text{ alkyl})OC(O)$—, $N_3$, $(C_1-C_6 \text{ alkyl})OC(O)NH$— and $C_1$—$C_{20}$ alkyl.

When $R^6$ and $R^7$ or $R^7$ and $R^{7a}$ are combined to form a ring, cyclic amine moieties are formed. Examples of such cyclic moieties include, but are not limited to:

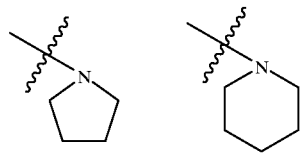

In addition, such cyclic moieties may optionally include another heteroatom(s). Examples of such heteroatom-containing cyclic amine moieties include, but are not limited to:

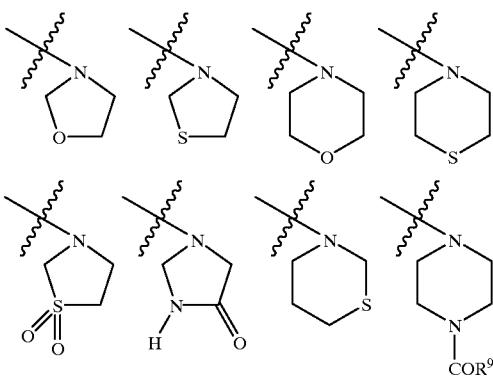

Lines drawn into the ring systems from substituents (such as from $R^2$, $R^3$, $R^4$ etc.) indicate that the indicated bond may be attached to any of the substitutable ring carbon or nitrogen atoms.

Preferably, $R^{1a}$ and $R^{1b}$ are independently selected from: hydrogen, —$N(R^8)_2$, $R^8C(O)NR^8$— or $C_1-C_6$ alkyl which is unsubstituted or substituted by —$N(R^8)_2$, $R^8O$— or $R^8C(O)NR^8$—.

Preferably, $R^{2a}$ is selected from: H;

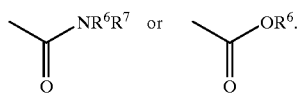

Preferably, $R^{2b'}$ and $R^{2b''}$ are independently selected from selected from: H or $C_1$–$C_6$ alkyl.

Preferably, $R^{3a}$ and $R^{3b}$ are independently selected from: hydrogen, $C_1$–$C_6$ perfluoroalkyl, F, Cl, Br, $R^8O$—, $R^9S(O)_m$—, CN, $R^8C(O)$—, —$N(R^8)_2$ and $C_1$–$C_6$ alkyl.

Preferably, $R^4$ is selected from: hydrogen, perfluoroalkyl, F, Cl, Br, $R^8O$—, $R^9S(O)_m$—, CN, $NO_2$, $R^8{}_2N$—$C(NR^8)$—, $R^8C(O)$—, $N_3$, —$N(R^8)_2$, $R^9OC(O)NR^8$— and $C_1$–$C_6$ alkyl.

Preferably, $R^5$ is hydrogen or $C_1$–$C_6$ alkyl.

Preferably, $R^8$ is selected from H, $C_1$–$C_6$ alkyl and benzyl.

Preferably, $A^1$ and $A^2$ are independently selected from: a bond, —$C(O)NR^8$—, —$NR^8C(O)$—, O, —$N(R^8)$—, —$S(O)_2N(R^8)$— and —$N(R^8)S(O)_2$—.

Preferably, V is selected from hydrogen, heterocycle and aryl.

Preferably, W is imidazolyl.

Preferably, X is a bond or (C=O)—.

Preferably, n, p and r are independently 0, 1, or 2. More preferably, r is 1.

Preferably t is 1.

Preferably u is independently 0 or 1. Most preferably, u is 1.

Preferably, the moiety

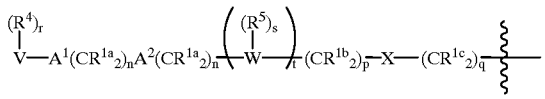

is selected from:

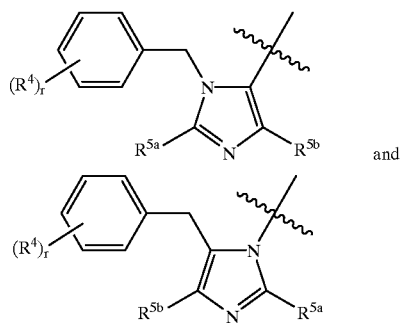

and

The pharmnaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^{1a}$, Z, n, etc.) at a particular location in a molecule be independent of its definitions elsewhere in that molecule. Thus, —$N(R^8)_2$ represents —$NH_2$, —$NHCH_3$, —$NHC_2H_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Abbreviations used in the description of the chemistry and in the Examples that follow are:

| | |
|---|---|
| $Ac_2O$ | Acetic anhydride; |
| Boc | t-Butoxycarbonyl; |
| CBz | Carbobenzyloxy; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethylformamide; |
| EDC | 1-(3-dimethylaminopropyl)-3-ethyl-carbodiimide-hydrochloride; |
| $Et_3N$ | Triethylene; |
| EtOAc | Ethyl acetate; |
| FAB | Fast atom bombardment; |
| HOBT | 1-Hydroxybenzotriazole hydrate; |
| HOOBT | 3-Hydroxy-1,2,2-benzotriazin-4(3H)-one; |
| HPLC | High-performance liquid chromatography; |
| MCPBA | m-Chloroperoxybenzoic acid; |
| MsCl | Methanesulfonyl chloride; |
| NaHMDS | Sodium bis(trimethylsilyl)amide; |
| Py | Pyridine; |
| TFA | Trifluoroacetic acid; |
| THF | Tetrahydrofuran. |

The compounds of this invention are prepared by employing reactions as shown in the Schemes 1–16, in addition to other standard manipulations such as ester hydrolysis, cleavage of protecting groups, etc., as may be known in the literature or exemplified in the experimental procedures. While stereochemistry is shown in the Schemes, a person of ordinary skill in the art would understand that the illustrated compounds represent racemic mix tures which may be separated at a subsequent purification step or may be utilized as the racemic mixture.

These reactions may be employed in a linear sequence to provide the compounds of the invention or they may be used to synthesize fragments which are subsequently joined by the reductive alkylation or acylation reactions described in the Schemes .

Synopsis of Schemes 1–7:

The requisite intermediates are in some cases commercially available, or can be prepared according to literature procedures, for the most part. For example, see M. Cain et al., *Heterocycles*, 19:1003 (1982), V. Schollkopf et al., *Angew. Chem. Int. Ed. Engl.*, 26:143(1987), Huber and Seebach, *Helvitica Chim. Acta*, 70:1944 (1987), and J. L. Stanton et al., *J. Med. Chem.*, 26:1267 (1983).

In Schemes 1–2, for example, the syntheses of 1,2,3,4-tetrahydroisoquinoline intermediates are outlined. The subsequent reactions described in the remaining schemes may be similarly applied to suitably protected commercially available tetrahydroisoquinolines, as well as commercially or synthetically obtained homologs, to provide compounds of the instant invention.

Scheme 1 Illustrates the synthesis of 1,2,3,4-tetrahydroisoquinolines essentially according to the method of Stokker in *Tetrahedron Letts.*, 1996, 37, 5453. Thus, phenethylamines such as 1 may be converted to the corresponding trifluoroacetate 2 using, for example, trifluoroacetic anhydride and an organic base such as triethylamine in a suitable solvent such as dichloromethane. Compound 2 can then be cyclized to 3 using paraformaldehyde in a strong acid milieu, for example a mixture of acetic acid and concentrated sulfuric acid. Hydrolysis of 3 using aqueous base then affords of 1,2,3,4-tetrahydroisoquinolines such as 4.

An alternative route to 1,2,3,4-tetrahydroisoquinolines such as 9 is shown in Scheme 2. This is as described by Larsen et al in *J. Org. Chem.*, 1991, 56, 6034. Amides such as 5 (obtained by standard coupling of the appropriate phenethylamine and an acid or acid derivative) may be treated with oxalyl chloride in dichloromethane to yield 6 which is then cyclized using a Lewis acid (e.g. $FeCl_3$) to give the intermediate 7. Treatment of 7 with an acid such as sulfuric acid in a polar solvent (for example methanol) results in the formation of the 3,4-dihydroisoquinoline 8. Compound 8 may also be obtained from 5 using the well-known Bischler-Napieralski reaction. Reduction of the imine of 8 to 9 may be done with a reducing agent such as sodium borohydride in an alcoholic solvent (e.g. methanol) or, alternatively, asymmetric hydrogenation processes may be employed to give 9 in optically enriched form. Intermediate 9 may be coupled with a suitably substituted acid using standard amide bond formation methods to yield the instant compound 10.

Scheme 3 illustrates reactions wherein the preferred 4-cyanobenzylimidazolyl moiety is incorporated into the instant compounds.

Schemes 4–5 illustrate the syntheses of 1,2,3,4-tetrahydroisoquinolines of the instant invention wherein the "X" moiety is other than an alkyl bridge. The reactions illustrated therein show the incorporation of sidechains which comprise the preferred 4-cyanobenzylimidazolyl moiety. It is understood that a person of ordinary skill in the art could readily modify such reaction sequences by using appropriate protecting groups and reagents well known to one skilled in the art to provide other compounds of the instant invention.

Scheme 4 illustrates the syntheses of compounds of the instant invention wherein "X" is —S—. Thus the intermediate aldehyde 11 is reduced to the alcohol 12, activated and treated with a suitable thioacetate to provide the thioester 13. The thiol is then generated and alkylated with a suitable ester containing reagent, such as bromoacetic acid to provide intermediate 14. Reduction of the ester moiety, followed by oxidation provides the corresponding aldehyde, which can be utilized to reductively alkylate the suitably substituted 1,2,3,4-tetrahydroisoquinoline to provide the instant compound 15.

Scheme 5 illustrates the syntheses of compounds of the instant invention wherein "X" is —O—. Thus, a dihydroxyalkane, such as ethylene glycol, can be selectively protected and oxidized to provide the aldehyde 16. Intermediate 16 can be utilized to reductively alkylate the suitably substituted 1,2,3,4-tetrahydroisoquinoline and the sidechain deprotected. Intermediate 17 can then be alkylated with a suitable reagent to provide the instant compound 18 which incorporates the ether moiety.

The reagent utilized in the reductive alkylation of the 1,2,3,4-tetrahydroisoquinoline may alternatively incorporate a leaving group which may subsequently react with a blocked imidazolyl reagent, such as 19 to provide compounds of the instant invention wherein "X" is a bond and the preferred imidazolyl is attached to the alkyl bridge via one of the ring nitrogens, as shown in Scheme 6.

Scheme 7 illustrates the syntheses of compounds of the instant invention comprising 3,4-dihydro-1(1H)-isoquinolinones, indoles and benzoimidazoles. Syntheses of suitably substituted indole starting materials are well known in the art and are described in "Comprehensive Heterocyclic Chemistry-Vol. 4", Chapter 3.06: Pyrroles and their Benzo Derivatives: (iii) Synthesis and Applications, R. J. Sundberg.

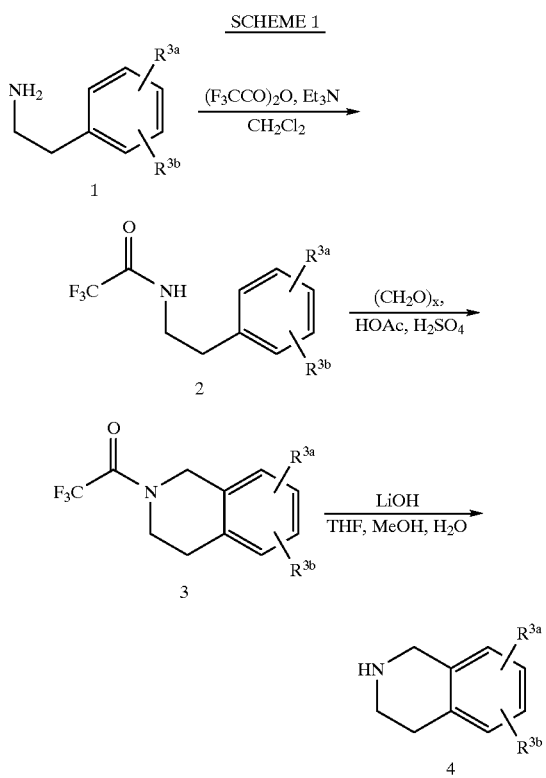

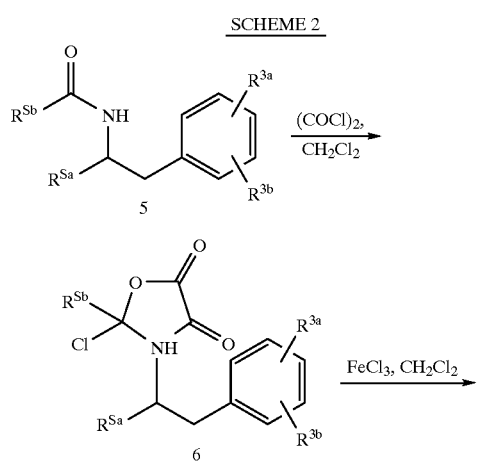

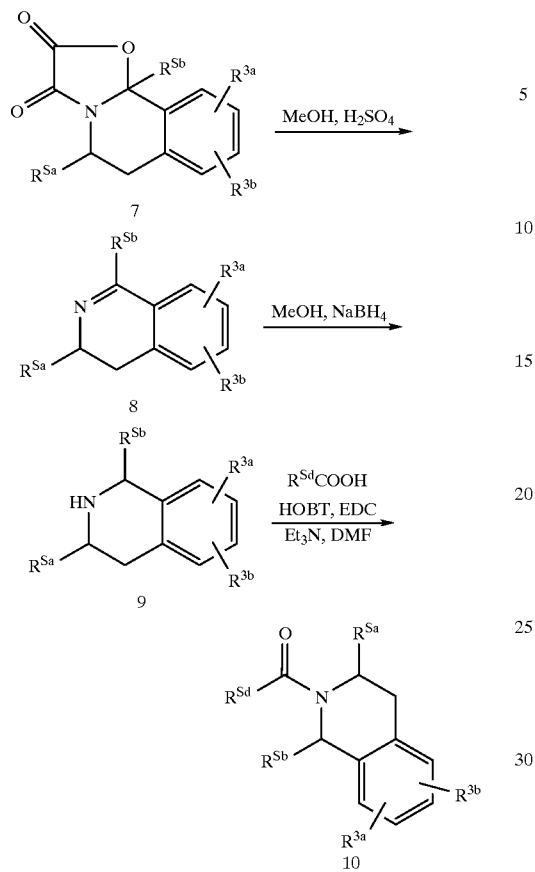
SCHEME 3
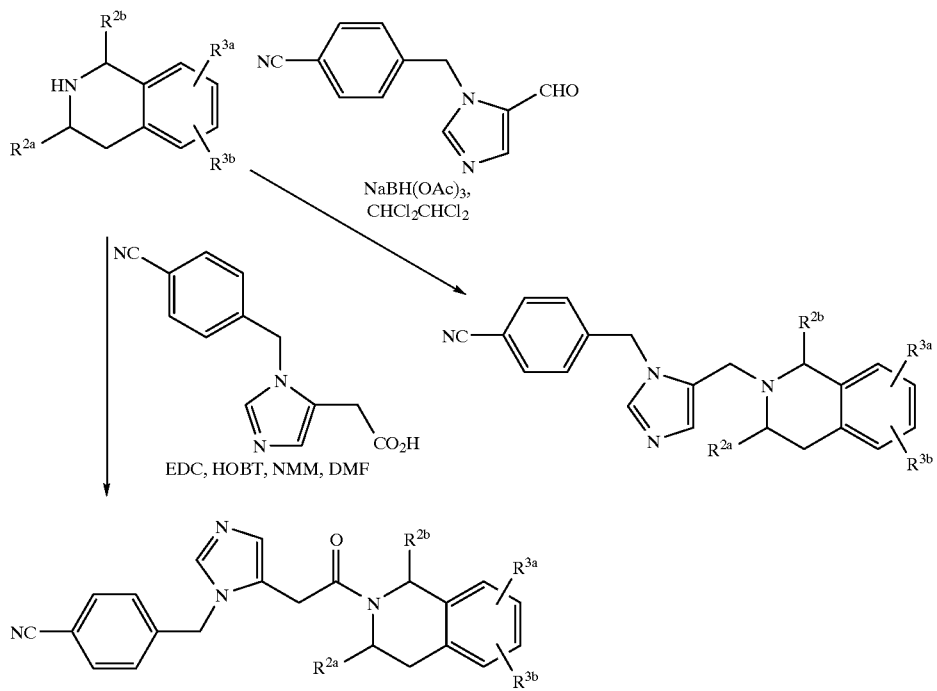

SCHEME 4
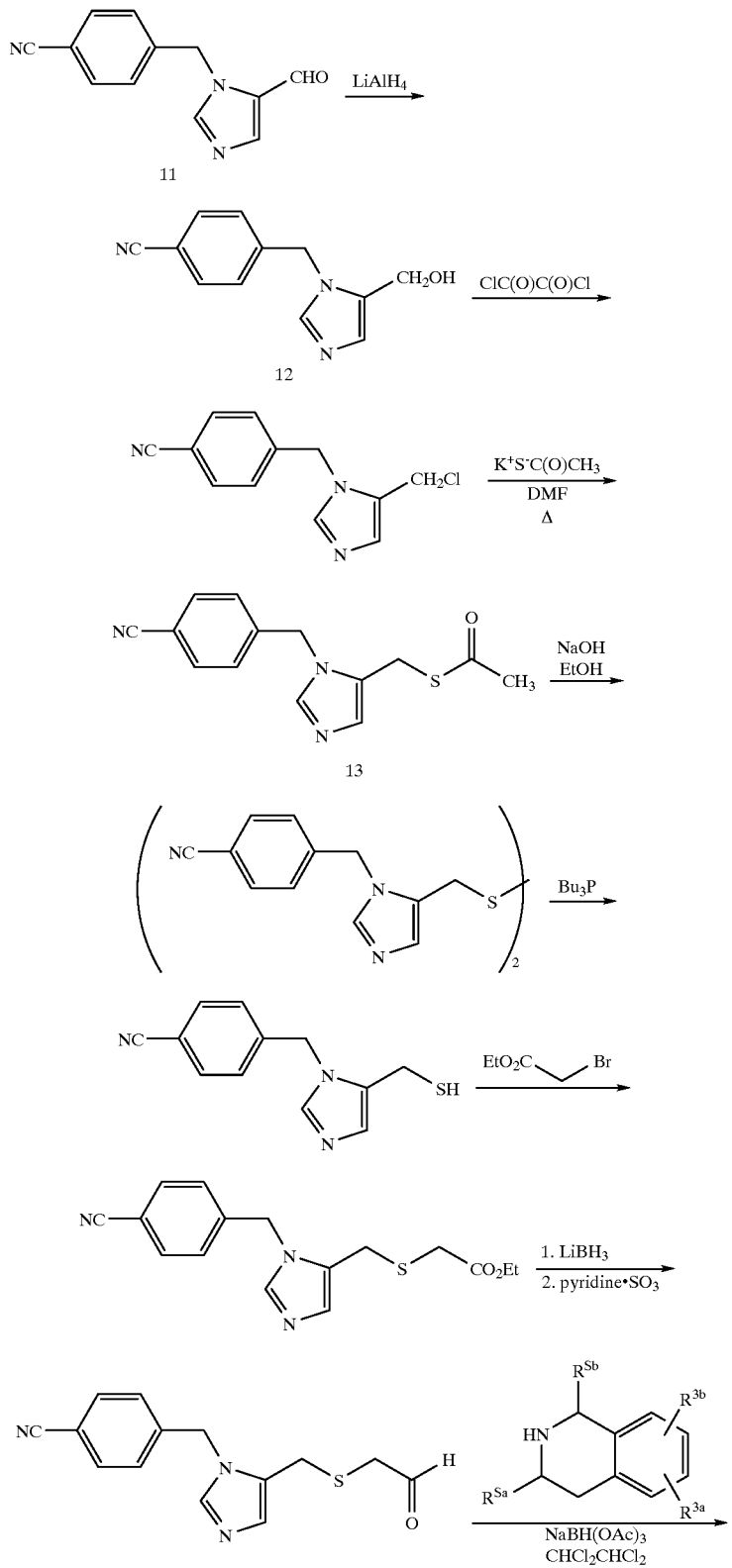

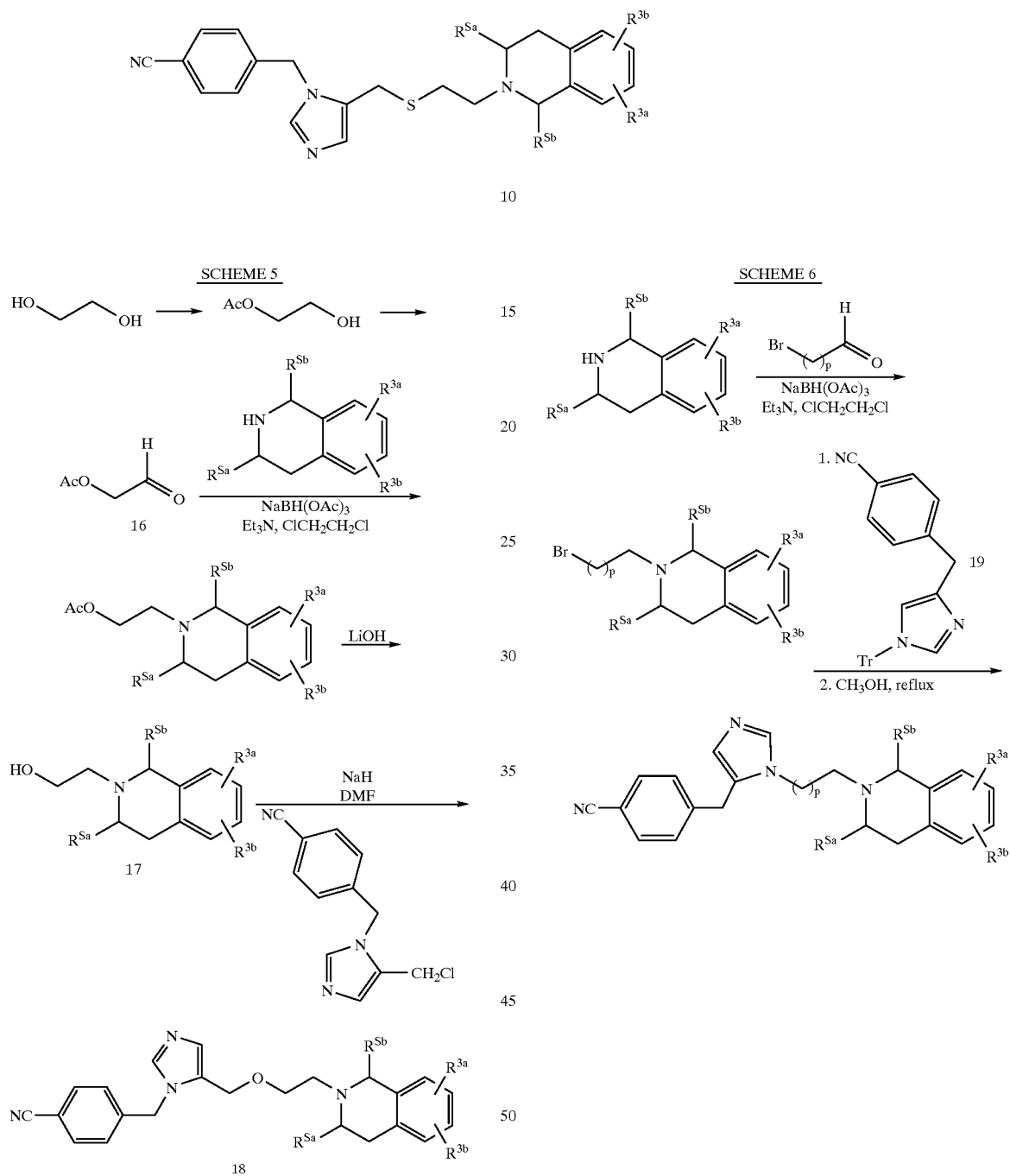

SCHEME 7

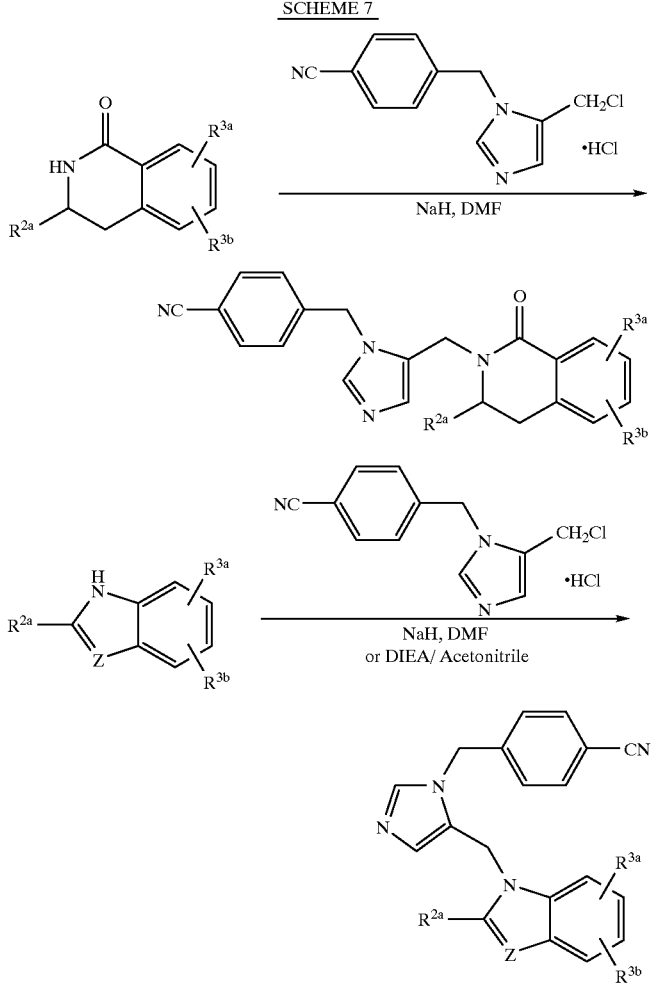

In the above Schemes it is understood that R$^{Sd}$ is

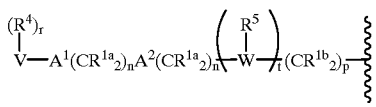

or a protected precursor thereof;
R$^{Sa}$— is R$^{2a}$ or a protected precusor thereof; and
R$^{Sb}$— is R$^{2b'}$, R$^{2b''}$ or protected precusor thereof; and
R— is a "substituted" or a protected precursor thereof.

It is understood that a variety of amines and acids, either commercially available or readily synthesized by reactions well known in the art, which contain the side-chain moieties R$^{Sa}$ and R$^{Sd}$(C=O) may be utilized in the reactions described hereinabove. Schemes 8–16 illustrate specific reactions wherein such intermediates containing the side-chain moieties R$^{Sa}$ and R$^{Sd}$(C=O) may be prepared. It is understood that while Schemes 8–16 illustrate preparation of both protected and unprotected intermediates, a person of ordinary skill would appreciate that subsequent reactions which utilize those intermediates, such as those described in Schemes 1–7, may require protection and eventual deprotection of certain intermediate moieties.

The selectively protected intermediate 20 utilized in the synthesis illustrated in Scheme 8 can be reductively alkylated with a variety of aldehydes, such as 21. The aldehydes can be prepared by standard procedures, such as that described by O. P. Goel, U. Krolls, M. Stier and S. Kesten in *Organic Syntheses*, 1988, 67, 69–75. The reductive alkylation can be accomplished at pH 5–7 with a variety of reducing agents, such as sodium triacetoxyborohydride or sodium cyanoborohydride in a solvent such as dichloroethane, methanol or dimethylformamide. The ester product 22 can be deprotected with trifluoroacetic acid in methylene chloride to give the substituted diamine 23. That diamine may be isolated in the salt form, for example, as a trifluoroacetate, hydrochloride or acetate salt, among others. The product diamine 23 can be further selectively protected and reductively alkylated with a second aldehyde to obtain an analogous tertiary amine. Alternatively, the diamine 23 can be cyclized to obtain intermediates such as the dihydroimidazole 24 by procedures known in the literature. The ester 24 can then be utilized in a reaction such as illustrated in Scheme 3 hereinabove.

Scheme 9 illustrates a general preparation of aralkyl imidazolyl intermediates 31 that can be utilized in reactions such as illustrated in Scheme 3. Thus imidazole acetic acid 27 can be converted to the protected acetate 29 by standard procedures, and 29 can be first reacted with an alkyl halide, then treated with refluxing methanol to provide the regiospecifically alkylated imidazole acetic acid ester 30. Hydrolysis provides the acetic acid 31.

Schemes 10–13 illustrate syntheses of suitably substituted alkanols useful in the syntheses of the instant compounds wherein the variable W is present as a pyridyl moiety. The hydroxyl moiety of such intermediates may be converted into the corresponding aldehyde, as illustrated in Scheme 10 or may be converted to a suitable leaving group, as illustrated in Scheme 12. Similar synthetic strategies for preparing alkanols that incorporate other heterocyclic moieties for variable W are also well known in the art.

Compounds of the instant invention wherein the $A^1(CR^{1a}_2)_nA^2(CR^{1a}_2)_n$ linker is a substituted methylene may be synthesized by the methods shown in Scheme 14. Thus, the N-protected imidazolyl iodide 32 is reacted, under Grignard conditions with a suitably protected benzaldehyde to provide the alcohol 33. Acylation, followed by the alkylation procedure illustrated in the Schemes above (in particular, Scheme 6) provides the instant compound 34. If other $R^1$ substituents are desired, the acetyl moiety can be manipulated as illustrated in the Scheme.

Scheme 15 illustrates synthesis of an instant compound wherein a non-hydrogen $R^{5b}$ is incorporated in the instant compound. Thus, a readily available 4-substituted imidazole 37 may be selectively iodinated to provide the 5-iodoimidazole 38. That imidazole may then be protected and coupled to a suitably substituted benzyl moiety to provide intermediate 39. Intermediate 39 can then undergo the alkylation reactions that were described hereinabove.

Compounds of the instant invention wherein the $A^1(CR^{1a}_2)_nA^2(CR^{1a}_2)_n$ linker is oxygen may be synthesized by methods known in the art, for example as shown in Scheme 16. The suitably substituted phenol 41 may be reacted with methyl N-(cyano)methanimidate to provide the 4-phenoxyimidazole 42. After selective protection of one of the imidazolyl nitrogens, the intermediate 43 can undergo alkylation reactions as described for the benzylimidazoles hereinabove.

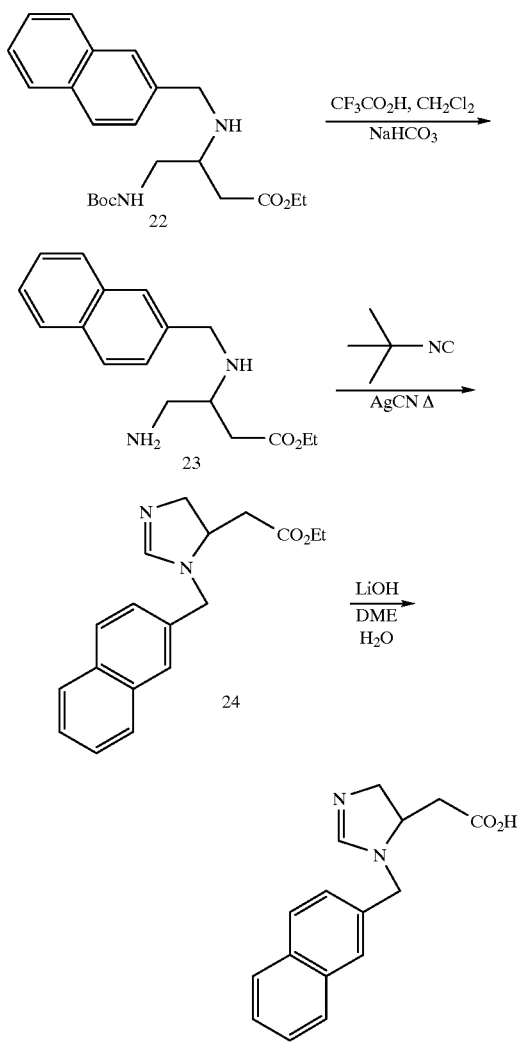

SCHEME 8

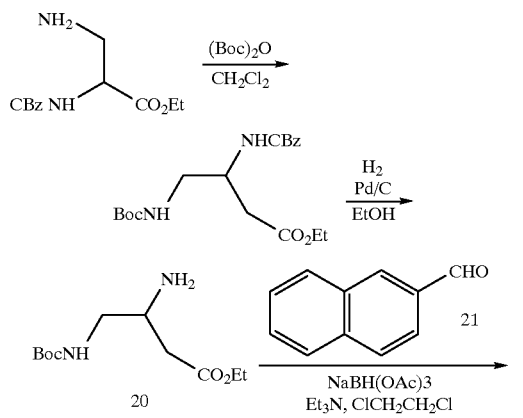

SCHEME 9

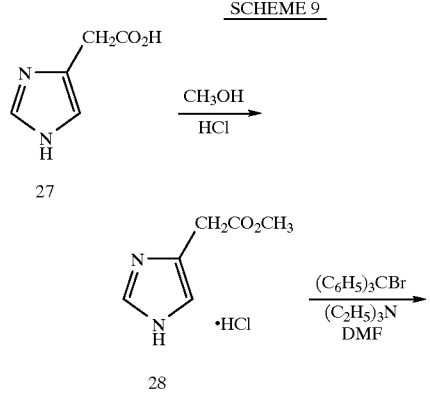

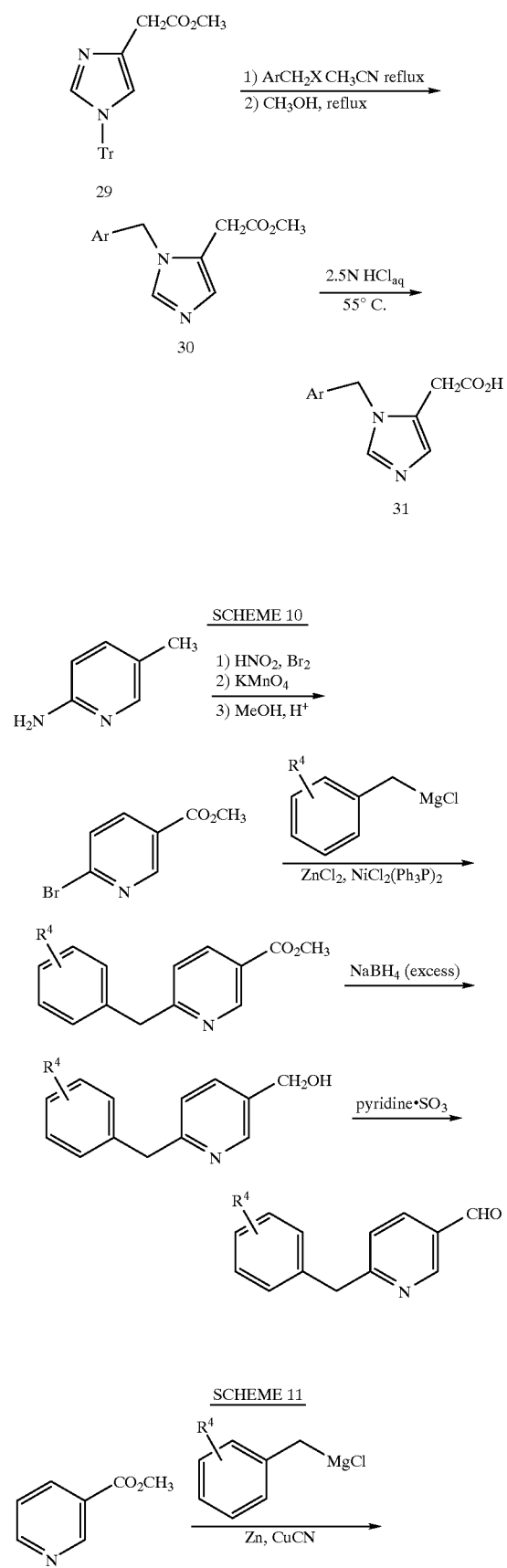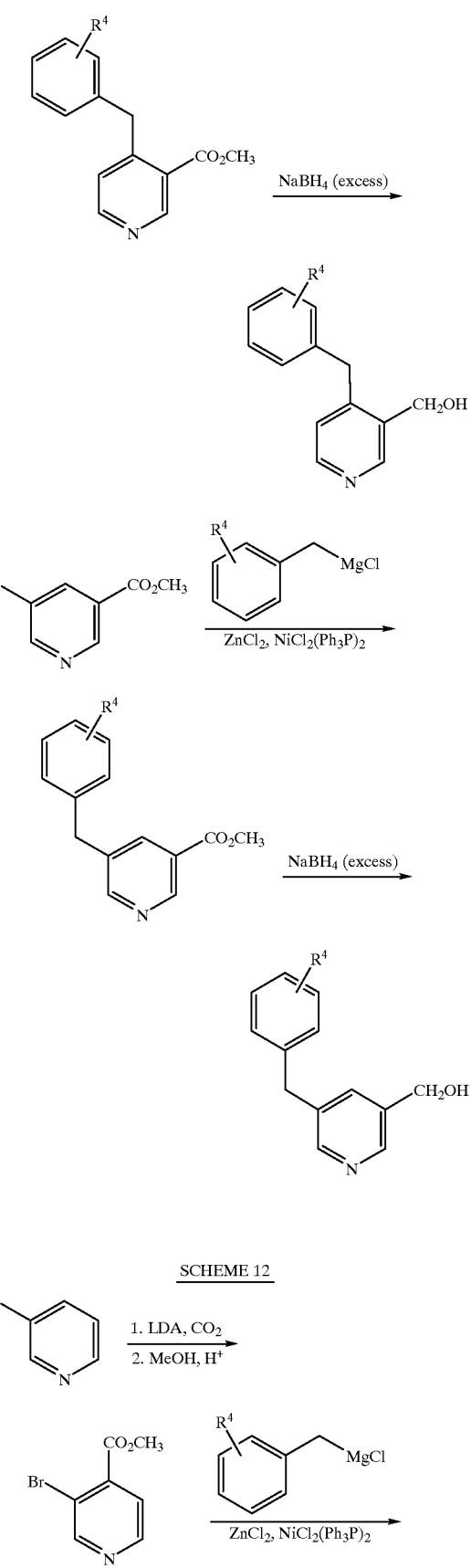

-continued
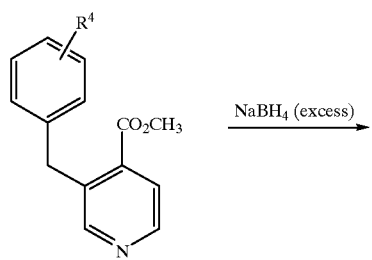
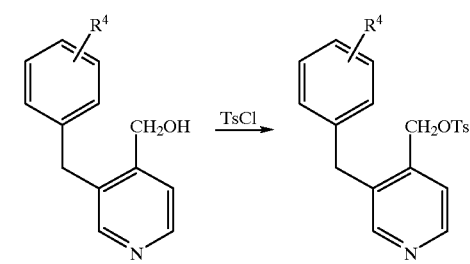
SCHEME 13
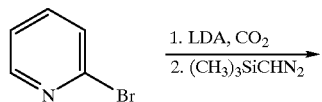
-continued
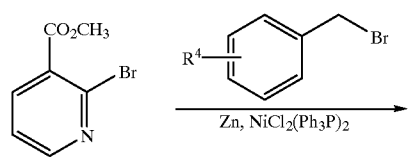
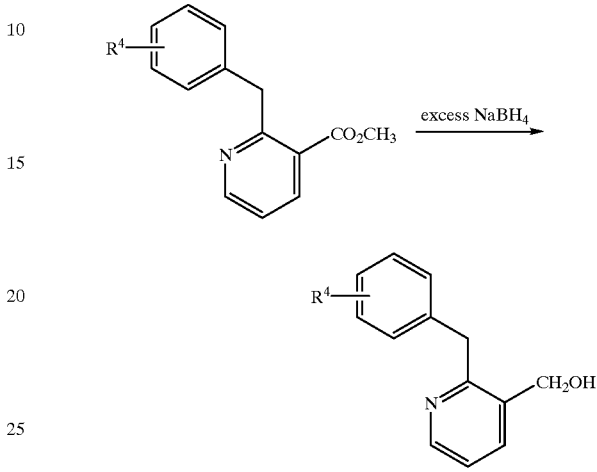
SCHEME 14
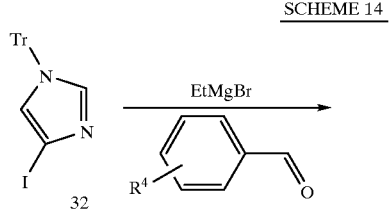
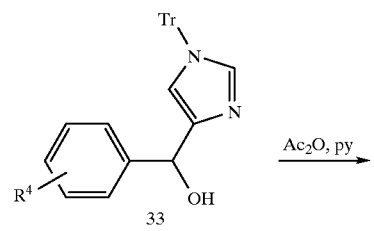
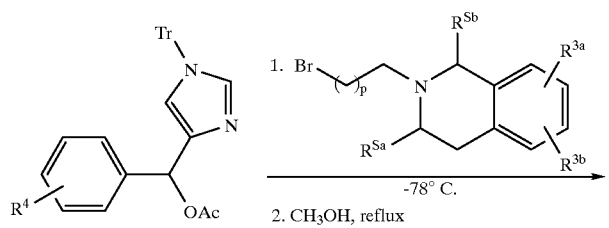

-continued
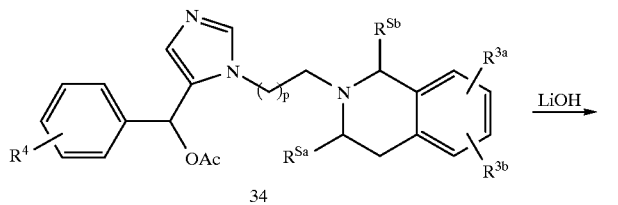
34
LiOH →
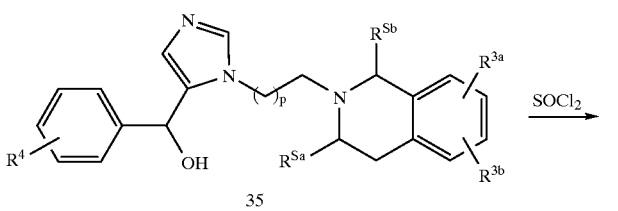
35
SOCl₂ →
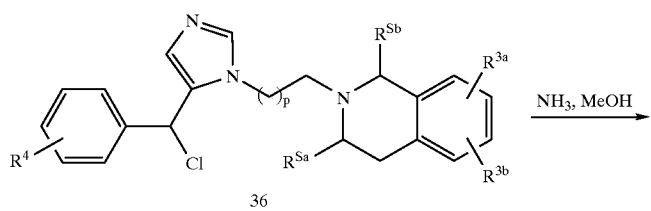
36
NH₃, MeOH →
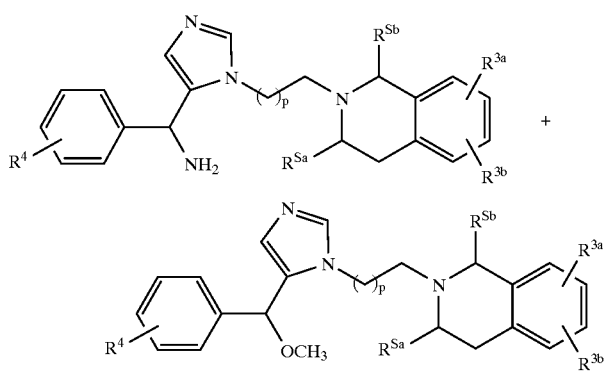
SCHEME 15
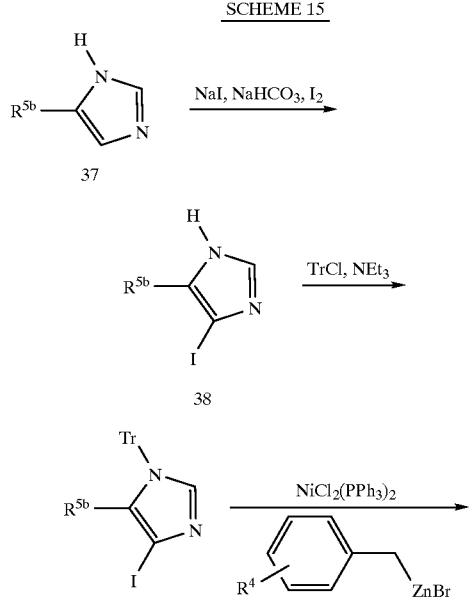
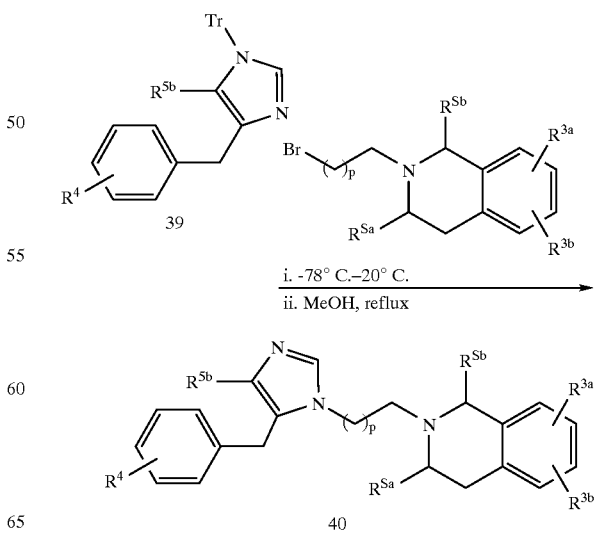

SCHEME 16

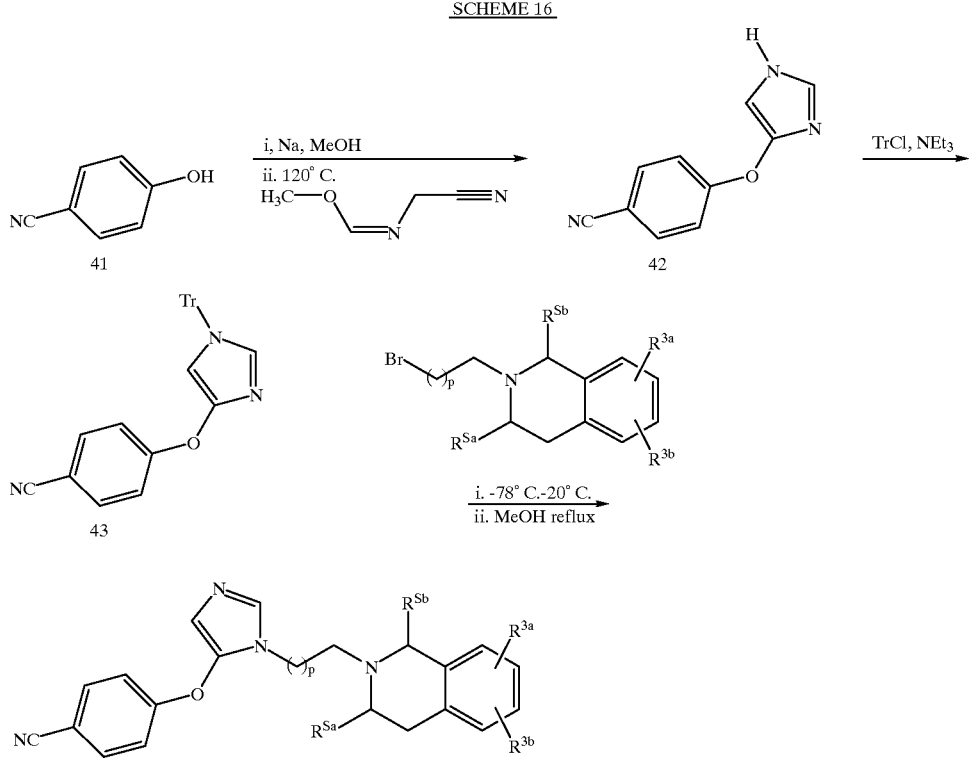

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scr, abl, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. Cancer Research, 55:4575–4580 (1995)). Such anti-angiogenesis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, the compounds are useful in the treatment of neurofibromatosis, which is a benign proliferative disorder.

The instant compounds may also be useful in the treatment of certain viral infections, in particular in the treatment of hepatitis delta and related viruses (J. S. Glenn et al. Science, 256:1331–1333 (1992).

The compounds of the instant invention are also useful in the prevention of restenosis after percutaneous transluminal coronary angioplasty by inhibiting neointimal formation (C. Indolfi et al. Nature medicine, 1:541–545(1995)).

The instant compounds may also be useful in the treatment and prevention of polycystic kidney disease (D. L. Schaffner et al. American Journal of Pathology, 142:1051–1060 (1993) and B. Cowley, Jr. et al. FASEB Journal, 2: A3160 (1988)).

The instant compounds may also be useful for the treatment of fungal infections.

In a preferred embodiment of the instant invention the compounds of this instant invention are selective inhibitors of farnesyl-protein transferase. A compound is considered a selective inhibitor of farnesyl-protein transferase, for example, when its in vitro farnesyl-protein transferase inhibitory activity, as assessed by the assay described in Example 41, is at least 100 times greater than the in vitro activity of the same compound against geranylgeranyl-protein transferase-type I in the assay described in Example 42. Preferably, a selective compound exhibits at least 1000 times greater activity against one of the enzymatic activities when comparing geranylgeranyl-protein transferase-type I inhibition and farnesyl-protein transferase inhibition.

In another preferred embodiment of the instant invention the compounds of this instant invention are dual inhibitors of farnesyl-protein transferase and geranylgeranyl-protein transferase type I. Such a dual inhibitor will exhibit certain characteristics when assessed in in vitro assays, which are dependent on the type of assay employed.

In a SEAP assay, such as described in Example 45, it is preferred that the dual inhibitor compound has an in vitro inhibitory activity ($IC_{50}$) that is less than about 12 μM against K4B-Ras dependent activation of MAP kinases in cells. More preferably, the dual inhibitor compound has an in vitro inhibitory activity ($IC_{50}$) against K4B-Ras dependent activation of MAP kinases in cells which is more than about 5 times lower than the inhibitory activity ($IC_{50}$) against Myr-Ras dependent activation of MAP kinases in cells. Also more preferably, in a SEAP assay, the dual inhibitor compound has an inhibitory activity ($IC_{50}$) that is less than about 10 nM against H-Ras dependent activation of MAP kinases in cells.

In a GGTase plus anion assay, such as described in Example 42, it is preferred that the dual inhibitor compound has an in vitro inhibitory activity ($IC_{50}$) that is less than about 5 µM against transfer of a geranylgeranyl residue to a protein or peptide substrate comprising a $CAAX^G$ motif by geranylgeranyl-protein transferase type I in the presence of a modulating anion. More preferably, the dual inhibitor compound has an in vitro inhibitory activity ($IC_{50}$) that is less than about 1 µM against transfer of a geranylgeranyl residue to a protein or peptide substrate comprising a $CAAX^G$ motif by geranylgeranyl-protein transferase type I in the presence of a modulating anion. Preferably, the dual inhibitor compound has an in vitro inhibitory activity ($IC_{50}$) in the in vitro assay as described in Example 41 that is less than about 1 µM against transfer of a farnesyl residue to a protein or peptide substrate, comprising a $CAAX^F$ motif, by farnesyl-protein transferase. more preferably, the dual inhibitor compound has an in vitro inhibitory activity ($IC_{50}$) that is less than about 100 nM against transfer of a farnesyl residue to a protein or peptide substrate, comprising a $CAAX^F$ motif, by farnesyl-protein transferase. Also preferably, the dual inhibitor compound has an in vitro inhibitory activity ($IC_{50}$) in the in vitro assay as described in Example 44, that is less than about 100 nM against the anchorage independent growth of H-ras-transformed mammalian fibroblasts.

The protein or peptide substrate utilized in the instant assay may incorporate any CAAX motif that is geranylgeranylated by GGTase-I. The term "$CAAX^G$" will refer to such motifs that may be geranylgeranylated by GGTase-I. It is understood that some of the "$CAAX^G$" containing protein or peptide substrates may also be farnesylated by farnesyl-protein transferase. In particular such "$CAAX^G$" motifs include (the corresponding human protein is in parentheses): CVIM (K4B-Ras), CVLL (mutated H-Ras), CVVM (N-Ras), CIIM (K4A-Ras), CLLL (Rap-IA), CQLL (Rap-IB), CSIM, CAIM, CKVL and CLIM (PFX). Preferably, the CAAX motif is CVIM.

As used herein, the term "$CAAX^F$" is used to designate a protein or peptide substrate that incorporates four amino acid C-terminus motif that is farnesylated by farnesyl-protein transferase. It is understood that certain of the "$CAAX^F$" containing protein or peptide substrates may also be geranylgeranylated by GGTase-I. In particular such "$CAAX^F$" motifs include (the corresponding human protein is in parentheses): CVLS (H-ras), CVIM (K4B-Ras) and CVVM (N-Ras).

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof. Purification by HPLC was utilized for Example 1 as set forth below.

Example 1

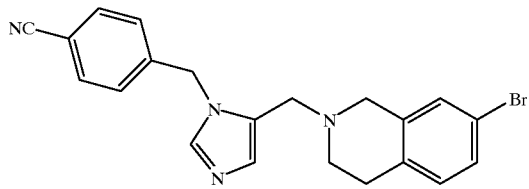

7-Bromo-2-(1-(4-cyanobenzyl)-5-imidazolylmethyl)-1,2,3,4-tetrahydroisoquinoline

Step 1: Preparation of 1-triphenylmethyl-4-(hydroxymethyl)-imidazole

To a solution of 4-(hydroxymethyl)imidazole hydrochloride (35 g) in 250 mL of dry DMF at room temperature was added triethylamine (90.6 mL). A white solid precipitated from the solution. Chlorotriphenylmethane (76.1 g) in 500 mL of DMF was added dropwise. The reaction mixture was stirred for 20 hours, poured over ice, filtered, and washed with ice water. The resulting product was slurried with cold dioxane, filtered, and dried in vacuo to provide the title compound as a white solid which was sufficiently pure for use in the next step.

Step 2: Preparation of 1-triphenylmethyl-4-(acetoxymethyl)-imidazole

The alcohol prepared above was suspended in 500 mL of pyridine. Acetic anhydride (74 mL) was added dropwise, and the reaction was stirred for 48 hours during which it became homogeneous. The solution was poured into 2 L of EtOAc, washed with water (3×1 L), 5% aq. HCl soln. (2×1 L), sat. aq. NaHCO$_3$, and brine, then dried (Na$_2$SO$_4$), filtered, and concentrated in vacuo to provide the crude product. The title compound was isolated as a white powder which was sufficiently pure for use in the next step.

Step 3: Preparation of 1-(4-cyanobenzyl)-5-(acetoxymethyl)-imidazole hydrobromide A solution of the acetate from Step 2 (85.8 g) and α-bromo-p-tolunitrile (50.1 g) in 500 mL of EtOAc was stirred at 60° C. for 20 hours, during which a pale yellow precipitate formed. The reaction was cooled to room temperature and filtered to provide the solid imidazolium bromide salt. The filtrate was concentrated in vacuo to a volume 200 mL, reheated at 60° C. for two hours, cooled to room temperature, and filtered again. The filtrate was concentrated in vacuo to a volume 100 mL, reheated at 60° C. for another two hours, cooled to room temperature, and concentrated in vacuo to provide a pale yellow solid. All of the solid material was combined, dissolved in 500 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid which was used in the next step without further purification.

Step 4: Preparation of 1-(4-cyanobenzyl)-5-(hydroxymethyl)-imidazole

To a solution of the product from Step 3 (50.4 g) in 1.5 L of 3:1 THF/water at 0° C. was added lithium hydroxide monohydrate (18.9 g). After one hour, the reaction was concentrated in vacuo, diluted with EtOAc (3 L), and washed with water, sat. aq. NaHCO$_3$ and brine. The solution was then dried (Na$_2$SO$_4$), filtered, and concentrated in vacuo to provide the crude product as a pale yellow fluffy solid which was sufficiently pure for use in the next step without further purification.

Step 5: Preparation of 1-(4-cyanobenzyl)-5-imidazolecarboxaldehyde

To a solution of the alcohol from Step 4 (21.5 g) in 500 mL of DMSO at room temperature was added triethylamine (56 mL), then SO$_3$-pyridine complex (40.5 g). After 45 minutes, the reaction was poured into 2.5 L of EtOAc, washed with water (4×1 L) and brine, dried (Na$_2$SO$_4$), filtered, and concentrated in vacuo to provide the title aldehyde as a white powder which was sufficiently pure for use in the next step without further purification.

Step 6: Preparation of 7-bromo-2-(1-(4-cyanobenzyl)-5-imidazolylmethyl)-1,2,3,4-tetrahydroisoquinoline To a solution of 7-bromo-1,2,3,4-tetrahydroisoquinoline (0.742 g, 3.5 mmol) in CHCl$_2$CHCl$_2$ (15 mL) was added 1-(4-cyanobenzyl)-5-imidazole carboxaldehyde (0.812 g, 3.85 mmol), 4 Å sieves and NaBH(OAc)$_3$ (1.11 g, 5.25 mmol). The mixture was stirred at room temperature for 16 h. and a further portion of NaBH(OAc)$_3$ (0.55 g, 2.6 mmol) was added. After an additional 24 h the mixture was diluted with EtOAc, filtered through celite, washed with brine, dried (Na$_2$SO$_4$) and concentrated. The residue was stirred in 2N Hcl (50 mL) for 2 h. then extracted with ether. The aqueous layer was basified with 6N KOH and extracted 3× CH$_2$Cl$_2$ which was then washed with brine, dried (Na$_2$SO$_4$) and the solvent evaporated in vacuo. Crystallization from ether afforded the title compound as a white solid.

Analysis for C$_{21}$H$_{19}$N$_4$Br Calcd. C, 61.92; H, 4.70; N,13.76 found C, 61.87; H, 4.71; N,13.58

Example 2

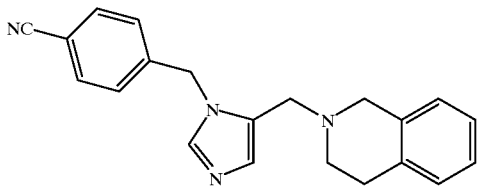

2-(1-(4-Cyanobenzyl)-5-imidazolylmethyl)-1,2,3,4-tetrahydroisoquinoline

Following the procedure described for Example 1, Step 6 but using 1,2,3,4-tetrahydroisoquinoline, the title compound was obtained as a white solid.

Analysis for $C_{21}H_{20}N_4$ Calcd. C, 76.80; H, 6.14; N,17.06 found C, 76.50; H, 5.93; N,16.94

Example 3

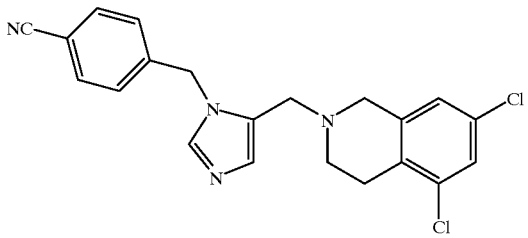

5,7-Dichloro-2-(1-(4-cyanobenzyl)-5-imidazolylmethyl)-1,2,3,4-tetrahydroisoquinoline Following the procedure described for Example 1, Step 6 but using 5,7-dichloro-1,2,3,4-tetrahydroisoquinoline, the title compound was obtained as a white solid.

Analysis for $C_{21}H_{18}N_4Cl_2$ Calcd. C, 63.48; H, 4.57; N,14.10 found C, 63.53; H, 4.67; N,14.30

Example 4

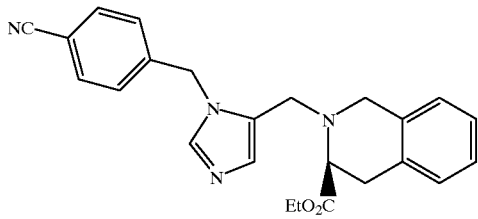

3(S)-Carboethoxy-2-(1-(4-cyanobenzyl)-5-imidazolylmethyl)-1,2,3,4-tetrahydroisoquinoline dihydrochloride salt Step 1: 3(S)-Carboethoxy-1,2,3,4-tetrahydroisoguinoline The title compound was obtained from N-Boc-L-1,2,3,4-tetrahydroisoquinoline-3-carboxylic acid (Bachem) using standard amino acid chemical procedures.

Step 2: 3(S)-Carboethoxy-2-(1-(4-cyanobenzyl)imidazol-5-ylmethyl)-1,2,3,4-tetrahydroisoquinoline dihydrochloride salt Following the procedure described for Example 1, Step 6 but using 3(S)-carboethoxy-1,2,3,4-tetrahydroisoquinoline, the title compound was obtained (after treatment with HCl in ether ) as a white solid.

Analysis for $C_{24}H_{24}N_4O_2$.2HCl Calcd. C, 58.98; H, 5.71; N,11.46 found C, 58.99; H, 5.63; N,11.39

Example 5

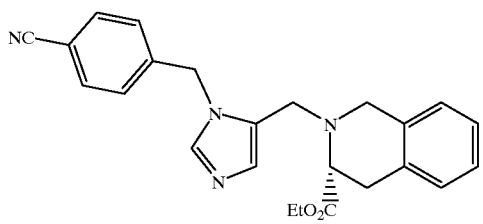

3(R)-Carboethoxy-2-(1-(4-cyanobenzyl)-5-imidazolylmethyl)-1,2,3,4-tetrahydroisoquinoline Dihydrochloride salt Step 1: 3(R)-Carboethoxy-1,2,3,4-tetrahydroisoquinoline The title compound was obtained from N-Boc-D-1,2,3,4-tetrahydroisoquinoline-3-carboxylic acid (Bachem) using standard amino acid chemical procedures.

Step 2: 3(R)-Carboethoxy-2-(1-(4-cyanobenzyl)imidazol-5-ylmethyl)-1,2,3,4-tetrahydroisoquinoline dihydrochloride salt Following the procedure described for Example 1, Step 6 but using 3(R)-carboethoxy-1,2,3,4-tetrahydroisoquinoline, the title compound was obtained (after treatment with HCl in ether) as a white solid.

Analysis for $C_{24}H_{24}N_4O_2$.2HCl Calcd. C, 55.77; H, 5.77; N,10.84 found C, 55.69; H, 5.77; N,10.92

Example 6

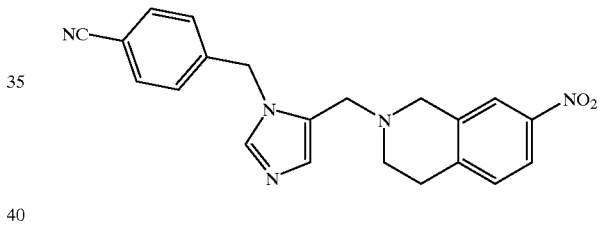

7-Nitro-2-(1-(4-cyanobenzyl)-5-imidazolylmethyl)-1,2,3,4-tetrahydroisoquinoline

Following the procedure described for Example 1, Step 6 but using 7-nitro-1,2,3,4-tetrahydroisoquinoline, the title compound was obtained (after treatment with HCl in ether) as a white solid.

Analysis for $C_{21}H_{19}N_5O_2$.1HCl.2H$_2$O.0.1EtOAc Calcd. C, 56.52; H, 5.50; N,15.40 found C, 56.57; H, 5.05; N,15.15

Example 7

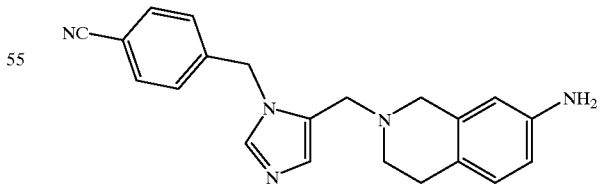

7-Amino-2-(1-(4-cyanobenzyl)-5-imidazolylmethyl)-1,2,3,4-tetrahydroisoquinoline tris Trifluoroacetate A solution of 7-nitro-1,2,3,4-tetrahydroisoquinoline (Example 6, 252 mg) in EtOAc (20 mL) was purged with argon and 10% palladium on carbon (100 mg) added. The mixture was then stirred under an atmosphere of hydrogen gas for 16 h. After filtration and removal of the solvent, the title compound was obtained as a white solid following purification by reverse phase HPLC.

Analysis for $C_{21}H_{21}N_5.3.2TFA.1H_2O$ Calcd. C, 45.31; H, 3.64; N,9.64 found C, 45.35; H, 3.52; N,9.84

Example 8

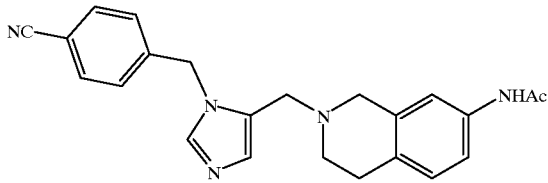

7-Acetamido-2-(1-(4-cyanobenzyl)-5-imidazolylmethyl)-1,2,3,4-tetrahydroisoquinoline bis hydrochloride salt A solution of 7-amino-1,2,3,4-tetrahydroisoquinoline tris trifluoroacetate (Example 7, 119 mg, 0.16 mmol) and triethylamine (80 μL, 0.57 mmol) in THF (2 mL) was treated with acetylchloride (12 μL, 0.16 mmol) and stirred for 16 h. The mixture was poured into saturated aqueous $NaHCO_3$, extracted with EtOAc, washed with water then brine, dried ($MgSO_4$) and concentrated. The residue was purified by reverse phase HPLC (gradient elution with water/acetonitrile containing 0.1% TFA) and the product converted to the HCl salt.

Analysis for $C_{23}H_{23}N_5O.2HCl.2H_2O.0.3EtOAc$ Calcd. C, 55.80; H, 6.08; N,13.45 found C, 55.99; H, 6.11; N,13.44

Example 9

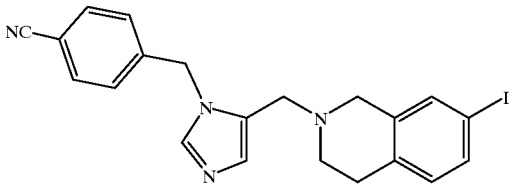

7-Iodo-2-(1-(4-cyanobenzyl)-5-imidazolylmethyl)-1, 2,3,4-tetrahydroisoquinoline bis hydrochloride salt Step 1: Preparation of 7-amino-2-trifluoroacetoxy-1,2,3,4-tetrahydroisoquinoline A solution of 7-nitro-2-trifluoroacetoxy-1,2,3,4-tetrahydroisoquinoline (Stokker, *Tetrahedron Letts.*, 1996, 37, 5453; 3.64 g, 13.3 mmol) in 100 mL EtOH at room temperature was was purged with argon and 10% palladium on carbon (300 mg) added. The mixture was then stirred under an atmosphere of hydrogen gas for 2 h. then filtered and the solvent removed in vacuo to yield a white solid which was sufficiently pure for use in the next step.

Step 2: Preparation of 7-iodo-2-trifluoroacetoxy-1,2,3,4-tetrahydroisoquinoline

The aniline prepared above (3.34 g, 13.7 mmol) was suspended in 30 mL 3N HCl, cooled to 0° C. and treated with a solution of $NaNO_2$ (1.04 g, 15.1 mmol) in 7 mL $H_2O$. After 30 minutes, a solution of KI (6.8 g, 41.1 mmol) in 10 mL $H_2O$ was added to the reaction mixture and stirring was continued for 45 minutes. The mixture was partitioned between $CHCl_3$ and water, the organic layer was washed with aqueous $NaHSO_3$ then brine, dried and evaporated. Chromatography of the residue (hexane/EtOAc 5:1) afforded the title compound as a colorless oil.

Step 3: Preparation of 7-iodo-1,2,34-tetrahydroisoquinoline

The iodide from Step 2 (2.8 g, 7.9 mmol) in THF (15 mL) and MeOH (30 mL) was treated with 1N LiOH (24 mL, 24 mmol) for 1 h at room temperature. After pouring into brine, the solution was extracted 2× EtOAc, washed with water then brine, dried and evaporated to give the title compound as a solid.

Step 4: 7-iodo-2-(1-(4-cyanobenzyl)-5-imidazolylmethyl)-1,2,3,4-tetrahydroisoquinoline bis hydrochloride salt Following the procedure described for Example 1, Step 6 but using 7-iodo-1,2,3,4-tetrahydroisoquinoline the title compound was obtained as the HCl salt as a white solid.

Analysis for $C_{21}H_{19}N_4I.2HCl.0.1EtOAc$ Calcd. C, 45.43; H, 4.47; N,9.90 found C, 45.40; H, 4.33; N,9.92

Example 10

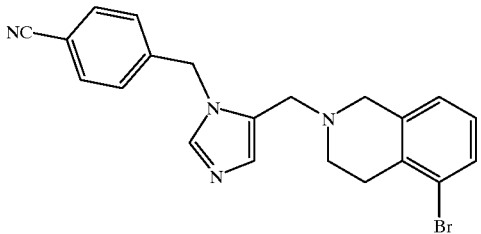

5-Bromo-2-(1-(4-cyanobenzyl)-5-imidazolylmethyl)-1,2,3,4-tetrahydroisoquinoline

Following the procedure described for Example 1, Step 6 but using 5-bromo-1,2,3,4-tetrahydroisoquinoline the title compound was obtained as a white solid.

Analysis for $C_{21}H_{19}N_4Br$ Calcd. C, 57.09; H, 4.34; N,12.48 found C, 57.32; H, 4.43; N,12.41

Example 11

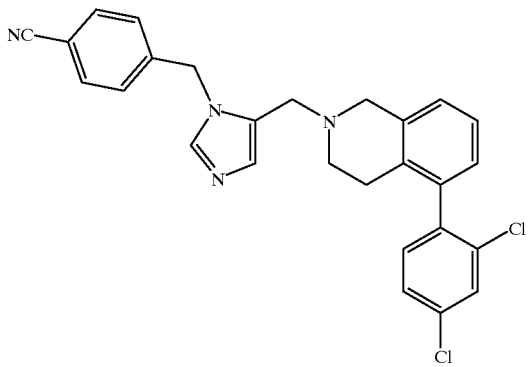

5-(2,4-Dichlorophenyl)-2-(1-(4-cyanobenzyl)-5-imidazolylmethyl)-1,2,3,4-tetrahydroisoquinoline A solution of 5-bromo-2-(1-(4-cyanobenzyl)-5-imidazolylmethyl)-1,2,3,4-tetrahydroisoquinoline (Example 10; 100 mg, 250 0.25 mmol), 2,4-dichlorophenyl boronic acid (53 mg, 0.275 mmol) and tetrakis(triphenylphosphine)

palladium(0) in DME (2 mL) and water (0.5 mL) was heated to 80° C. for 20 h. The mixture was partitioned between water and EtOAc, washed with aqueous NaHCO$_3$, water (2×), dried and evaporated. Column chromatography of the residue (silica gel; CHCl$_3$/MeOH 80:1) afforded the title compound as a white solid. FAB ms (m+1) 473.2

Example 12

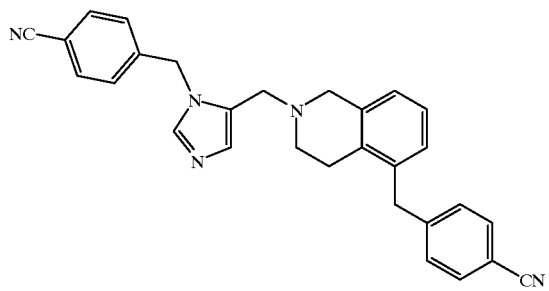

5-(4-Cyanobenzyl)-2-(1-(4-cyanobenzyl)-5-imidazolylmethyl)-1,2,3,4-tetrahydroisoquinoline Step 1: Preparation of 5-(4-cyanobenzyl)-2-trifluoroacetoxy-1,2,3 4-tetrahydroisoquinoline Dibromoethane (1 drop) was added to zinc dust (195 mg, 3.0 mmol) followed by THF (5 mL) and the slurry was stirred under argon for 15 minutes. 4-Cyanobenzylbromide (510 mg, 2.6 mmol) was added dropwise over 15 minutes and the mixture then stirred for 2 h. Bis(triphenylphosphine) nickel chloride (130 mg, 0.2 mmol) and 5-bromo-2-trifluoroacetoxy-1,2,3,4-tetrahydroisoquinoline (616 mg, 2 mmol) were added in one portion at room temperature. After 30 minutes, the reaction was heated to 40° C. for 3 h.then cooled and quenched with saturated NH$_4$Cl solution. The mixture was poured into water, extracted with EtOAc, washed with water, dried and the solvent removed in vacuo. Column chromatography of the dark mixture (silica gel; hexane/EtOAc 20:1 then 10:1 then 4:1) afforded the title compound. FAB ms (m+1) 345.15

Step 2: Preparation of 5-(4-cyanobenzyl)-1,2,3,4-tetrahydroisoquinoline

The trifluoroacetate from Step 1 was hydrolysed following the procedure described for Example 9, Step 3 to give the title compound.

Step 3 5-(4-cyanobenzyl)-2-(1-(4-cyanobenzyl)-5-imidazolylmethyl)-1,2,3,4-tetrahydroisoquinoline Following the procedure described for Example 1, Step 6 but using 5-(4-cyanobenzyl)-1,2,3,4-tetrahydroisoquinoline the title compound was obtained as a white solid. FAB ms (m+1) 444.25; m.p. 195–196° C.

Example 13

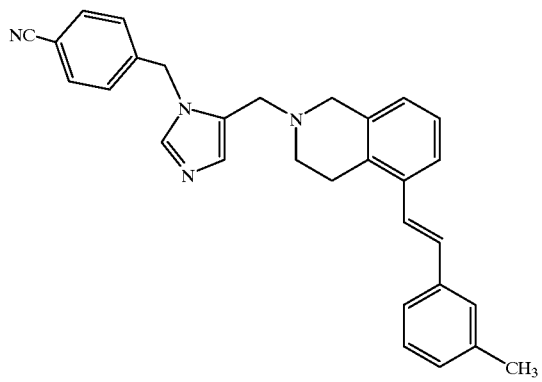

5-(2-(3-Tolyl)vinyl)-2-(1-(4-cyanobenzyl)-5-imidazolylmethyl)-1,2,3,4-tetrahydroisoquinoline
Bis trifluoroacetate salt Step 1: Preparation of 5-(2-(3-tolyl)vinyl)-2-trifluoroacetoxy-1,2,3,4-tetrahydroisoquinoline A solution of 5-bromo-2-trifluoroacetoxy-1,2,3,4-tetrahydroisoquinoline (616 mg, 2 mmol), 3-vinyltoluene (330 mg, 2.5 mmol), tri-o-tolylphosphine (50 mg) and palladium acetate (20 mg) in triethylamine (1 mL) were heated in a pressure bomb at 100° C. for 8 h. Column chromatography of the dark mixture (silica gel; hexane/EtOAc 40:1 then 20:1) afforded the title compound. FAB ms (m+1) 346.18

Step 2: Preparation of 5-(3-tolyl)vinyl)-1,2,3,4-tetrahydroisoquinoline

The trifluoroacetate from Step 1 was hydrolysed following the procedure described for Example 9, Step 3 to give the title compound.

Step 3 5-(3-tolyl)vinyl)-2-(1-(4-cyanobenzyl)-5-imidazolylmethyl)-1,2,3,4-tetrahydroisoquinoline Following the procedure described for Example 1, Step 6 but using 5-(3-tolyl)vinyl)-1,2,3,4-tetrahydroisoquinoline the title compound was obtained as a TFA salt following HPLC purification.

FAB ms (m+1) 445.04. Analysis for C$_{30}$H$_{28}$N$_4$.2TFA Calcd. C, 56.49; H, 4.41; N,7.55 found C, 56.45; H, 4.39; N,7.16

Example 14

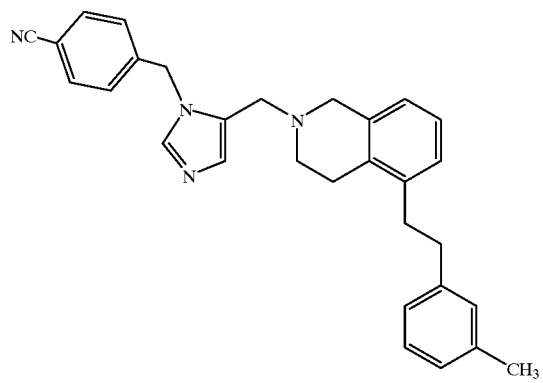

5-(2-(3-Tolyl)ethyl)-2-(1-(4-cyanobenzyl)-5-imidazolylmethyl)-1,2,3,4-tetrahydroisoquinoline
bis trifluoroacetate salt Step 1: Preparation of 5-(3-tolyl)ethyl)-1,2,3,4-tetrahydroisoquinoline The stilbene from Example 13, Step 2 (242 mg, 1 mmol) was hydrogenated in 10 mL EtOH with 50 mg 10% palladium on carbon and hydrogen gas (balloon). Filtration through celite and removal of the solvent gave the title compound.

Step 2 5-(3-Tolyl)ethyl)-2-(1-(4-cyanobenzyl)-5-imidazolylmethyl)-1,2,3,4-tetrahydroisoquinoline Following the procedure described for Example 1, Step 6 but using 5-(3-tolyl)ethyl)-1,2,3,4-tetrahydroisoquinoline the title compound was obtained as a TFA salt following HPLC purification. FAB ms (m+1) 447.21.

Example 15

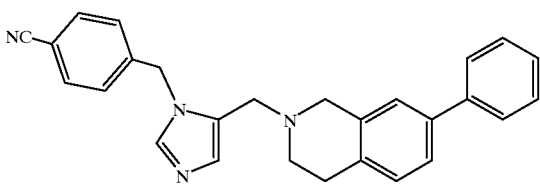

7-Phenyl-2-(1-(4-cyanobenzyl)-5-imidazolylmethyl)-1,2,3,4-tetrahydroisoquinoline Step 1: Preparation of 7-bromo-N-Boc-1,2,3,4-tetrahydroisoquinoline 7-Bromo-1,2,3,4-tetrahydroisoquinoline (1.58 g, 7.45 mmol) in DMF (30 mL) was treated with triethylamine (1.04 mL, 7.45 mmol) and $(Boc)_2O$ (1.75 g, 8 mmol) for 16 h. The DMF was removed in vacuo and the residue partitioned between water and EtOAc. Extracted with EtOAc (3×), washed with saturated $NaHCO_3$ then brine, dried and evaporated. Chromatography of the residue (silica gel; hexane/EtOAc 9:1) afforded the title compound as an oil.

Step 2: Preparation of 7-phenyl-N-Boc-1,2,3,4-tetrahydroisoquinoline

7-Bromo-2-(trifluoroacetoxy)-1,2,3,4-tetrahydroisoquinoline was coupled with phenyl boronic acid following the procedure of Example 11 to give the title compound as a viscous oil.

Step 3: Preparation of 7-phenyl-1,2,3,4-tetrahydroisoquinoline

HCl gas was bubbled through a solution of the Boc-amine from Step 2 (0.72 g) in EtOAc (25 mL) at −25° C. for 10 minutes. The solution was stoppered and stirred at 0° C. for 1.5 h. then the solvent was removed in vacuo. Trituration of the solid with EtOAc (25 mL) and filtration afforded the title compound as a solid Step 4: Preparation of 7-phenyl-2-(1-(4-cyanobenzyl)-5-imidazolylmethyl)-1,2,3,4-tetrahydroisoquinoline Following the procedure described for Example 1, Step 6 but using 7-phenyl-1,2,3,4-tetrahydroisoquinoline the title compound was obtained as a white solid.

Analysis for $C_{27}H_{24}N_4$ Calcd. C, 80.17; H, 5.98; N,13.85 found C, 80.36; H, 5.98; N,14.12

Example 16

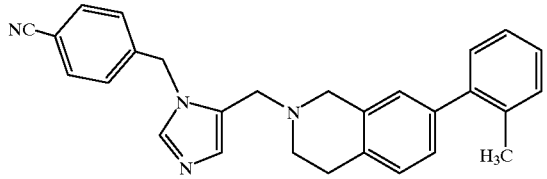

7-(2-Tolyl)-2-(1-(4-cyanobenzyl)-5-imidazolylmethyl)-1,2,3,4-tetrahydroisoquinoline Step 1: Preparation of 7-bromo-N-Boc-1,2,3,4-tetrahydroisoquinoline 7-Bromo-1,2,3,4-tetrahydroisoquinoline (1.58 g, 7.45 mmol) in DMF (30 mL) was treated with triethylamine (1.04 mL, 7.45 mmol) and (Boc)2O (1.75 g, 8 mmol) for 16 h. The DMF was removed in vacuo and the residue partitioned between water and EtOAc. Extracted with EtOAc (3×), washed with saturated NaHCO3 then brine, dried and evaporated. Chromatography of the residue (silica gel; hexane/EtOAc 9:1) afforded the title compound as an oil Step 2: Preparation of 7-(2-tolyl)-N-Boc-1,2,3,4-tetrahydroisoquinoline 7-Bromo-2-(trifluoroacetoxy)-1,2,3,4-tetrahydroisoquinoline was coupled with 2-methylphenyl boronic acid following the procedure of Example 11 to give the title compound as a viscous oil.

Step 3: Preparation of 7-(2-tolyl)-1,2,3,4-tetrahydroisoquinoline hydrochloride salt HCl gas was bubbled through a solution of the Boc-amine from Step 2 (0.72 g) in EtOAc (25 mL) at −25° C. for 10 minutes. The solution was stoppered and stirred at 0° C. for 1.5 h. then the solvent was removed in vacuo. Trituration of the solid with EtOAc (25 mL) and filtration afforded the title compound as a solid Step 4: Preparation of 7-(2-tolyl)-2-(1-(4-cyanobenzyl)-5-imidazolylmethyl)-1,2,3,4-tetrahydroisoquinoline Following the procedure described for Example 1, Step 6 but using 7-(2-tolyl)-1,2,3,4-tetrahydroisoquinoline the title compound was obtained as a white solid.

Analysis for $C_{28}H_{26}N_4 \cdot 2HCl \cdot 1.5H_2O$ Calcd. C, 64.86; H, 6.03; N,10.81 found C, 65.04; H, 6.17; N,10.67

Example 17

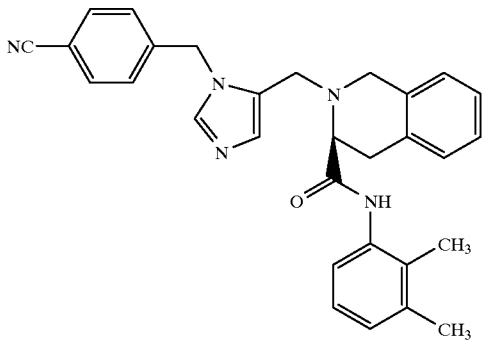

N-(2,3-Dimethylphenyl)-2-(1-(4-cyanobenzyl)-5-imidazolylmethyl)-1,2,3,4-tetrahydroisoquinoline-3 (S)-carboxamide bis trifluoroacetate salt Step 1: N-(2,3-dimethylphenyl) 1,2,3,4-tetrahydroisoquinoline-3(S)-carboxamide N-Boc-L-1,2,3,4-tetrahydroisoquinoline-3-carboxylic acid (Bachem) was coupled with 2,3-dimethyl aniline using standard peptide coupling procedures. The product was deprotected using TFA in $CH_2Cl_2$ to give the title compound.

Step 2: Preparation of N-(2,3-dimethylphenyl)-2-(1-(4-cyanobenzyl)-5-imidazolylmethyl)-1,2,3,4-tetrahydroisoquinoline-3(S)-carboxamide bis trifluoroacetate salt Following the procedure described for Example 1, Step 6 but using N-(2,3-dimethylphenyl)-1,2,3,4-tetrahydroisoquinoline-3(S)-carboxamide the title compound was obtained as a white solid.

Analysis for $C_{30}H_{29}N_5O.2.6TFA.0.2H_2O$ Calcd. C, 54.51; H, 4.16; N, 9.03 found C, 54.58; H, 4.22; N, 8.82

Example 18

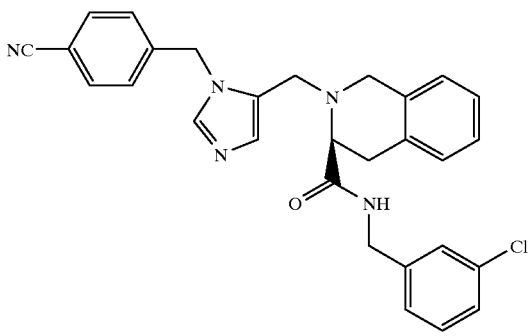

N-(3-Chlorobenzyl) 2-(1-(4-cyanobenzyl)-5-imidazolylmethyl)-1,2,3,4-tetrahydroisoquinoline-3 (S)-carboxamide bis trifluoroacetate salt Following the procedure described for Example 17 but using 3-chlorobenzylamine, the title compound was obtained as a white solid.

Analysis for $C_{29}H_{26}N_5OCl.2.2TFA$ Calcd. C, 53.71; H, 3.81; N, 9.38 found C, 53.67; H, 3.76; N, 9.25

Example 19

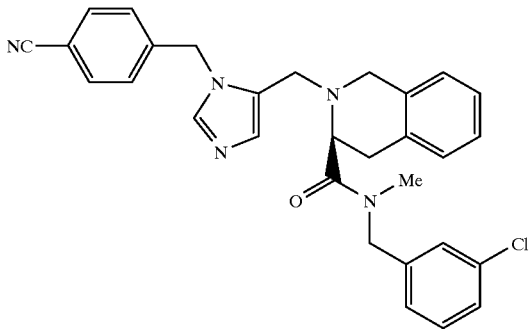

N-(3-Chlorobenzyl),N-methyl 2-(1-(4-cyanobenzyl)-5-imidazolylmethyl)-1,2,3,4-tetrahydroisoquinoline-3(s)-carboxamide bis trifluoroacetate salt Step 1: Preparation of N-(3-chlorobenzyl) 2-Boc-1,2,3,4-tetrahydroisoquinoline-3(S)-carboxamide N-Boc-L-1,2,3,4-tetrahydroisoquinoline-3-carboxylic acid (Bachem) was coupled with 3-chlorobenzylamine using standard peptide coupling procedures to give the title compound.

Step 2: Preparation of N-(3-chlorobenzyl), N-methyl 2-Boc-1,2,3,4-tetrahydroisoquinoline-3(S)-carboxamide The product from Step 1 (390 mg, 0.945 mmol) was dissolved in dry DMF (5 mL) at 0° C. and then treated with NaH (49 mg, 1.23 mmol). After 5 minutes, methyl iodide (76 μL, 1.23 mmol) was added and the reaction was stirred for 16 h. The mixture was poured into water and extracted with EtOAc, washed aqueous $NaHCO_3$ then brine, dried and evaporated to give the title product which was used as such.

Step 3: Preparation of N-(3-chlorobenzyl),N-Methyl 2-(1-(4-cyanobenzyl)-5-imidazolylmethyl)-1,2,3,4-tetrahydroisoquinoline-3(S)-carboxamide bis trifluoroacetate salt Following the procedure described for Example 17 but using N-methyl 2-Boc-1,2,3,4-tetrahydroisoquinoline-3(S)-carboxamide, the title compound was obtained as a white solid.

Analysis for $C_{30}H_{28}N_5OCl.2.3TFA$ Calcd. C, 53.81; H, 3.95; N, 9.07 found C, 53.91; H, 3.87; N, 9.04

Example 20

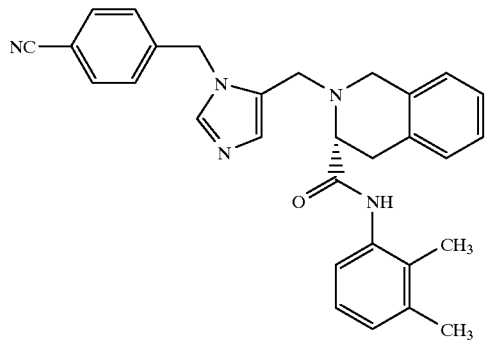

N-(2,3-Dimethylphenyl)-2-(1-(4-cyanobenzyl)-5-imidazolylmethyl)-1,2,3,4-tetrahydroisoquinoline-3 (R)-carboxamide bis hydrochloride salt Following the procedure described for Example 17 but using N-Boc-D-1,2,3,4-tetrahydroisoquinoline-3-carboxylic acid (Bachem) the title compound was obtained as a white solid.

Analysis for $C_{30}H_{29}N_5O.2HCl.H_2O$ Calcd. C, 63.60; H, 5.87; N, 12.36 found C, 63.50; H, 5.99; N, 12.36

Example 21

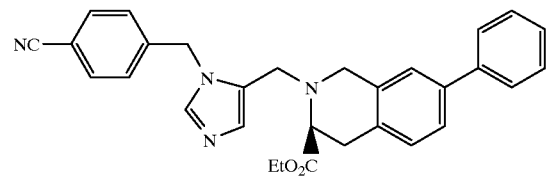

3(S)-Carboethoxy-7-phenyl-2-(1-(4-cyanobenzyl)-5-imidazolylmethyl)-1,2,3,4-tetrahydroisoquinoline dihydrochloride salt Step 1: Preparation of 2-Boc-3(S)-carboethoxy-7-hydroxy-1,2,3,4-tetrahydroisoquinoline The title compound was obtained from L-2-hydroxy-1,2,3,4-tetrahydroisoquinoline-3-carboxylic acid (Bachem) using standard amino acid chemical procedures (EtOH/HCl followed by $(Boc)_2O$/triethylamine in $CH_2Cl_2$).

Step 2: Preparation of 2-Boc-3(S)-carboethoxy-7-trifluoromethylsulfonyloxy-1,2,3,4-tetrahydroisoquinoline The phenol from Step 1 (0.6 g, 1.87 mmol) was dissolved in CH$_2$Cl$_2$ (20 mL) and triethylamine (0.78 mL, 5.6 mmol) at room temperature. Trifluoromethanesulfonic anhydride (0.345 mL, 2.06 mmol) was added and the mixture stirred for 16 h. The solution was poured into aqueous NaHCO3 and extracted with CH$_2$Cl$_2$ (3×), washed with brine, dried and concentrated to give a brown oil. Column chromatography (silica gel; hexane/EtOAc 4:1) provided the title compound as an oil.

Step 3: Preparation of 2-Boc-3(S)-carboethoxy-7-phenyl-1,2,3,4-tetrahydroisoquinoline The triflate from Step 2 was coupled with phenyl boronic acid following the procedure of Example 11 to give the title compound as an oil.

Step 4: Preparation of 3(S)-carboethoxy-7-phenyl-1,2,3,4-tetrahydroisoquinoline hydrochloride The Boc-amine from Step 3 (48 mg) was deprotected using 75 mL EtOAc saturated with HCl. Removal of the solvent in vacuo gave the title compound as a white solid.

Step 5: Preparation of 3(S)-carboethoxy-7-phenyl-2-(1-(4-cyanobenzyl)-5-imidazolylmethyl)-1,2,3,4-tetrahydroisoquinoline dihydrochloride salt Following the procedure described for Example 1, Step 6 but using the product from Step 4 the title compound was obtained as a white solid.

Analysis for C$_{30}$H$_{28}$N$_4$O$_2$.2HCl.0.2H$_2$O Calcd. C, 65.14; H, 5.54; N,10.13 found C, 65.12; H, 5.58; N,9.77

Example 22

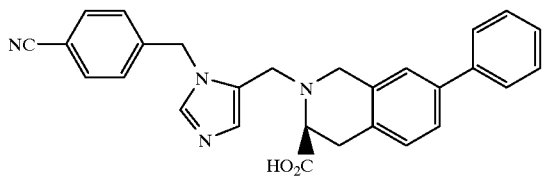

3(S)-Carboxylic acid-7-phenyl-2-(1-(4-cyanobenzyl)-5-imidazolylmethyl)-1,2,3,4-tetrahydroisoquinoline 3(S)-Carboethoxy-7-phenyl-2-(1-(4-cyanobenzyl)-5-imidazolylmethyl)-1,2,3,4-tetrahydroisoquinoline (100 mg, 0.21 mmol) from Example 21 was hydrolysed in THF (5 mL) and water (5 mL) using 1N LiOH (0.84 mL, 0.84 mmol). After 16 h, the mixture was neutralized with HCl (pH~7) and extracted with EtOAc (3×), washed with brine, dried and evaporated to give the title compound as a white solid.

Analysis for C$_{28}$H$_{24}$N$_4$O$_2$.1.1EtOAc Calcd. C, 71.34; H, 6.06; N,10.27 found C, 71.25; H, 5.77; N,10.55

Example 23

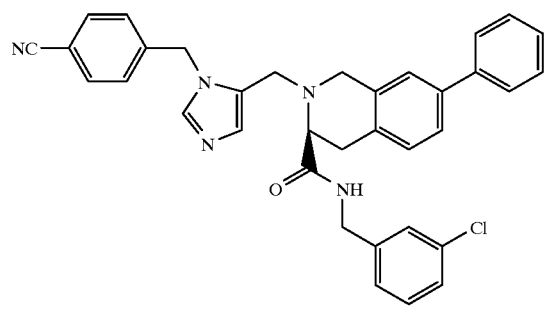

N-(3-Chlorobenzyl)-7-phenyl-2-(1-(4-cyanobenzyl)-5-imidazolylmethyl)-1,2,3,4-tetrahydroisoquinoline-3 (S)-carboxamide bis hydrochloride salt Following the procedure described for Example 18 but using 3(S)-carboxylic acid-7-phenyl-2-(1-(4-cyanobenzyl)-5-imidazolylmethyl)-1,2,3,4-tetrahydroisoquinoline from Example 22, the title compound was obtained as a white solid.

Analysis for C$_{35}$H$_{30}$N$_5$OCl1.2.35HCl0.15EtOAc Calcd. C, 63.72; H, 5.04; N,10.44 found C, 63.69; H, 5.43; N,10.54

Example 24

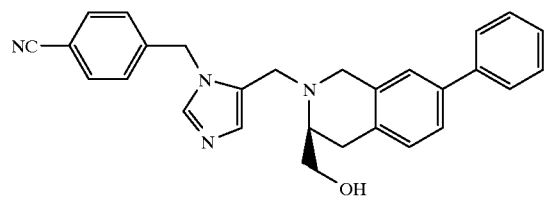

3(S)-Hydroxymethyl-7-phenyl-2-(1-(4-cyanobenzyl)-5-imidazolylmethyl)-1,2,3,4-tetrahydroisoquinoline bis hydrochloride salt 3(S)-Carboethoxy-7-phenyl-2-(1-(4-cyanobenzyl)-5-imidazolylmethyl)-1,2,3,4-tetrahydroisoquinoline (150 mg, 0.32 mmol) from Example 21 was dissolved in THF (3 mL) and treated with LiBH$_4$ (13.7 g, 0.64 mmol). The solution was heated at 50° C. for 3 h then quenched with 1N HCl and extracted with EtOAc (3×), washed with brine, dried and evaporated. The residue was purified by preparative HPLC (gradient elution with water/acetonitrile containing 0.1% TFA), the product neutralized and converted to the HCl salt using 1N HCl in ether to give the title compound as a white solid.

Analysis for C$_{28}$H$_{26}$N$_4$O$_2$.2.5HCl.0.5EtOAc Calcd. C, 63.24; H, 5.75; N,9.83 found C, 63.22; H, 5.88; N,10.00

Example 25

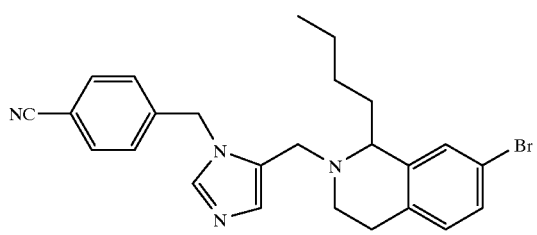

1(R,S)-n-Butyl-7-bromo-2-(1-(4-cyanobenzyl)-5-imidazolylmethyl)-1,2,3,4-tetrahydroisoquinoline Dihydrochloride salt Step 1: Preparation of N-pentanoyl 2-(4-bromophenethyl) amine A solution of 4-bromophenethylamine (3.2 g, 16 mmol) and triethylamine (2.34 mL, 16.8 mmol) in CH$_2$Cl$_2$ at 0° C. was treated with valeryl chloride (2.03 g, 16.8 mmol) and then stirred at room temperature for 16 h. The solvent was removed in vacuo, EtOAc then added and the solution washed with brine, 10% KHSO$_4$ solution, saturated NaHCO$_3$ and then brine. After drying, the solvent was removed to give the title compound as a solid.

Step 2: Preparation of 1-n-butyl-7-bromo-3,4-dihydroisoquinoline

Following the procedure described by Larsen et al (*J. Org. Chem.*, 1991, 56, 6034) the amide from Step 1 (0.853 g, 3 mmol) was dissolved in CH$_2$Cl$_2$ (25 mL) at 0° C. and was treated with oxalyl chloride (0.288 mL, 3.3 mmol). The mixture was stirred at room temperature for 18 h then FeCl$_3$ (anhydrous; 0.584 g, 3.6 mmol) was added at 0° C. and the mixture was then stirred for a further 18 h at room temperature. The reaction was quenched with 2N HCl, stirred for 1 h then extracted with CH$_2$Cl$_2$, washed with brine, dried and the solvent removed to give a solid. This solid was stirred in MeOH (19 mL) and conc. H$_2$SO$_4$ (1 mL) at reflux for 18 h, the mixture was cooled and the methanol removed in vacuo. Water and EtOAc was added to the residue, and the organic layer was washed twice with 1N HCl. The combined aqueous extracts were basified with conc. NH$_4$OH, extracted with CH$_2$Cl$_2$, washed with brine, dried and the solvent removed to give the title compound as a viscous oil.

Step 3: Preparation of 1(R,S)-n-butyl-7-bromo-1,2,3,4-tetrahydroisoquinoline

The imine from Step 2 was dissolved in absolute EtOH (25 mL) and NaBH4 (0.303 g, 8.0 mmol) was added. After 2 h, the solvent was removed and the residue treated with 1N HCL. Conc. NH$_{40}$H was added to the solution which was then extracted with CH$_2$Cl$_2$ (3×), washed with brine, dried and concentrated to give the title compound as a viscous oil which was used as such.

Step 4: Preparation of 1(R,S)-n-butyl-7-bromo-2-(1-(4-cyanobenzyl)-5-imidazolylmethyl)-1,2,3,4-tetrahydroisoquinoline dihydrochloride salt Following the procedure described for Example 1, Step 6 but using the product from Step 3 the title compound was obtained as a white solid.

Analysis for C$_{25}$H$_{27}$N$_4$Br.2.5HCl.1.5H$_2$O Calcd. C, 51.62; H, 5.63; N,9.63 found C, 51.66; H, 5.48; N,9.61

Example 26

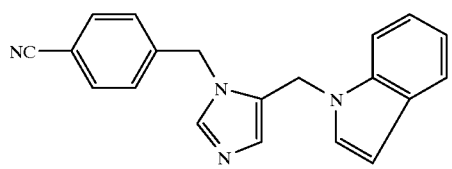

1-(1-(4-Cyanobenzyl)-5-imidazolylmethyl)indole

Step 1: Preparation of 1-(4-cyanobenzyl)-5-(chloromethyl) imidazole hydrochloride A suspension of 1-(4-cyanobenzyl)-5-(hydroxymethyl)-imidazole from Example 1, Step 4 (3.1 g) in thionyl chloride (20 mL) was heated at 60° C. for 16 h. The reaction was concentrated in vacuo, azeotroped with CHCl$_3$ and filtered to give the title compound as a pale yellow solid which was sufficiently pure for use in the next step without further purification.

Step 2: Preparation of 1-(1-(4-cyanobenzyl)-5-imidazolylmethyl) indole

Indole (117 mg, 1.0 mmol) dissolved in DMF (15 mL) was treated with NaH (48 mg, 2 mmol) and stirred for 30 minutes before the addition of the chloride from Step 1 (268 mg, 1 mmol). The mixture was stirred for 16 h, poured into water, extracted with EtOAc (3×), washed with aqueous NaHCO$_3$ then brine, dried and evaporated to give an oil. Chromatography of this oil (silica gel; 2.5% MeOH in CHCl$_3$) gave an oil which solidified when stirred in ether. Filtration afforded the title product as an off-white solid.

Analysis for C$_{20}$H$_{16}$N$_4$ Calcd. C, 76.90; H, 5.16; N,17.94 found C, 76.66; H, 5.20; N,17.72

Example 27

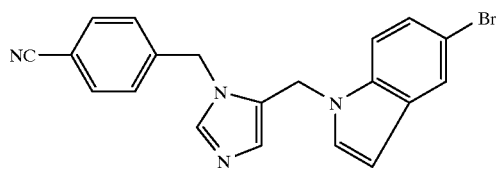

5-Bromo-1-(1-(4-cyanobenzyl)-5-imidazolylmethyl) indole

Following the procedure described for Example 26, Step 2 but using 5-bromoindole (Aldrich) the title compound was obtained as a solid.

Analysis for C$_{20}$H$_{15}$N$_4$Br Calcd. C, 61.39; H, 3.86; N,14.32 found C, 61.38; H, 3.98; N,14.35

Example 28

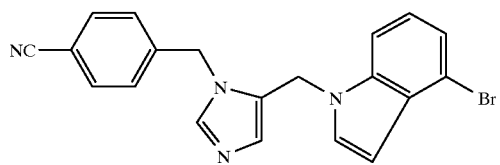

4-Bromo-1-(1-(4-cyanobenzyl)-5-imidazolylmethyl)indole

Following the procedure described for Example 26, Step 2 but using 4-bromoindole (TCI) the title compound was obtained as a solid.

Analysis for $C_{20}H_{15}N_4Br$ Calcd. C, 61.39; H, 3.86; N,14.32 found C, 61.40; H, 3.89; N,14.34

Example 29

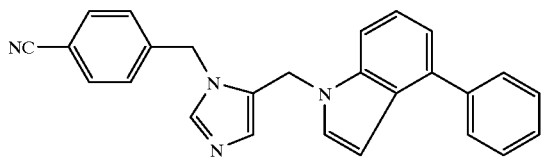

4-Phenyl-1-(1-(4-cyanobenzyl)-5-imidazolylmethyl)indole

Step 1: Preparation of 4-phenylindole

Following the procedure described for Example 21, Steps 2 and 3, 5-hydroxyindole (Aldrich) was converted into the title compound.

Step 2: Preparation of 4-phenyl-1-(1-(4-cyanobenzyl)-5-imidazolylmethyl)indole

Following the procedure described for Example 26, Step 2 but using 4-phenylindole from Step 1, the title compound was obtained (after HPLC purification) as a TFA salt.

Analysis for $C_{26}H_{20}N_4 \cdot 1.2TFA \cdot 0.75H_2O$ Calcd. C, 63.30; H, 4.25; N,10.40 found C, 63.29; H, 4.14; N,10.70

Example 30

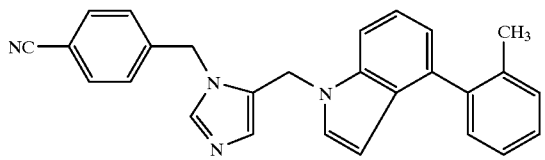

4-(2-Methylphenyl)-1-(1-(4-cyanobenzyl)-5-imidazolylmethyl)indole

Following the procedure described for Example 21, Step 3, 4-bromo-1-(1-(4-cyanobenzyl)-5-imidazolylmethyl)indole (Example 28) was coupled with 2-methylphenyl boronic acid to give the title compound.

Analysis for $C_{27}H_{22}N_4 \cdot 0.25CHCl_3$ Calcd. C, 75.70; H, 5.19; N,12.96 found C, 76.06; H, 5.35; N,13.07

Example 31

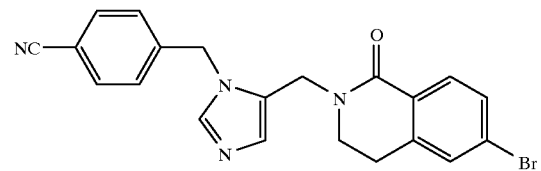

6-Bromo-2-(1-(4-cyanobenzyl)-5-imidazolylmethyl)-3,4-dihydro-1(1 H)-isoquinolinone hydrochloride salt Step 1: Preparation of 6-Bromo-3,4-dihydro-1(1H)-isoquinolinone To a rapidly stirred solution of 5-bromo-1-indanone (Aldrich) (15.0 g, 71.1 mmol) in benzene (200 mL) and $H_2SO_4$ (38 mL) was added $NaN_3$ portionwise over 20 minutes. The mixture was diluted EtOAc, washed with water then brine, dried and evaporated. Chromatography of the residue (silica gel; hexane/EtOAc 1:1) afforded the title compound as a solid.

Step 2: Preparation of 6-bromo-2-(1-(4-cyanobenzyl)-5-imidazolylmethyl)-3,4-dihydro-1(1H)-isoquinolinone hydrochloride salt Following the procedure described for Example 26, Step 2, but using 6-bromo-3,4-dihydro-1(1H)-isoquinolinone from Step 1, the title compound was obtained.

Analysis for $C_{21}H_{17}N_4Br \cdot 1.5HCl \cdot 1.5H_2O$ Calcd. C, 50.14; H, 4.31; N,11.14 found C, 50.55; H, 4.03; N,10.74

Example 32

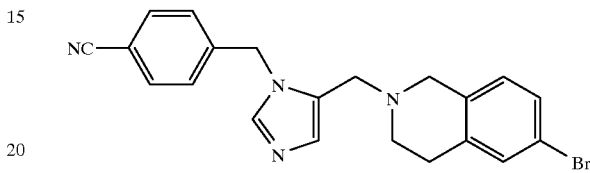

6-Bromo-2-(1-(4-cyanobenzyl)-5-imidazolylmethyl)-1,2,3,4-tetrahydroisoquinoline

Step 1: Preparation of 6-bromo-1,2,3,4-tetrahydroisoquinoline

A solution of 6-bromo-3,4-dihydro-1(1H)-isoquinolinone (Example 31, Step 1; 5.5 g, 1.0 mmol) in THF (25 mL) was treated with 1M $BH_3$ in THF (5 mL, 5 mmol) and heated at reflux for 20 h. To the mixture was added MeOH (5 mL), the solvent removed and the residue heated with 2N HCl for 3 h. The reaction was cooled, made basic with aqueous $NH_4OH$ and extracted with $CH_2Cl_2$, dried and evaporated to give the title compound as a gum which was used as such.

Step 2: Preparation of 6-Bromo-2-(1-(4-cyanobenzyl)-5-imidazolylmethyl)-1,2,3,4-tetrahydroisoquinoline Following the procedure described for Example 1, Step 6 but using 6-bromo-1,2,3,4-tetrahydroisoquinoline from Step 1 the title compound was obtained.

Analysis for $C_{21}H_{19}N_4Br$ Calcd. C, 61.92; H, 4.70; N,13.76 found C, 61.59; H, 4.65; N,13.49

Example 33

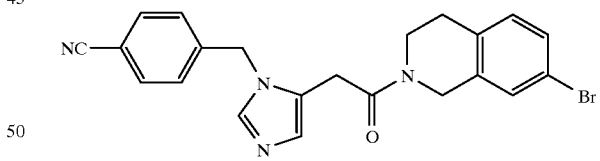

7-Bromo-2-(1-(4-cyanobenzyl)-5-imidazolylacetyl)-1,2,3,4-tetrahydroisoquinoline hydrochloride Step 1: Preparation of 1H-imidazole-4-acetic acid methyl ester hydrochloride A solution of 1H-imidazole-4-acetic acid hydrochloride (4.00 g, 24.6 mmol) in methanol (100 mL) was saturated with gaseous hydrogen chloride. The resulting solution was allowed to stand at room temperature for 18 h. The solvent was evaporated in vacuo to afford the title compound as a white solid.

$^1$H NMR(CDCl$_3$, 400 MHz) δ 8.85(1H, s),7.45(1H, s), 3.89(2H, s) and 3.75(3H, s) ppm.

Step 2: Preparation of 1-(triphenylmethyl)-1H-imidazol-4-ylacetic acid methyl ester To a solution of 1H-imidazole-4-acetic acid methyl ester hydrochloride (24.85 g, 0.141 mol) in DMF (115 mL) was added triethylamine (57.2 mL, 0.412 mol) and triphenylmethyl bromide (55.3 g, 0.171 mol) and the suspension was stirred for 24 h. After this time, the reaction mixture was diluted with EtOAc (1 L) and water (350 mL). The organic phase was washed with sat. aqueous NaHCO$_3$ (350 mL), dried (Na$_2$SO$_4$) and evaporated in vacuo. The residue was purified by flash chromatography (SiO$_2$, 0–100% ethyl acetate in hexanes; gradient elution) to provide the title compound as a white solid.

$^1$H NMR (CDCl$_3$, 400 MHz) δ 7.35(1H, s), 7.31(9H, m), 7.22(6H, m), 6.76(1H, s), 3.68(3H, s) and 3.60(2H, s) ppm.

Step 3: Preparation of [1-(4-cyanobenzyl)-1H-imidazol-5-yl]acetic acid methyl ester To a solution of 1-(triphenylmethyl)-1H-imidazol-4-ylacetic acid methyl ester (8.00 g, 20.9 mmol) in acetonitrile (70 mL) was added bromo-p-toluonitrile (4.10 g, 20.92 mmol) and heated at 55° C. for 3 hr. After this time, the reaction was cooled to room temperature and the resulting imidazolium salt (white precipitate) was collected by filtration. The filtrate was heated at 55° C. for 18 h. The reaction mixture was cooled to room temperature and evaporated in vacuo. To the residue was added EtOAc (70 mL) and the resulting white precipitate collected by filtration. The precipitated imidazolium salts were combined, suspended in methanol (100 mL) and heated to reflux for 30 minutes. After this time, the solvent was removed in vacuo, the resulting residue was suspended in EtOAc (75 mL) and the solid isolated by filtration and washed (EtOAc). The solid was treated with sat aq NaHCO$_3$ (300 mL) and CH$_2$Cl$_2$ (300 mL) and stirred at room temperature for 2 h. The organic layer was separated, dried (MgSO$_4$) and evaporated in vacuo to afford the title compound as a white solid:

$^1$HNMR(CDCl$_3$, 400 MHz) δ 7.65(1H, d, J=8 Hz), 7.53 (1H, s), 7.15(1H, d, J=8 Hz), 7.04(1H, s), 5.24(2H, s), 3.62(3H, s) and 3.45(2H, s) ppm.

Step 4: Preparation of [1-(4-cyanobenzyl)-1H-imidazol-5-yl]acetic acid

A solution of [1-(4-cyanobenzyl)-1H-imidazol-5-yl]acetic acid methyl ester (4.44 g, 17.4 mmol) in THF (100 mL) and 1 M lithium hydroxide (17.4 mL, 17.4 mmol) was stirred at room temperature for 18 h. 1 M HCl (17.4 mL) was added and the THF was removed by evaporation in vacuo. The aqueous solution was lyophilized to afford the title compound containing lithium chloride as a white solid.

$^1$H NMR(CD$_3$OD, 400 MHz) δ 8.22(1H, s), 7.74(1H, d, J=8.4 Hz), 7.36(1H, d, J=8.4 Hz), 7.15(1H, s), 5.43(2H, s) and 3.49(2H, s) ppm.

Step 5: Preparation 7-bromo-2-(1-(4-cyanobenzyl)-5-imidazolylacetyl)-1,2,3,4-tetrahydroisoquinoline hydrochloride The acid from Step 4 (0.575 g, 2 mmol), 7-bromo-1,2,3, 4-tetrahydroisoquinoline (0.424 g, 2 mmol) and HOBT (0.297 g, 2.2 mmol) were dissolved in DMF (15 mL) and NMM (0.44 mL, 4 mmol) and EDC (0.46 g, 2.4 mmol) were added. The resulting solution was stirred for 16 h then poured into water and extracted with EtOAc (3×). The EtOAc layers were washed with aqueous NaHCO3 then brine, dried and evaporated to give an oil which was triturated with ether to afford a solid. Purification by preparative HPLC (gradient elution; acetonitrile/water containing 0.1% HCl) afforded the title compound.

Analysis for C$_{22}$H$_{19}$N$_4$OBr.1HCl Calcd. C, 56.00; H, 4.27; N,11.88 found C, 55.76; H, 4.18; N,11.69

Example 34

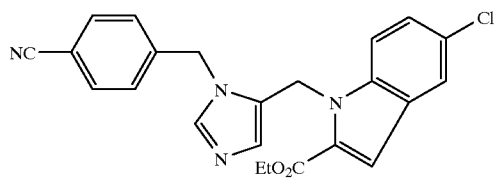

5-Chloro-2-carboethoxy-1-(1-(4-cyanobenzyl)-5-imidazolylmethyl)indole

Following the procedure described for Example 26, Step 2 but using 5-chloro-2-carboethoxyindole (Aldrich) the title compound was obtained as a solid.

Analysis for C$_{23}$H$_{19}$N$_4$ClO$_2$ Calcd. C, 65.95; H, 4.57; N,13.38 found C, 66.03; H, 4.62; N,12.92

Example 35

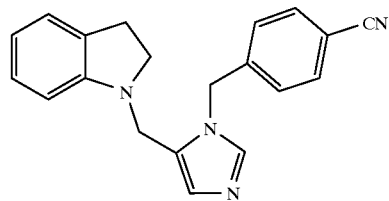

1-(4-Cyanobenzyl)-5-(1-indolinylmethyl)imidazole hydrochloride

To a solution of indoline (126 mg, 1.06 mmol) in 3 mL of dry DMF was added sodium hydride (93.0 mg, 2.33 mmol, 60% dispersion in mineral oil) at room temperature. After one hour, the solution was cooled to −50° C. and the chloride described in Example 26, Step 1 (284 mg, 1.06 mmol) was added as a solid. The reaction was slowly warmed to room temperature over 16 hours, poured onto water, and extracted with methylene chloride (3×10 mL). The combined organic layers were dried (Na$_2$SO$_4$), filtered, and concentrated in vacuo to provide a yellow oil. The crude product was purified by column chromatography (1–5% MeOH/CHCl$_3$) and then treated with HCl to provide the title compound as a white solid. MS (FAB) m+1=315. Elemental analysis for C$_{20}$H$_{18}$N$_4$.2.50HCl. 0.25 H$_2$O calc. C, 58.58; H, 5.16; N, 13.66; found C, 58.61; H, 4.82; N, 13.80.

Using the methods described above, the following compounds were prepared:

1-(4-cyanobenzyl)-5-(1-indazolylmethyl)imidazole hydrochloride

Analysis calculated for formula: C$_{19}$H$_{15}$N$_5$.1.70HCl.H$_2$O C, 51.18; H, 5.52; N, 12.24; Found C, 51.09; H, 5.25; N, 12.26.

1-(4-cyanobenzyl)-5-(1-tetrahydroquinolinylmethyl) imidazole hydrochloride

Analysis calculated for formula: C$_{21}$H$_{20}$N$_4$.2.25HCl C, 61.44; H, 5.46; N, 13.65; Found C, 61.45; H, 5.62; N, 13.54.

5-(1-benzotriazolylmethyl)-1-(4-cyanobenzyl)imidazole hydrochloride

Analysis calculated for formula: C$_{18}$H$_{14}$N$_6$.1.25HCl.0.15 Et$_2$O C, 60.20; H, 4.55; N, 22.65; Found C, 60.17; H, 4.31; N, 22.69.

5-(1-benzoimidazolylmethyl)-1-(4-cyanobenzyl)imidazole hydrochloride

Analysis calculated for formula: $C_{19}H_{15}N_5 \cdot 2.50HCl \cdot 1.35CH_2Cl_2$ C, 47.07; H, 3.92; N, 13.49; Found C, 47.13; H, 4.32; N, 13.47.

5-[1-(7-azaindolyl)methyl]-1-(4-cyanobenzyl)imidazole hydrochloride

Analysis calculated for formula: $C_{19}H_{15}N_5 \cdot 1.85HCl \cdot 1.05CH_2Cl_2$ C, 51.23; H, 4.06; N, 14.90; Found C, 51.23; H, 4.28; N, 14.90.

5-[1-(4-azabenzimidazolyl)methyl]-1-(4-cyanobenzyl) imidazole hydrochloride

Analysis calculated for formula: $C_{18}H_{14}N_6 \cdot 3.40HCl \cdot 0.60Et_2O$ C, 50.75; H, 4.89; N, 17.41; Found C, 50.71; H, 4.74; N, 17.34.

1-(4-cyanobenzyl)-5-(2-tetrahydroisoquinolinylmethyl) imidazole hydrochloride

Analysis calculated for formula: $C_{21}H_{20}N_4$ .4.45HCl.0.80 DMF C, 51.18; H, 5.52; N, 12.24; Found C, 51.09; H, 5.25; N, 12.26.

5-(2-benzotriazolylmethyl)-1-(4-cyanobenzyl)imidazole hydrochloride

Analysis calculated for formula: $C_{18}H_{14}N_6 \cdot 1.40HCl \cdot 0.15 Et_2O$ C, 59.33; H, 4.52; N, 22.32; Found C, 59.41; H, 4.38; N, 22.33.

1-(4-cyanobenzyl)-5-(1-isatinylmethyl)imidazole hydrochloride

Analysis calculated for formula: $C_{20}H_{14}N_4O_2 \cdot 1.55HCl$ C, 60.22; H, 3.93; N, 14.05; Found C, 60.31; H, 4.16; N, 14.17.

5-[1-(5-azabenzimidazolyl)methyl]-1-(4-cyanobenzyl) imidazole hydrochloride and 5-[3-(5-azabenzimidazolyl) methyl]-1-(4-cyanobenzyl)imidazole hydrochloride Analysis calculated for formula: $C_{18}H_{14}N_6 \cdot 3.40HCl \cdot 0.60CHCl_3$ C, 43.81; H, 3.56; N, 16.48; Found C, 43.79; H, 3.93; N, 16.17.

Example 36

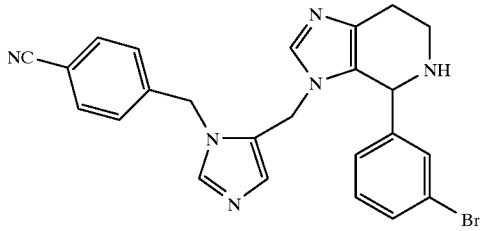

4-{5-[4-(3-Bromophenyl)-4,5,6,7-tetrahydroimidazo [4,5-c]pyridin-1-ylmethyl]imidazol-1-ylmethyl}benzonitrile Step 1: Preparation of 4-(3-bromo-phenyl)-4,5,6,7-tetrahydro-3H-imidazo[4,5-c]pyridine Histamine dihydrochloride (3.68 g, 0.02 mol), KOH (3.36 g, 0.06 mol), and 3-bromobenzaldehyde were dissolved in H₂0 (250 mL) and EtOH(100 mL). The reaction mixture was heated for 24 h at 77° C. open to the atmosphere. The resulting white precipitate was filtered and dried under vacuum at 40° C. to give the title compound.

Step 2: Preparation of 4-(3-bromo-phenyl)-6,7-dihydro-4H-imidazo[4,5-c]pyridine-1,5-dicarboxylic acid di-tert-butyl ester 4-(3-Bromo-phenyl)-4,5,6,7-tetrahydro-3H-imidazo[4,5-c]pyridine (1.0 g, 3.6 mmol), Boc₂O (1.74 g, 7.9 mmol), and Et₃N (1.1 mL, 7.9 mmol) were dissolved in CH₂Cl₂ (35 mL) and stirred overnight at room temperature under Ar. The reaction was washed with H₂O, brine, and dried (Na₂SO₄). Filtration, concentration, and silica gel chromatography (1:6 EtOAc/hexane) yielded the title compound.

Step 3: Preparation of 4-(3-bromo-phenyl)-1,4,6,7-tetrahydro-imidazo[4,5-c]pyridine-5-carboxylic acid tert-butyl ester 4-(3-Bromophenyl)-6,7-dihydro-4H-imidazo[4,5-c] pyridine-1,5-dicarboxylic acid di-tert-butyl ester (0.879 g, 1.83 mmol) and Zn(CN)₂ (0.323 g, 2.75 mmol) were stirred in anh. DMF (30 mL) at 80° C. under Ar for 72 h. The solution was concentrated in vacuo, partitioned between CHCl₃ and sat. NaHCO₃ soln, dried (MgSO₄), filtered, and concentrated to yield the title compound without further purification.

Step 4: Preparation of 4-(3-bromo-phenyl)-1-[3-(4-cyano-benzyl)-H-imidazol-4-ylmethyl]-1 ,4,6,7-tetrahydro-imidazo[4,5-c]pyridine-5-carboxylic acid tert-butyl ester 4-(3-Bromo-phenyl)-1,4,6,7-tetrahydro-imidazo[4,5-c] pyridine-5-carboxylic acid tert-butyl ester (0.160 g, 0.422 mmol) and 5-(chloromethyl)-1-(4-cyanobenzyl)-imidazole hydrochloride, as described in Example 26, Step 1, (0.119 g, 0.444 mmol), were dissolved in DMF (6 mL). NaH (0.62 g, 0.982 mmol) was added, and the reaction mixture was stirred at RT under Ar for 4h. The reaction was concentrated in vacuo and partitioned between CH₂Cl₂ and Sat. NaHCO₃ soln. The aq. layer was back extracted with CH₂Cl₂ (3×) and the combined CH₂Cl₂ layers dried (MgSO₄), filtered and concentrated in vacuo. The residue was chromatographed (2% MeOH/CH₂Cl₂ with NH₄OH) to yield the title compound.

Step 5: Preparation of 4-{5-[4-(3-bromophenyl)-4,5,6,7-tetrahydroimidazo[4,5-c]pyridin-1-ylmethyl]imidazol-1-ylmethyl}-benzonitrile To a solution of 4-(3-bromophenyl)-1-[3-(4-cyanobenzyl)-3H-imidazol-4-ylmethyl]-1,4,6,7-tetrahydroimidazo[4,5-c]pyridine-5-carboxylic acid tert-butyl ester (0.045 g, 0.078 mmol) dissolved in CH₂Cl₂ (5 mL) was added TFA (1 mL) and the reaction mixture was stirred at room temperature under Ar for 2h. The solution was concentrated in vacuo and purified using reverse phase liquid chromatography (95/5 –5/95 H₂O/CH₃CN with 0.1% TFA over 60 min, flow rate =65 mL/min) to yield the title compound.

¹H NMR (CD₃OD); δ 8.75 (d, 1H, J=1 Hz), 7.83 (s, 1H), 7.74 (d, 2H, J=8.5 Hz), 7.70 (d, 1H, J=8 Hz), 7.46 (s, 1H), 7.41 (t, 1H, J=8 Hz), 7.28 (d, 1H, J=8 Hz), 7.21 (d, 2H, J=8.5 Hz), 7.18 (s, 1H), 5.83 (s, 1H), 5.34 (d, 1H, J=16 Hz), 5.27 (d, 1H, J=16 Hz), 4.99 (d, 1H, J=16 Hz), 4.79 (d, 1H, J=16 Hz), 3.43 (t, 2H, J=6 Hz), 3.12–2.96 (m, 2H). High resolution MS, $C_{24}H_{21}BrN_5$: Calc MW, 473.1084. Found, 473.1079.

Example 37

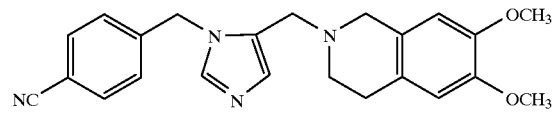

6,7-Dimethoxy-2-(1-(4-cyanobenzyl)-5-imidazolylmethyl) 1,2,3,4-tetrahydroisoquinoline Following the procedure described in Example 1, Step 6 using 6,7-dimethoxy-1,2,3,4-tetrahydroisoquinoline (Aldrich), the title compound was obtained as a colorless gum.

Analysis for $C_{23}H_{24}N_4O_2 \cdot O0.10EtOAc$ Calc'd C, 70.74 H, 6.29 N, 14.10 Found C, 70.75 H, 6.21 N, 13.87

Example 38

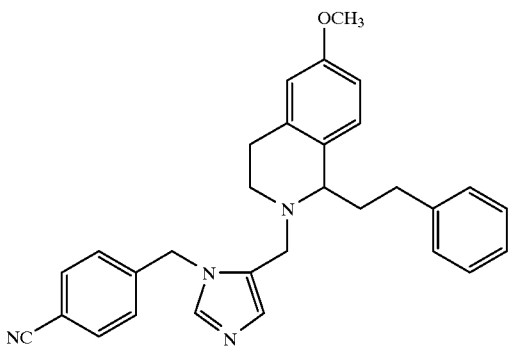

1(R,S)-(2-Phenethyl)-6-methoxy-2-(1-(4-cyanobenzyl)-5-imidazolylmethyl)-1,2,3,4-tetrahydroisoquinoline Step 1: Preparation of N-(2-phenethyl) 2-(3-methoxyphenethyl) amine Following the procedure described in Example 1, Step 6 but using 3-methoxyphenethylamine (2.9 mL, 20 mmol) and 3-phenyl propionyl chloride (6 mL, 40 mmol), the title compound was obtained as a colorless solid, mp. 49–51° C.

FAB ms (M+H) 284.2.

Step 2: Preparation of 1-(2-phenethyl)-6-methoxy-3,4-dihydroisoquinoline

Following the procedure described in Example 25, Step 2 but using the amide from Step 1 (2.83 g, 10 mmol) the title compound was obtained as a colorless gum.

FAB ms (M+H) 266.2.

Step 3: Preparation of 1 (R,S)-(2-phenethyl)-6-methoxy-1,2,3,4-tetrahydroisoquinoline Following the procedure described in Example 25, Step 3 ut using the imine from Step 2 (530 mg, 2 mmol) the title compound as obtained as a colorless gum.

FAB ms (M+H) 268.3.

Step 4: Preparation of 1 (R,S)-(2-Phenethyl)-6-methoxy-2-(1-(4-cyanobenzyl)-5-imidazolylmethyl)-1,2,3,4-tetrahydroisoquinoline Following the procedure described in Example 1, Step 6 but using the product from Step 3, the title compound was obtained as a colorless gum which was then converted to the bis HCl salt.

FAB ms (M+H) 463.3.

Analysis for $C_{30}H_{30}N_4O \cdot 2HCl \cdot 0.20EtOH \cdot 0.70HCl$ Calc'd C, 6402, H, 5.99 N, 9.83 Found C, 64.06, H, 6.33 N, 9.77

Example 39

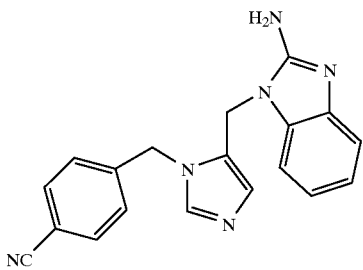

1-(4-Cyanobenzyl)-5-(2-amino-1-benzimidazolylmethyl)imidazole

The compound described in Example 26, Step 1 [1-(4-cyanobenzyl)-5-(chloromethyl)imidazole hydrochloride] (0.75 mmol, 0.20 g), 2-aminobenzimidazole (0.90 mmol, 0.12 g) and diisopropylethylamine (2.25 mmol, 0.29 g) were dissolved in acetonitrile and placed in a nitrogen purged sealed tube and warmed at 80° C. for 18 hr. The precipitate was filtered off to yield 1-(4-cyanobenzyl)-5-(2-amino-1-benzimidazolylmethyl)imidazole.

Structure was confirmed by $^1$H-NMR-NOE. FAB-MS: calc: 328.4 found: 329.1. Elemental analysis. Calc: C, 67.09; H, 5.19; N, 25.22. Found: C, 67.09; H,4.99; N, 25.26.
$^1$H-NMR (CD$_3$OD): δ5.2 (s, 2H), 5.3 (s, 2H), 6.6 ppm (d, 2H), 6.9–7.1 (4H), 7.2 (s, 1H), 7.3 (d, 2H), 7.8 (s, 1H).

Example 40

1-(4-cyanobenzyl)-5-(2-amino-1-(3-benzyl-2-imino-1-benzimidazolylmethyl)imidazole

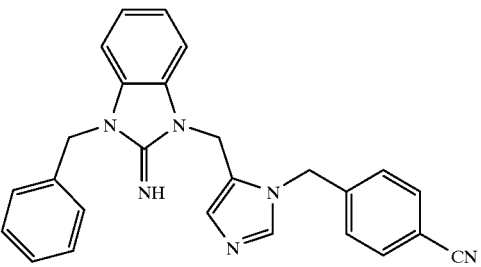

The compound described in Example 26, Step 1, 1-(4-cyanobenzyl)-5-(chloromethyl)imidazole hydrochloride (1.0 mmol, 0.234 g), 2-amino-1-benzylbenzimidazole (1.0 mmol, 0.223 g) and diisopropylethylamine (2.25 mmol, 0.29 g) were dissolved in acetonitrile and placed in a nitrogen purged sealed tube and warmed at 80° C. for 18 hours. The acetonitrile was removed under vacuum and the residue was partitioned between ethylacetate/water. The ethyl acetate layer was separated and the aqueous layer extracted. The combined extracts were washed with water, brine and dried MgSO$_4$. The solvent was removed and a crude mixture obtained. The mixture was purified on $C_{18}$ preparative HPLC column to yield the title compound.

Structure confirmed by $^1$H-NMR-FAB-HRMS $^1$H NMR (CD$_3$OD): 5.35 ppm (s, 2H), 5.63 ppm (s, 2H), 5.73 ppm (s, 2H), 7.29–7.41 ppm (m, 11H), 7.66 ppm (d, 2H), 7.75 ppm (s, 1H), 9.15 ppm (s, 1H).

Theoretical HRMS:419.1979; Measured HRMS:419.1983,

Example 41

In vitro Inhibition of Ras Farnesyl Transferase

Assays of farnesyl-protein transferase. Partially purified bovine FPTase and Ras peptides (Ras-CVLS, Ras-CVIM and Ras-CAIL) were prepared as described by Schaber et al., *J. Biol. Chem.* 265:14701–14704 (1990), Pompliano, et al., *Biochemistry* 31:3800 (1992) and Gibbs et al., *PNAS* U.S.A. 86:6630–6634 (1989), respectively. Bovine FPTase was assayed in a volume of 100 ml containing 100 mM N-(2-hydroxy ethyl) piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 mg/ml FPTase at 31° C. for 60 min. Reactions were initiated with FPTase and stopped with 1 ml of 1.0 M HCL in ethanol. Precipitates were collected onto filter-mats using a TomTec Mach II cell harvestor, washed with 100% ethanol, dried and counted in an LKB b-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., Biochemistry 32:5167–5176 (1993). Human FPTase activity was assayed as described above with the exception that 0.1% (w/v) polyethylene glycol 20,000, 10 mM ZnCl$_2$ and 100 nM Ras-CVIM were added to the reaction mixture. Reactions were performed for 30 min., stopped with 100 ml of 30% (v/v) trichloroacetic acid (TCA) in ethanol and processed as described above for the bovine enzyme.

The compounds of the instant invention described in the above Examples were tested for inhibitory activity against human FPTase by the assay described above and were found to have IC$_{50}$ of <50 µM.

Example 42
Modified In vitro GGTase Inhibition Asssay

The modified geranylgeranyl-protein transferase inhibition assay is carried out at room temperature. A typical reaction contains (in a final volume of 50 mL): [$^3$H] geranylgeranyl diphosphate, biotinylated Ras peptide, 50 mM HEPES, pH 7.5, a modulating anion (for example 10 mM glycerophosphate or 5 mM ATP), 5 mM MgCl$_2$, 10 mM ZnCl$_2$, 0.1% PEG (15–20,000), 2 mM dithiothreitol, and geranylgeranyl-protein transferase type I(GGTase). The GGTase-type I enzyme employed in the assay is prepared as described in U.S. Pat. No. 5,470,832, incorporated by reference. The Ras peptide is derived from the K4B-Ras protein and has the following sequence: biotinyl-GKKKKKKSKTKCVIM (single amino acid code) (SEQ.ID.NO.: 1). Reactions are initiated by the addition of GGTase and stopped at timed intervals (typically 15 min) by the addition of 200 mL of a 3 mg/mL suspension of streptavidin SPA beads (Scintillation Proximity Assay beads, Amersham) in 0.2 M sodium phosphate, pH 4, containing 50 mM EDTA, and 0.5% BSA. The quenched reactions are allowed to stand for 2 hours before analysis on a Packard TopCount scintillation counter.

For inhibition studies, assays are run as described above, except inhibitors are prepared as concentrated solutions in 100% dimethyl sulfoxide and then diluted 25-fold into the enzyme assay mixture. IC$_{50}$ values are determined with Ras peptide near K$_M$ concentrations. Enzyme and nonsaturating substrate conditions for inhibitor IC$_{50}$ determinations are as follows: 75 pM GGTase-I, 1.6 mM Ras peptide, 100 nM geranylgeranyl diphosphate.

Example 43
Cell-based in vitro Ras Prenylation Assay

The cell lines used in this assay consist of either Rat1 or NIH3T3 cells transformed by either viral H-ras; an N-ras chimeric gene in which the C-terminal hypervariable region of viral-H-ras was substituted with the corresponding region from the N-ras gene; or ras-CVLL, a viral-H-ras mutant in which the C-terminal exon encodes leucine instead of serine, making the encoded protein a substrate for geranylgeranylation by GGTase-I. The assay can also be performed using cell lines transformed with human H-ras, N-ras or K4B-ras. The assay is performed essentially as described in DeClue, J. E. et al., Cancer Research 51:712–717, (1991). Cells in 10 cm dishes at 50–75% confluency are treated with the test compound(s) (final concentration of solvent, methanol or dimethyl sulfoxide, is 0.1%). After 4 hours at 37° C., the cells are labelled in 3 ml methionine-free DMEM supplemented with 10% regular DMEM, 2% fetal bovine serum, 400 mCi[$^{35}$S]methionine (1000 Ci/mmol) and test compound(s). Cells treated with lovastatin, a compound that blocks Ras processing in cells by inhibiting the rate-limiting step in the isoprenoid biosynthetic pathway (Hancock, J. F. et al. Cell, 57:1167 (1989); DeClue, J. E. et al. Cancer Res., 51:712 (1991); Sinensky, M. et al. J. Biol. Chem., 265:19937 (1990)), serve as a positive control in this assay. After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Alternatively, four hours after the additon of the labelling media, the media is removed, the cells washed, and 3 ml of media containing the same or a different test compound added. Following an additional 16 hour incubation, the lysis is carried out as above. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., J. Virol. 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to prenylated and nonprenylated Ras proteins are compared to determine the percent inhibition of prenyl transfer to protein.

Example 44
Cell-based in vitro Anchorage Independent Growth Assay (SALSA)

SALSA (Soft Agar-Like Surrogate Assay) measures the inhibition of anchorage-independent growth by prenyltransferase inhibitors. Only transformed cells are able to grow anchorage-independently in the SALSA format. Additionally, cells growing in the SALSA format grow in clumps, resembling the colonies formed in soft agar. SALSA may been used to measure the growth inhibition by prenyltransferase inhibitors in a variety of transformed cell lines, including Rat1 fibroblasts transformed with viral-H-ras (H-ras/rat1), as well as a panel of human tumor cell lines (HTL's).

SALSA is performed in 96-well plates that are coated with a thin film of the polymer, PolyHEMA (Poly(2-hydroxyethyl methacrylate)), which prevents cells from attaching to the plate. Rat1 fibroblast cells transformed with v-Ha-ras (this cell line has been deposited in the ATCC on Aug. 19, 1997 under the terms of the Budapest convention and has been given a designation of ATCCCRL 12387) are seeded at 5000 cells/well, grown for 4 hr, then vehicle or half-log dilutions of test compound (in either an 8 or 12 point titration) are added. The cells are then grown for 6 days at 37 degrees, without changing the growth media or adding fresh compound. At day 6, cell growth is assessed via a colorimetric assay that measures the cleavage of the tetrazolium dye, MTT, to an insoluble purple formazan, a reaction dependent upon mitochondrial dehydrogenases. At day 6, the cells are incubated for 4 hr with 0.5 mg/ml MTT, and then SDS is added to 9% w/v to lyse the cells and solubilize the insoluble MTT-formazan. The amount of MTT metabolism is quantitated via spectrophotometric detection at 570 nM. Dose-inhibition curves and $IC_{50}$'s are determined.

Example 45
Construction of SEAP Reporter Plasmid pDSE100

The SEAP reporter plasmid, pDSE100 was constructed by ligating a restriction fragment containing the SEAP coding sequence into the plasmid pCMV-RE-AKI. The SEAP gene is derived from the plasmid pSEAP2-Basic (Clontech, Palo Alto, Calif.). The plasmid pCMV-RE-AKI was constructed by Deborah Jones (Merck) and contains 5 sequential copies of the 'dyad symmetry response element' cloned upstream of a 'CAT-TATA' (SEQ.ID.NO.: 15) sequence derived from the cytomegalovirus immediate early promoter. The plasmid also contains a bovine growth hormone poly-A sequence.

The plasmid, pDSE100 was constructed as follows. A restriction fragment encoding the SEAP coding sequence was cut out of the plasmid pSEAP2-Basic using the restriction enzymes EcoR1 and HpaI. The ends of the linear DNA fragments were filled in with the Klenow fragment of E. coli DNA Polymerase I. The 'blunt ended' DNA containing the SEAP gene was isolated by electrophoresing the digest in an agarose gel and cutting out the 1694 base pair fragment. The vector plasmid pCMV-RE-AKI was linearized with the restriction enzyme Bgl-II and the ends filled in with Klenow DNA Polymerase I. The SEAP DNA fragment was blunt end ligated into the pCMV-RE-AKI vector and the ligation products were transformed into DH5-alpha E. coli cells (Gibco-BRL). Transformants were screened for the proper insert and then mapped for restriction fragment orientation. Properly oriented recombinant constructs were sequenced across the cloning junctions to verify the correct sequence. The resulting plasmid contains the SEAP coding sequence downstream of the DSE and CAT-TATA promoter elements and upstream of the BGH poly-A sequence.

Cloning of a Myristylated viral-H-ras Expression Plasmid

A DNA fragment containing viral-H-ras can be PCRed from plasmid "H-1" (Ellis R. et al. J. Virol. 36, 408, 1980) using the following oligos.

Sense strand:

5'TCTCCTCGAGGCCACCATGGGGAGTAG-
CAAGAGCAAGCCTAA GGACCCCAGC-
CAGCGCCGGATGACAGAATACAAGCT-
TGTGGTG G 3'. (SEQ.ID.NO.: 2)

Antisense:

5'CACATCTAGATCAGGACAGCACAGACT-
TGCAGC 3'. (SEQ.ID.NO.: 3)

A sequence encoding the first 15 aminoacids of the v-src gene, containing a myristylation site, is incorporated into the sense strand oligo. The sense strand oligo also optimizes the 'Kozak' translation initiation sequence immediately 5' to the ATG start site.To prevent prenylation at the viral-ras C-terminus, cysteine 186 would be mutated to a serine by substituting a G residue for a C residue in the C-terminal antisense oligo. The PCR primer oligos introduce an XhoI site at the 5' end and a XbaI site at the 3' end. The XhoI-XbaI fragment can be ligated into the mammalian expression plasmid pCI (Promega) cut with XhoI and XbaI. This results in a plasmid in which the recombinant myr-viral-H-ras gene is constitutively transcribed from the CMV promoter of the pCI vector.

Cloning of a viral-H-ras-CVLL Expression Plasmid

A viral-H-ras clone with a C-terminal sequence encoding the amino acids CVLL can be cloned from the plasmid "H-1" (Ellis R. et al. J. Virol. 36, 408, 1980) by PCR using the following oligos.

Sense strand:
5'TCTCCTCGAGGCCACCATGACAGAATACAAGCT
TGTGGTGG-3' (SEQ.ID.NO.: 4)

Antisense strand:
5'CACTCTAGACTGGTGTCAGAGCAGCACA-
CACTTG
CAGC-3' (SEQ.ID.NO.: 5)

The sense strand oligo optimizes the 'Kozak' sequence and adds an XhoI site. The antisense strand mutates serine 189 to leucine and adds an XbaI site. The PCR fragment can be trimmed with XhoI and XbaI and ligated into the XhoI-XbaI cut vector pCI (Promega). This results in a plasmid in which the mutated viral-H-ras-CVLL gene is constitutively transcribed from the CMV promoter of the pCI vector.

Cloning of c-H-ras-Leu61 Expression Plasmid

The human c-H-ras gene can be PCRed from a human cerebral cortex cDNA library (Clontech) using the following oligonucleotide primers.

Sense strand:
5'-GAGAGAATTCGCCACCATGACGGAATATAAGCT
GGTGG-3' (SEQ.ID.NO.: 6)

Antisense strand:
5'-GAGAGTCGACGCGTCAGGAGAGCACACACTTG
C-3' (SEQ.ID.NO.: 7)

The primers will amplify a c-H-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-H-ras fragment can be ligated ligated into an EcoRI -Sal I cut mutagenesis vector pAlter-1 (Promega). Mutation of glutamine-61 to a leucine can be accomplished using the manufacturer's protocols and the following oligonucleotide:

5'-CCGCCGGCCTGGAGGAGTACAG-3'
(SEQ.ID.NO.: 8)

After selection and sequencing for the correct nucleotide substitution, the mutated c-H-ras-Leu61 can be excised from the pAlter-1 vector, using EcoRI and Sal I, and be directly ligated into the vector pCI (Promega) which has been digested with EcoRI and Sal I. The new recombinant plasmid will constitutively transcribe c-H-ras-Leu61 from the CMV promoter of the pCI vector.

Cloning of a c-N-ras-Val-12 Expression Plasmid

The human c-N-ras gene can be PCRed from a human cerebral cortex cDNA library (Clontech) using the following oligonucleotide primers.

Sense strand:
5'-GAGAGAATTCGCCACCATGACTGAGT
ACAAACT
GGTGG-3' (SEQ.ID.NO.: 9)

Antisense strand:
5'-GAGAGTCGACTTGTTACATCACCACACATGGC-
3' (SEQ.ID.NO.: 10)

The primers will amplify a c-N-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-N-ras fragment can be ligated into an EcoRI -Sal I cut mutagenesis vector pAlter-1 (Promega). Mutation of glycine-12 to a valine can be accomplished using the manufacturer's protocols and the following oligonucleotide:

5'-GTTGGAGCAGTTGGTGTTGGG-3' (SEQ.ID.NO.: 11)

After selection and sequencing for the correct nucleotide substitution, the mutated c-N-ras-Val-12 can be excised from the pAlter-1 vector, using EcoRI and Sal I, and be directly ligated into the vector pCI (Promega) which has been digested with EcoRI and Sal I. The new recombinant plasmid will constitutively transcribe c-N-ras-Val-12 from the CMV promoter of the pCI vector.

Cloning of a c-K-ras-Val-12 Expression Plasmid

The human c-K-ras gene can be PCRed from a human cerebral cortex cDNA library (Clontech) using the following oligonucleotide primers.

Sense strand:
5'-GAGAGGTACCGCCACCATGACTGAATAT AAACTTGTGG-3' (SEQ.ID.NO.: 12)

Antisense strand:
5'-CTCTGTCGACGTATTTACATAATTACACA CTTTGTC-3' (SEQ.ID.NO.: 13)

The primers will amplify a c-K-ras encoding DNA fragment with the primers contributing an optimized 'Kozak' translation start sequence, a KpnI site at the N-terminus and a Sal I stite at the C-terminal end. After trimming the ends of the PCR product with Kpn I and Sal I, the c-K-ras fragment can be ligated into a KpnI -Sal I cut mutagenesis vector pAlter-1 (Promega). Mutation of cysteine-12 to a valine can be accomplished using the manufacturer's protocols and the following oligonucleotide:

5'-GTAGTTGGAGCTGTTGGCGTAGGC-3' (SEQ.ID.NO.: 14)

After selection and sequencing for the correct nucleotide substitution, the mutated c-K-ras-Val-12 can be excised from the pAlter-1 vector, using KpnI and Sal I, and be directly ligated into the vector pCI (Promega) which has been digested with KpnI and Sal I. The new recombinant plasmid will constitutively transcribe c-K-ras-Val-12 from the CMV promoter of the pCI vector.

Seap Assay

Human C33A cells (human epitheial carcenoma—ATTC collection) are seeded in 10 cm tissue culture plates in DMEM+10% fetal calf serum+1× Pen/Strep+1× glutamine+ 1× NEAA. Cells are grown at 37° C. in a 5% $CO_2$ atmosphere until they reach 50–80% of conflunecy.

The transient transfection is performed by the $CaPO_4$ method (Sambrook et al., 1989). Thus, expression plasmids for H-ras, N-ras, K-ras, Myr-ras or H-ras-CVLL are co-precipitated with the DSE-SEAP reporter construct. For 10 cm plates 600 ml of $CaCl_2$-DNA solution is added dropwise while vortexing to 600 ml of 2× HBS buffer to give 1.2 ml of precipitate solution (see recipes below). This is allowed to sit at room temperature for 20 to 30 minutes. While the precipitate is forming, the media on the C33A cells is replaced with DMEM (minus phenol red; Gibco cat. #31053-028)+0.5% charcoal stripped calf serum+1× (Pen/ Strep, Glutamine and nonessential aminoacids). The $CaPO_4$- DNA precipitate is added dropwise to the cells and the plate rocked gently to distribute. DNA uptake is allowed to proceed for 5–6 hrs at 37° C. under a 5% $CO_2$ atmosphere.

Following the DNA incubation period, the cells are washed with PBS and trypsinized with 1 ml of 0.05% trypsin. The 1 ml of trypsinized cells is diluted into 10 ml of phenol red free DMEM+0.2% charcoal stripped calf serum+ 1× (Pen/Strep, Glutamine and NEAA). Transfected cells are plated in a 96 well microtiter plate (100 ml/well) to which drug, diluted in media, has already been added in a volume of 100 ml. The final volume per well is 200 ml with each drug concentration repeated in triplicate over a range of half-log steps.

Incubation of cells and drugs is for 36 hrs at 37° under $CO_2$. At the end of the incubation period, cells are examined microscopically for evidence of cell distress. Next, 100 ml of media containing the secreted alkaline phosphatase is removed from each well and transferred to a microtube array for heat treatment at 65° C. for 1 hr to inactivate endogenous alkaline phosphatases (but not the heat stable secreted phosphatase).

The heat treated media is assayed for alkaline phosphatase by a luminescence assay using the luminescence reagent CSPD® (Tropix, Bedford, Mass.). A volume of 50 ml media is combinRased with 200 ml of CSPD cocktail and incubated for 60 minutes at room temperature. Luminesence is monitored using an ML2200 microplate luminometer (Dynatech). Luminescence reflects the level of activation of the fos reporter construct stimulated by the transiently expressed protein.

| $DNA-CaPO_4$ precipitate for 10 cm. plate of cells | |
| --- | --- |
| Ras expression plasmid (1 mg/ml) | 10 ml |
| DSE-SEAP Plasmid (1 mg/ml) | 2 ml |
| Sheared Calf Thymus DNA (1 mg/ml) | 8 ml |
| 2M $CaCl_2$ | 74 ml |
| $dH_2O$ | 506 ml |

2× HBS Buffer
280 mM NaCl
10 mM KCl
1.5 mM $Na_2HPO_4$ $2H_2O$
12 mM dextrose
50 mM HEPES
Final pH=7.05

| Luminesence Buffer (26 ml) | |
| --- | --- |
| Assay Buffer | 20 ml |
| Emerald Reagent ™ (Tropix) | 2.5 ml |
| 100 mM homoarginine | 2.5 ml |
| CSPD Reagent ® (Tropix) | 1.0 ml |

Assay Buffer
Add 0.05M $Na_2CO_3$ to 0.05M $NaHCO_3$ to obtain pH 9.5. Make 1 mM in $MgCl_2$ Example 46

In Vivo Tumor Growth Inhibition Assay (nude mouse)

In vivo efficacy as an inhibitor of the growth of cancer cells may be confirmed by several protocols well known in the art. Examples of such in vivo efficacy studies are described by N. E. Kohl et al. (*Nature Medicine*, 1:792–797 (1995)) and N. E. Kohl et al. (*Proc. Nat. Acad. Sci. U.S.A.*, 91:9141–9145 (1994)).

Rodent fibroblasts transformed with oncogenically mutated human Ha-ras or Ki-ras ($10^6$ cells/animal in 1 ml of DMEM salts) are injected subcutaneously into the left flank of 8–12 week old female nude mice (Harlan) on day 0. The mice in each oncogene group are randomly assigned to a vehicle, compound or combination treatment group. Animals are dosed subcutaneously starting on day 1 and daily for the duration of the experiment. Alternatively, the farnesyl-protein transferase inhibitor may be administered by a continuous infusion pump. Compound, compound combination or vehicle is delivered in a total volume of 0.1 ml. Tumors are excised and weighed when all of the vehicle-treated animals exhibited lesions of 0.5–1.0 cm in diameter, typically 11–15 days after the cells were injected. The average weight of the tumors in each treatment group for each cell line is calculated.

What is claimed is:

1. A compound which inhibits farnesyl-protein transferase of the formula I:

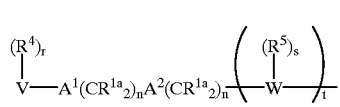

I

-continued

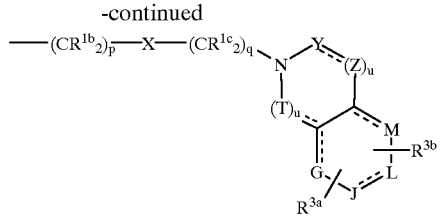

wherein:

$R^{1a}$, $R^{1b}$ and $R^{1c}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, $N_3$, —$N(R^8)_2$, or $R^9OC(O)NR^8$—,
c) $C_1$–$C_6$ alkyl unsubstituted or substituted by unsubstituted or substituted aryl, heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)$—$NR^8$—, provided that $R^{1a}$ is not unsubstituted or substituted imidazolyl;

$R^{2a}$, $R^{2b'}$ and $R^{2b''}$ are independently hydrogen, $NH_2$ or —$(CR^{11}_2)_v A^3 (CR^{12}_2)_w R^{13}$; or $R^{2b'}$ and $R^{2b''}$ are combined as O;

$R^{3a}$ and $R^{3b}$ are independently selected from:
a) hydrogen,
b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8_2N$—$C(NR^8)$—, CN, $NO_2$, $R^8C(O)$—, $N_3$, —$N(R^8)_2$, or $R^9OC(O)NR^8$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8_2N$—$C(NR^8)$—, CN, $R^8C(O)$—, $N_3$, —$N(R^8)_2$, and $R^9OC(O)$—$NR^8$—;

$R^4$ is independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $R^8_2N$—$C(NR^8)$—, $R^8C(O)$—, $R^8OC(O)$—, $N_3$, —$N(R^8)_2$, or $R^9OC(O)NR^8$—, and
c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, CN, $H_2N$—$C(NH)$—, $R^8C(O)$—, $R^8OC(O)$—, $N_3$, —$N(R^8)_2$, or $R^8OC(O)NH$—, provided that $R^4$ is not unsubstituted or substituted imidazolyl;

$R^5$ is independently selected from:
a) hydrogen,
b) $C_2$–$C_6$ alkenyl, $C_2$–$C_6$ alkynyl, $C_3$–$C_6$ cycloalkyl, perfluoroalkyl, F, Cl, Br, $R^8O$—, $R^9S(O)_m$—, $R^8C(O)NR^8$—, CN, $NO_2$, $(R^8)_2N$—$C$—$(NR^8)$—, $R^8C(O)$—, $R^8OC(O)$—, $N_3$, —$N(R^8)_2$, or $R^9OC(O)NR^8$—, and
c) $C_1$–$C_6$ alkyl, unsubstituted or substituted by perfluoroalkyl, F, Cl, Br, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)NR^8$—;

$R^8$ is independently selected from hydrogen, $C_1$–$C_6$ alkyl, benzyl, 2,2,2-trifluoroethyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:
a) $C_{1-4}$ alkoxy,
b) aryl or heterocycle,
c) halogen,
d) HO, e) 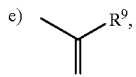

f) 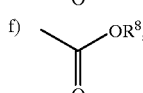

g) 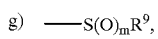

h) $N(R^8)_2$, or
i) $C_{3-6}$ cycloalkyl;

$R^{11}$ and $R^{12}$ are independently selected from:
a) hydrogen,
b) $C_1$–$C_6$ alkyl unsubstituted or substituted by $C_2$–$C_{20}$ alkenyl, $R^8O$—, $R^9S(O)_m$—, $R^8C(O)NR^8$—, CN, $N_3$, $(R^8)_2N$—$C(NR^8)$—, $R^8C(O)$—, —$N(R^8)_2$, or $R^9OC(O)NR^8$—,
c) unsubstituted or substituted aryl, unsubstituted or substituted heterocycle, $C_3$–$C_{10}$ cycloalkyl, $C_2$–$C_{20}$ alkenyl, halogen, $R^8O$—, $R^9S(O)_m$—, $R^8C(O)NR^8$—, CN, $NO_2$, $(R^8)_2N$—$C(NR^8)$—, $R^8C(O)$—, $N_3$, —$N(R^8)_2$, or $R^9OC(O)NR^8$—, and
d) $C_1$–$C_6$ alkyl substituted with an unsubstituted or substituted group selected from aryl, heterocyclic and $C_3$–$C_{10}$ cycloalkyl;

$R^{13}$ is selected from:
a) hydrogen,
b) substituted or unsubstituted aryl, substituted or unsubstituted heterocycle, $C_3$–$C_{10}$ cycloalkyl, $C_2$–$C_{20}$ alkenyl, $C_2$–$C_{20}$ alkynyl, $C_1$–$C_{20}$ perfluoroalkyl, allyloxy, F, Cl, Br, $R^8O$—, $R^9S(O)_m$—, $R^8C(O)NR^8$—, CN, $NO_2$, $R^8_2N$—$C(NR^8)$—, $R^8C(O)$—, $N_3$, —$N(R^8)_2$, $(R^9)_2NC(O)$— or $R^9OC(O)NR^8$—, and
c) $C_1$–$C_6$ alkyl unsubstituted or substituted by substituted or unsubstituted aryl, substituted or unsubstituted heterocycle, $C_3$–$C_{10}$ cycloalkyl, $C_2$–$C_{20}$ alkenyl, $C_2$–$C_{20}$ alkynyl, $C_2$–$C_{20}$ perfluoroalkyl, F, Cl, Br, $R^8O$—, $R^9S(O)_m$—, $R^8C(O)NH$—, CN, $H_2N$—$C(NH)$—, $R^8C(O)$—, $N_3$, —$N(R^8)_2$, or $R^9OC(O)NH$—;

$A^1$ and $A^2$ are independently selected from: a bond, —CH=CH—, —C≡C—, —C(O)—, —$C(O)NR^8$—, —$NR^8C(O)$—, O, —$N(R^8)$—, —$S(O)_2N(R^8)$—, —$N(R^8)S(O)_2$—, or —$S(O)_m$;

$A^3$ are independently selected from: a bond, —CH=CH—, —C≡C—, —C(O)—, —$C(O)NR^{10}$—, —$NR^{10}C(O)$—, O, —$N(R^{10})$—, —$S(O)_2N(R^{10})$—, —$N(R^{10})S(O)_2$—, or $S(O)_m$;

G, J, L and M are independently selected from: $CH_y$ or N;

T is selected from: N, $CR^{2b'}$ or $CR_{2b'} R^{2b''}$;

V is selected from:

a) heterocycle,
b) aryl,
c) $C_1$–$C_{20}$ alkyl wherein from 1 to 4 carbon atoms are replaced with a heteroatom selected from O, S, and N, and
d) $C_2$–$C_{20}$ alkenyl;
and provided that V is not imidazolyl;

W is a heterocycle;
X is a bond, —S(O)$_m$—, O or —C(=O)—;
Y is selected from: $CR^{2a}$, C=O, C=NH or N;
Z is selected from: $CR^{2a}$, C=O or N;
m is 0, 1 or 2;
n is 0, 1, 2, 3 or 4;
p is 0, 1, 2, 3 or 4;
q is 0, 1, 2, 3 or 4, provided that q is not 0 or 1 if X is O;
r is 0 to 5;
s is 1 or 2;
t is 1;
u is independently 0,1 or 2;
v is 0, 1, 2, 3 or 4, provided that v is not 0 when $A^3$ is —$NR^{10}C(O)$—, O, —$N(R^{10})$—, —$S(O)_2N(R^{10})$—, —$N(R^{10})S(O)_2$—, or $S(O)_m$;
w is 0, 1, 2, 3or 4; and
y is 1 or 2;

the dashed lines represent optional double bonds;
or an optical isomer or a pharmaceutically acceptable salt thereof.

2. The compound according to claim 1 which inhibits farnesyl-protein transferase of the formula A:

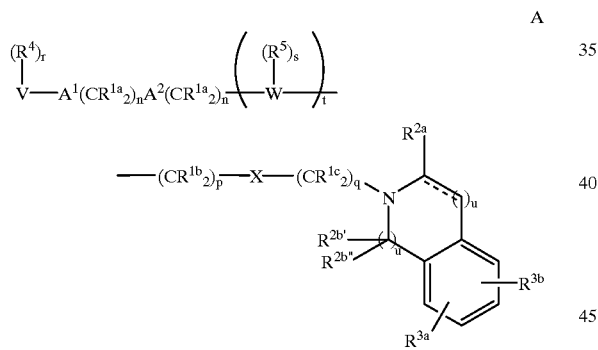

wherein:
$R^{1a}$, $R^{1b}$ and $R^{1c}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, $N_3$, —$N(R^8)_2$, or $R^9OC(O)NR^8$—,
c) $C_1$–$C_6$ alkyl unsubstituted or substituted by unsubstituted or substituted aryl, heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—C(NR$^8$)—, $R^8C(O)$—, $R^8OC(O)$—, $N_3$, —$N(R^8)_2$, or $R^9OC(O)$—$NR^8$—, provided that $R^{1a}$ is not unsubstituted or substituted imidazolyl;

$R^{2a}$, $R^{2b'}$ and $R^{2b''}$ are independently hydrogen or —$(CR^{11}_2)_vA^3(CR^{12}_2)_wR^{13}$; or
$R^{2b'}$ and $R^{2b''}$ are combined as O;

$R^{3a}$ and $R^{3b}$ are independently selected from:
a) hydrogen,
b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8_2N$—$C(NR^8)$—, CN, $NO_2$, $R^8C(O)$—, $N_3$, —$N(R^8)_2$, or $R^9OC(O)NR^8$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8_2N$—$C(NR^8)$—, CN, $R^8C(O)$—, $N_3$, —$N(R^8)_2$, and $R^9OC(O)$—$NR^8$—;

$R^4$ is independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $R^8_2N$—$C(NR^8)$—, $R^8C(O)$—, $R^8OC(O)$—, $N_3$, —$N(R^8)_2$, or $R^9OC(O)NR^8$—, and
c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, CN, $H_2N$—C(NH)—, $R^8C(O)$—, $R^8OC(O)$—, $N_3$, —$N(R^8)_2$, or $R^8OC(O)NH$—, provided that $R^4$ is not unsubstituted or substituted imidazolyl;

$R^5$ is independently selected from:
a) hydrogen,
b) $C_2$–$C_6$ alkenyl, $C_2$–$C_6$ alkynyl, $C_3$–$C_6$ cycloalkyl, perfluoroalkyl, F, Cl, Br, $R^8O$—, $R^9S(O)_m$—, $R^8C(O)NR^8$—, CN, $NO_2$, $(R^8)_2N$—C—(NR$^8$)—, $R^8C(O)$—, $R^8OC(O)$—, $N_3$, —$N(R^8)_2$, or $R^9OC(O)NR^8$—, and
c) $C_1$–$C_6$ alkyl, unsubstituted or substituted by perfluoroalkyl, F, Cl, Br, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)NR^8$—;

$R^8$ is independently selected from hydrogen, $C_1$–$C_6$ alkyl, benzyl, 2,2,2-trifluoroethyl and aryl;
$R^9$ is independently selected from $C_1$–$C_6$ alkyl and aryl;
$R^{10}$ is selected from: H; $R^8C(O)$—; $R^9S(O)_m$—; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:
a) $C_{1-4}$ alkoxy,
b) aryl or heterocycle,
c) halogen,
d) HO, e) 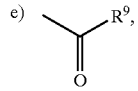

-continued f) 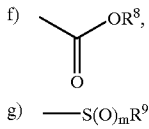

g) —S(O)$_m$R$^9$, h) N(R$^8$)$_2$, or i) C$_{3-6}$ cycloalkyl;

R$^{11}$ and R$^{12}$ are independently selected from:
 a) hydrogen,
 b) C$_1$–C$_6$ alkyl unsubstituted or substituted by C$_2$–C$_{20}$ alkenyl, R$^8$O—, R$^9$S(O)$_m$—, R$^8$C(O)NR$^8$—, CN, N$_3$, (R$^8$)$_2$N—C(NR$^8$)—, R$^8$C(O)—, —N(R$^8$)$_2$, or R$^9$OC(O)NR$^8$—,
 c) unsubstituted or substituted aryl, unsubstituted or substituted heterocycle, C$_3$–C$_{10}$ cycloalkyl, C$_2$–C$_{20}$ alkenyl, halogen, R$^8$O—, R$^9$S(O)$_m$—, R$^8$C(O)NR$^8$—, CN, NO$_2$, (R$^8$)$_2$N—C(NR$^8$)—, R$^8$C(O)—, N$_3$, —N(R$^8$)$_2$, or R$^9$OC(O)NR$^8$—, and
 d) C$_1$–C$_6$ alkyl substituted with an unsubstituted or substituted group selected from aryl, heterocyclic and C$_3$–C$_{10}$ cycloalkyl;

R$^{13}$ is selected from:
 a) hydrogen,
 b) substituted or unsubstituted aryl, substituted or unsubstituted heterocycle, C$_3$–C$_{10}$ cycloalkyl, C$_2$–C$_{20}$ alkenyl, C$_2$–C$_{20}$ alkynyl, C$_1$–C$_{20}$ perfluoroalkyl, allyloxy, F, Cl, Br, R$^8$O—, R$^9$S(O)$_m$—, R$^8$C(O)NR$^8$—, CN, NO$_2$, R$^8_2$N—C(NR$^8$)—, R$^8$C(O)—, N$_3$, —N(R$^8$)$_2$, (R$^9$)$_2$NC(O)— or R$^9$OC(O)NR$^8$—, and
 c) C$_1$–C$_6$ alkyl unsubstituted or substituted by substituted or unsubstituted aryl, substituted or unsubstituted heterocycle, C$_3$–C$_{10}$ cycloalkyl, C$_2$–C$_{20}$ alkenyl, C$_2$–C$_{20}$ alkynyl, C$_2$–C$_{20}$ perfluoroalkyl, F, Cl, Br, R$^8$O—, R$^9$S(O)$_m$—, R$^8$C(O)NH—, CN, H$_2$N—C(NH)—, R$^8$C(O)—, N$_3$, —N(R$^8$)$_2$, or R$^9$OC(O)NH—;

A$^1$ and A$^2$ are independently selected from: a bond, —CH=CH—, —C≡C—, —C(O)—, —C(O)NR$^8$—, —NR$^8$C(O)—, O, —N(R$^8$)—, —S(O)$_2$N(R$^8$)—, —N(R$^8$)S(O)$_2$—, or —S(O)$_m$;

A$^3$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

V is selected from:
 a) heterocycle,
 b) aryl,
 c) C$_1$–C$_{20}$ alkyl wherein from 1 to 4 carbon atoms are replaced with a heteroatom selected from O, S, and N, and
 d) C$_2$–C$_{20}$ alkenyl;
and provided that V is not imidazolyl;

W is a heterocycle;

X is a bond, —S(O)$_m$—, O or —C(=O)—;

m is 0, 1 or 2;

n is 0, 1, 2, 3 or 4;

p is 0, 1, 2, 3 or 4;

q is 0, 1, 2, 3 or 4, provided that q is not 0 or 1 if X is O;

r is 0 to 5;

s is 1 or 2;

t is 1;

u is independently 0, 1 or 2;

v is 0, 1, 2, 3 or 4, provided that v is not 0 when A$^3$ is —NR$^{10}$C(O)—, O, —N(R$^{10}$)—, —S(O)$_2$N(R$^{10}$)—, —N(R$^{10}$)S(O)$_2$—, or S(O)$_m$;

w is 0, 1, 2, 3 or 4; and the dashed lines represent optional double bonds;
or an optical isomer or a pharmaceutically acceptable salt thereof.

3. The compound according to claim 2 which inhibits farnesyl-protein transferase of the formula A:

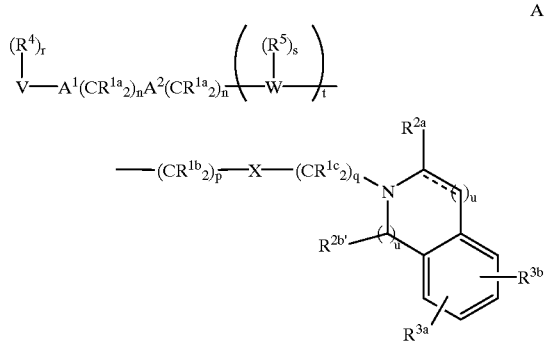

wherein:

R$^{1a}$ and R$^{1c}$ are independently selected from: hydrogen, C$_3$–C$_{10}$ cycloalkyl, R$^8$O—, —N(R$^8$)$_2$, F or C$_1$–C$_6$ alkyl;

R$^{1b}$ is independently selected from:
 a) hydrogen,
 b) unsubstituted or substituted aryl, unsubstituted or substituted heterocycle, C$_3$–C$_6$ cycloalkyl, R$^8$O—, —N(R$^8$)$_2$ or C$_2$–C$_6$ alkenyl,
 c) C$_1$–C$_6$ alkyl unsubstituted or substituted by unsubstituted or substituted aryl, heterocycle, C$_3$–C$_6$ cycloalkyl, C$_2$–C$_6$ alkenyl, R$^8$O—, or —N(R$^8$)$_2$;

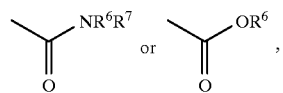

R$^{2a}$ and R$_{2b}$ are independently selected from: H; C$_1$–C$_6$ alkyl,

R$^{3a}$ and R$^{3b}$ are independently selected from:
 a) hydrogen,
 b) unsubstituted or substituted aryl, unsubstituted or substituted heterocycle, unsubstituted or substituted C$_3$–C$_{10}$ cycloalkyl, unsubstituted or substituted C$_2$–C$_6$ alkenyl, C$_2$–C$_6$ alkynyl, halogen, C$_1$–C$_6$ perfluoroalkyl, R$^9$O—, R$^9$S(O)$_m$—, R$^8$C(O)NR$^8$—, (R$^8$)$_2$NC(O)—, R$^9$C(O)O—, R$^8_2$N—C(NR$^8$)—, CN, NO$_2$, R$^8$C(O)—, N$_3$, —N(R$^8$)$_2$, or R$^9$OC(O)NR$^8$—,
 c) unsubstituted C$_1$–C$_6$ alkyl,
 d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^9$O—, R$^9$S(O)$_m$—, R$^8$C(O)NR$^8$—, (R$^8$)$_2$NC(O)—, R$^8_2$N—C(NR$^8$)—, CN, R$^8$C(O)—, N$_3$, —N(R$^8$)$_2$, and R$^9$OC(O)—NR$^8$—;

R$^4$ is independently selected from:
 a) hydrogen,
 b) C$_1$–C$_6$ alkyl, C$_2$–C$_6$ alkenyl, C$_2$–C$_6$ alkynyl, C$_1$–C$_6$ perfluoroalkyl, F, Cl, R$^8$O—, R$^8$C(O)NR$^8$—, CN, NO$_2$, (R$^8$)$_2$N—C(NR$^8$)—, R$^8$C(O)—, R$^8$OC(O)—, —N(R$^8$)$_2$, or R$^9$OC(O)NR$^8$—, and
c) C$_1$–C$_6$ alkyl substituted by C$_1$–C$_6$ perfluoroalkyl, R$^8$O—, R$^8$C(O)NR$^8$—, (R$^8$)$_2$N—C(NR$^8$)—, R$^8$C(O)—, R$^8$OC(O)—, —N(R$^8$)$_2$, or R$^9$OC(O)NR$^8$—;

R$^5$ is selected from:
a) hydrogen,
b) C$_2$–C$_6$ alkenyl, C$_2$–C$_6$ alkynyl, C$_3$–C$_6$ cycloalkyl, C$_1$–C$_6$ perfluoroalkyl, F, Cl, R$^8$O—, R$^9$S(O)$_m$—, R$^8$C(O)NR$^8$—, CN, NO$_2$, (R$^8$)$_2$N—C(NR$^8$)—, R$^8$C(O)—, R$^8$OC(O)—, —N(R$^8$)$_2$, or R$^9$OC(O)NR$^8$—, and
c) C$_1$–C$_6$ alkyl unsubstituted or substituted by C$_1$–C$_6$ perfluoroalkyl, F, Cl, R$^8$O—, R$^9$S(O)$_m$, R$^8$C(O)NR$^8$—, CN, (R$^8$)$_2$N—C(NR$^8$)—, R$^8$C(O)—, R$^8$OC(O)—, —N(R$^8$)$_2$, or R$^9$OC(O)NR$^8$—;

R$^6$ and R$^7$ are independently selected from:
H; C$_{1-4}$ alkyl, C$_{3-6}$ cycloalkyl, aryl, heterocycle, unsubstituted or substituted with one or two:
a) C$_{1-4}$ alkoxy,
b) halogen, or
c) substituted or unsubstituted aryl or substituted or unsubstituted heterocycle, R$^8$ is independently selected from hydrogen, C$_1$–C$_6$ alkyl, benzyl, 2,2,2-trifluoroethyl and aryl;

R$^9$ is independently selected from C$_1$–C$_6$ alkyl and aryl;

A$^1$ and A$^2$ are independently selected from: a bond, —CH=CH—, —C≡C—, —C(O)—, —C(O)NR$^8$—, O, —N(R$^8$)—, or —S(O)$_m$;

V is selected from:
a) heterocycle selected from pyrrolidinyl, imidazolyl, pyridinyl, thiazolyl, indolyl, quinolinyl, isoquinolinyl, and thienyl, and
b) aryl;

W is a heterocycle selected from pyrrolidinyl, triazolyl, imidazolyl, pyridinyl, thiazolyl, indolyl, quinolinyl, or isoquinolinyl;

X is a bond, —S(O)$_m$—, O or —C(=O)—;
m is 0, 1 or 2;
n is 0, 1, 2, 3 or 4;
p is 1, 2 or 3;
q is 0, 1 or 2, provided that q is not 0 or 1 if X is O;
r is 0 to 5;
s is 1 or 2;
t is 1; and
u is independently 0 or 1;
or an optical isomer or a pharmaceutically acceptable salt thereof.

4. The compound according to claim 1 which inhibits farnesyl-protein transferase of the formula A1:

wherein
R$_{1a}$ and R$^{1c}$ are independently selected from: hydrogen, C$_3$–C$_{10}$ cycloalkyl, R$^8$O—, —N(R$^8$)$_2$, F or C$_1$–C$_6$ alkyl;

R$^{1b}$ is independently selected from:
a) hydrogen,
b) unsubstituted or substituted aryl, unsubstituted or substituted heterocycle, C$_3$–C$_6$ cycloalkyl, R$^8$O—, —N(R$^8$)$_2$ or C$_2$–C$_6$ alkenyl,
c) C$_1$–C$_6$ alkyl unsubstituted or substituted by unsubstituted or substituted aryl, heterocycle, C$_3$–C$_6$ cycloalkyl, C$_2$–C$_6$ alkenyl, R$^8$O—, or —N(R$^8$)$_2$;

R$^{2a}$ is selected from: H; C$_1$–C$_6$ alkyl, NH$_2$

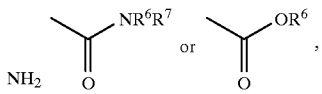

R$^{3a}$ and R$^{3b}$ are independently selected from:
a) hydrogen,
b) unsubstituted or substituted aryl, unsubstituted or substituted heterocycle, unsubstituted or substituted C$_3$–C$_{10}$ cycloalkyl, unsubstituted or substituted C$_2$–C$_6$ alkenyl, C$_2$–C$_6$ alkynyl, halogen, C$_1$–C$_6$ perfluoroalkyl, R$^9$O—, R$^9$S(O)$_m$—, R$^8$C(O)NR$^8$—, (R$^8$)$_2$NC(O)—, R$^9$C(O)O—, R$^8$$_2$N—C(NR$^8$)—, CN, NO$_2$, R$^8$C(O)—, N$_3$, —N(R$^8$)$_2$, or R$^9$OC(O)NR$^8$—,
c) unsubstituted C$_1$–C$_6$ alkyl,
d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^9$O—, R$^9$S(O)$_m$—, R$^8$C(O)NR$^8$—, (R$^8$)$_2$NC(O)—, R$^8$$_2$N—C(NR$^8$)—, CN, R$^8$C(O)—, N$_3$, —N(R$^8$)$_2$, and R$^9$OC(O)—NR$^8$—;

R$^4$ is independently selected from:
a) hydrogen,
b) C$_1$–C$_6$ alkyl, C$_2$–C$_6$ alkenyl, C$_2$–C$_6$ alkynyl, C$_1$–C$_6$ perfluoroalkyl, F, Cl, R$^8$O—, R$^8$C(O)NR$^8$—, CN, NO$_2$, (R$^8$)$_2$N—C(NR$^8$)—, R$^8$C(O)—, R$^8$OC(O)—, —N(R$^8$)$_2$, or R$^9$OC(O)NR$^8$—, and
c) C$_1$–C$_6$ alkyl substituted by C$_1$–C$_6$ perfluoroalkyl, R$^8$O—, R$^8$C(O)NR$^8$—, (R$^8$)$_2$N—C(NR$^8$)—, R$^8$C(O)—, R$^8$OC(O)—, —N(R$^8$)$_2$, or R$^9$OC(O)NR$^8$—;

R$^5$ is selected from:
a) hydrogen,
b) C$_2$–C$_6$ alkenyl, C$_2$–C$_6$ alkynyl, C$_3$–C$_6$ cycloalkyl, C$_1$–C$_6$ perfluoroalkyl, F, Cl, R$^8$O—, R$^9$S(O)$_m$—, R$^8$C(O)NR$^8$—, CN, NO$_2$, (R$^8$)$_2$N—C(NR$^8$)—, R$^8$C(O)—, R$^8$OC(O)—, —N(R$^8$)$_2$, or R$^9$OC(O)NR$^8$—, and
c) C$_1$–C$_6$ alkyl unsubstituted or substituted by C$_1$–C$_6$ perfluoroalkyl, F, Cl, R$^8$O—, R$^9$S(O)$_m$, R$^8$C(O)

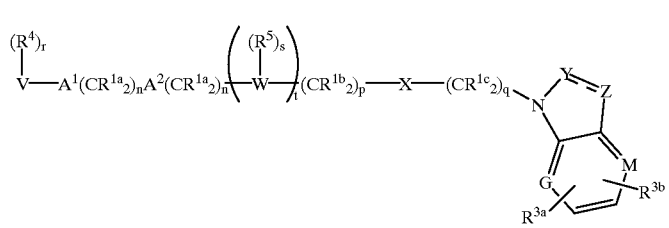

A1

NR⁸—, CN, (R⁸)₂N—C(NR⁸)—, R⁸C(O)—, R⁸OC(O)—, —N(R⁸)₂, or R⁹OC(O)NR⁸—;

R⁶ and R⁷ are independently selected from:
H; $C_{1-4}$ alkyl, $C_{3-6}$ cycloalkyl, aryl, heterocycle, unsubstituted or substituted with one or two:
a) $C_{1-4}$ alkoxy,
b) halogen, or
c) substituted or unsubstituted aryl or substituted or unsubstituted heterocycle, R⁸ is independently selected from hydrogen, $C_1-C_6$ alkyl, benzyl, 2,2,2-trifluoroethyl and aryl;

R⁹ is independently selected from $C_1-C_6$ alkyl and aryl;

A¹ and A² are independently selected from: a bond, —CH=CH—, —C≡C—, —C(O)—, —C(O)NR⁸—, —NR⁸C(O)—, O, —N(R⁸)—, —S(O)₂N(R⁸)—, —N(R⁸)S(O)₂—, or —S(O)ₘ;

G and M are independently selected from: $CH_y$ or N;

V is selected from:
a) heterocycle selected from pyrrolidinyl, imidazolyl, pyridinyl, thiazolyl, indolyl, quinolinyl, isoquinolinyl, and thienyl, and
b) aryl;

W is a heterocycle selected from pyrrolidinyl, triazolyl, imnidazolyl, pyridinyl, thiazolyl, indolyl, quinolinyl, or isoquinolinyl;

X is a bond, —S(O)ₘ—, O or —C(=O)—;

Y is selected from: $CR^{2a}$, C=O, C=NH or N;

Z is selected from: $CR^{2a}$, C=O or N;

m is 0, 1 or 2;

n is 0, 1, 2, 3 or 4;

p is 1, 2 or 3;

q is 0, 1 or 2, provided that q is not 0 or 1 if X is O;

r is 0 to 5;

s is 1 or 2;

t is 1; and y is 1 or 2;

or an optical isomer or a pharmaceutically acceptable salt thereof.

5. The compound according to claim 2 which inhibits farnesyl-protein transferase of the formula B:

b) aryl, heterocycle, $C_3-C_{10}$ cycloalkyl, R⁸O—, —N(R⁸)₂, F or $C_2-C_6$ alkenyl,
c) unsubstituted or substituted $C_1-C_6$ alkyl wherein the substituent on the substituted $C_1-C_6$ alkyl is selected from unsubstituted or substituted aryl, heterocycle, $C_3-C_{10}$ cycloalkyl, $C_2-C_6$ alkenyl, R⁸O— and —N(R⁸)₂;

$R^{2a}$ and $R^{2b'}$ are independently selected from selected from: H; $C_1-C_6$ alkyl,

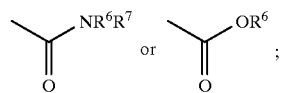

$R^{3a}$ and $R^{3b}$ are independently selected from:
a) hydrogen,
b) unsubstituted or substituted aryl, unsubstituted or substituted heterocycle, unsubstituted or substituted $C_3-C_{10}$ cycloalkyl, unsubstituted or substituted $C_2-C_6$ alkenyl, $C_2-C_6$ alkynyl, halogen, $C_1-C_6$ perfluoroalkyl, R⁹O—, R⁹S(O)ₘ—, R⁸C(O)NR⁸—, (R⁸)₂NC(O)—, R⁹C(O)O—, R⁸₂N—C(NR⁸)—, CN, NO₂, R⁸C(O)—, N₃, —N(R⁸)₂, or R⁹OC(O)NR⁸—,
c) unsubstituted $C_1-C_6$ alkyl,
d) substituted $C_1-C_6$ alkyl wherein the substituent on the substituted $C_1-C_6$ alkyl is selected from unsubstituted or substituted aryl, unsubstituted or substituted heterocyclic, $C_3-C_{10}$ cycloalkyl, $C_2-C_6$ alkenyl, $C_2-C_6$ alkynyl, R⁹O—, R⁹S(O)ₘ—, R⁸C(O)NR⁸—, (R⁸)₂NC(O)—, R⁸₂N—C(NR⁸)—, CN, R⁸C(O)—, N₃, —N(R⁸)₂, and R⁹OC(O)—NR⁸—;

R⁴ is independently selected from:
a) hydrogen,
b) aryl, substituted aryl, heterocycle, substituted heterocycle, $C_1-C_6$ alkyl, $C_2-C_6$ alkenyl, $C_2-C_6$ alkynyl, $C_1-C_6$ perfluoroalkyl, F, Cl, R⁸O—, R⁸C(O)NR⁸—, CN, NO₂, (R⁸)₂N—C(NR⁸)—, R⁸C(O)—, —N(R⁸)₂, or R⁹OC(O)NR⁸—, and
c) $C_1-C_6$ alkyl substituted by $C_1-C_6$ perfluoroalkyl, R⁸O—, R⁸C(O)NR⁸—, (R⁸)₂N—C(NR⁸)—, R⁸C(O)—, —N(R⁸)₂, or R⁹OC(O)NR⁸—;

$R^{5a}$ and $R_{5b}$ are independently hydrogen, $C_1-C_6$ alkyl, cyclopropyl, trifluoromethyl and halogen;

B

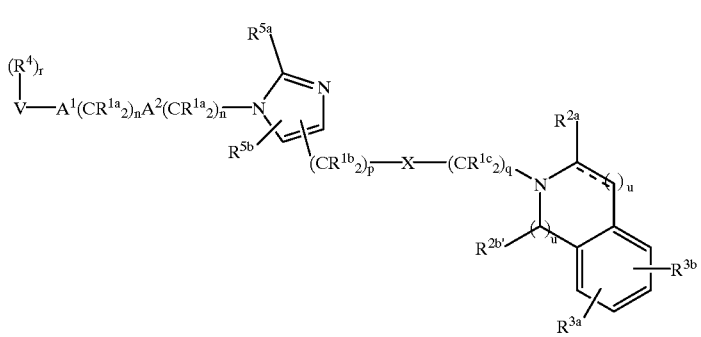

wherein:

$R^{1a}$ and $R^{1c}$ are independently selected from: hydrogen, $C_3-C_{10}$ cycloalkyl, R⁸O—, —N(R⁸)₂, F or $C_1-C_6$ alkyl;

$R^{1b}$ is independently selected from:
a) hydrogen,

R⁶ and R⁷ are independently selected from:
H; $C_{1-4}$ alkyl, $C_{3-6}$ cycloalkyl, aryl, heterocycle, unsubstituted or substituted with one or two:
a) $C_{1-4}$ alkoxy,
b) halogen, or
c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$A^1$ and $A^2$ are independently selected from: a bond, —CH=CH—, —C≡C—, —C(O)—, —C(O)NR$^8$—, O, —N($R^8$)—, or —S(O)$_m$;

V is selected from:
 a) heterocycle selected from pyrrolidinyl, imidazolinyl, pyridinyl, thiazolyl, oxazolyl, indolyl, quinolinyl, isoquinolinyl, triazolyl and thienyl,
 b) aryl,
 c) $C_1$–$C_{20}$ alkyl wherein from 1 to 4 carbon atoms are replaced with a heteroatom selected from O, S, and N, and
 d) $C_2$–$C_{20}$ alkenyl;

X is a bond, —S(O)$_m$—, O or —C(=O)—;

m is 0, 1 or 2;

n is 0, 1, 2, 3 or 4;

p is 0, 1, 2, 3 or 4;

q is 0, 1 or 2, provided that q is not 0 or 1 if X is O;

r is 0 to 5; and u is independently 0 or 1;

or an optical isomer or pharmaceutically acceptable salt thereof.

6. The compound according to claim 1 which inhibits farnesyl-protein transferase of the formula B1:

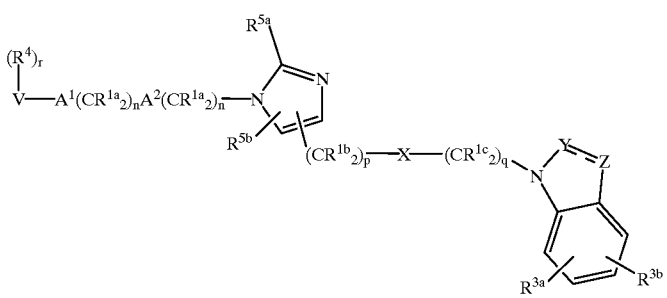

B1 wherein $R^{1a}$ and $R^{1c}$ are independently selected from: hydrogen, $C_3$–$C_{10}$ cycloalkyl, $R^8$O—, —N($R^8$)$_2$, F or $C_1$–$C_6$ alkyl;

$R^{1b}$ is independently selected from:
 a) hydrogen,
 b) aryl, heterocycle, $C_3$–$C_{10}$ cycloalkyl, $R^8$O—, —N($R^8$)$_2$, F or $C_2$–$C_6$ alkenyl,
 c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^8$— and —N($R^8$)$_2$;

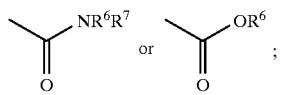

$R^{2a}$ is selected from selected from: H; $C_1$–$C_6$ alkyl, NH$_2$, $R^{3a}$ and $R^{3b}$ are independently selected from:

a) hydrogen,
b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9$O—, $R^9$S(O)$_m$—, $R^8$C(O)NR$^8$—, ($R^8$)$_2$NC(O)—, $R^9$C(O)O—, $R^8{}_2$N—C(NR$^8$)—, CN, NO$_2$, $R^8$C(O)—, N$_3$, —N($R^8$)$_2$, or $R^9$OC(O)NR$^8$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9$O—, $R^9$S(O)$_m$—, $R^8$C(O)NR$^8$—, ($R^8$)$_2$NC(O)—, $R^8{}_2$N—C(NR$^8$)—, CN, $R^8$C(O)—, N$_3$, —N($R^8$)$_2$, and $R^9$OC(O)—NR$^8$—;

$R^4$ is independently selected from:
 a) hydrogen,
 b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8$O—, $R^8$C(O)NR$^8$—, CN, NO$_2$, ($R^8$)$_2$N—C(NR$^8$)—, $R^8$C(O)—, —N($R^8$)$_2$, or $R^9$OC(O)NR$^8$—, and
 c) $C_1$–$C_6$ alkyl substituted by $C_1$–$C_6$ perfluoroalkyl, $R^8$O—, $R^8$C(O)NR$^8$—, ($R^8$)$_2$N—C(NR$^8$)—, $R^8$C(O)—, —N($R^8$)$_2$, or $R^9$OC(O)NR$^8$—;

$R^{5a}$ and $R^{5b}$ are independently hydrogen, $C_1$–$C_6$ alkyl, cyclopropyl, trifluoromethyl and halogen;

$R^6$ and $R^7$ are independently selected from:

H; $C_{1-4}$ alkyl, $C_{3-6}$ cycloalkyl, aryl, heterocycle, unsubstituted or substituted with one or two:
 a) $C_{1-4}$ alkoxy,
 b) halogen, or
 c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$A^1$ and $A^2$ are independently selected from: a bond, —CH=CH—, —C≡C—, —C(O)—, —C(O)NR$^8$—, O, —N($R^8$)—, or —S(O)$_m$;

V is selected from:
 a) heterocycle selected from pyrrolidinyl, imidazolinyl, pyridinyl, thiazolyl, oxazolyl, indolyl, quinolinyl, isoquinolinyl, triazolyl and thienyl,
 b) aryl,
 c) $C_1$–$C_{20}$ alkyl wherein from 1 to 4 carbon atoms are replaced with a heteroatom selected from O, S, and N, and
 d) $C_2$–$C_{20}$ alkenyl;

and provided that V is not imidazolyl;

X is a bond, —S(O)$_m$—, O or —C(=O)—;
Y is selected from: CR$^{2a}$, C=O, C=NH or N;
Z is selected from: CR$^{2a}$, C=O or N;
m is 0, 1 or 2;
n is 0, 1, 2, 3 or 4;
p is 1, 2 or 3;
q is 0, 1 or 2, provided that q is not 0 or 1 if X is O;
r is 0 to 5; and
y is 1 or 2;
or an optical isomer or pharmaceutically acceptable salt thereof.

7. The compound according to claim 2 which inhibits farnesyl-protein transferase of the formula C:

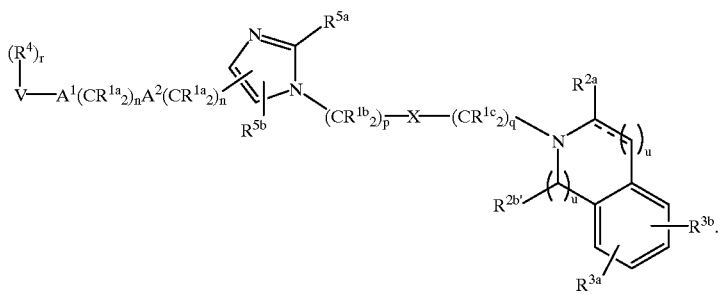

C wherein:
R$^{1a}$ and R$^{1c}$ are independently selected from: hydrogen, C$_3$–C$_{10}$ cycloalkyl, R$^8$O—, —N(R$^8$)$_2$, F or C$_1$–C$_6$ alkyl;

R$^{1b}$ is independently selected from:
a) hydrogen,
b) aryl, heterocycle, C$_3$–C$_{10}$ cycloalkyl, R$^8$O—, —N(R$^8$)$_2$, F or C$_2$–C$_6$ alkenyl,
c) unsubstituted or substituted C$_1$–C$_6$ alkyl wherein the substituent on the substituted C$_1$–C$_6$ alkyl is selected from unsubstituted or substituted aryl, heterocycle, C$_3$–C$_{10}$ cycloalkyl, C$_2$–C$_6$ alkenyl, R$^8$O— and —N(R$^8$)$_2$;

R$^{2a}$ and R$^{2b'}$ are independently selected from selected from: H; C$_1$–C$_6$ alkyl,

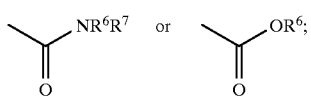

R$^{3a}$ and R$^{3b}$ are independently selected from:
a) hydrogen,
b) unsubstituted or substituted aryl, unsubstituted or substituted heterocycle, unsubstituted or substituted C$_3$–C$_{10}$ cycloalkyl, unsubstituted or substituted C$_2$–C$_6$ alkenyl, C$_2$–C$_6$ alkynyl, halogen, C$_1$–C$_6$ perfluoroalkyl, R$^9$O—, R$^9$S(O)$_m$—, R$^8$C(O)NR$^8$—, (R$^8$)$_2$NC(O)—, R$^9$C(O)O—, R$^8$$_2$N—C(NR$^8$)—, CN, NO$_2$, R$^8$C(O)—, N$_3$, —N(R$^8$)$_2$, or R$^9$OC(O)NR$^8$—,
c) unsubstituted C$_1$–C$_6$ alkyl,
d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^9$O—, R$^9$S(O)$_m$—, R$^8$C(O) NR$^8$—, (R$^8$)$_2$NC(O)—, R$^8$$_2$N—C(NR$^8$)—, CN, R$^8$C (O)—, N$_3$, —N(R$^8$)$_2$, and R$^9$OC(O)—NR$^8$—;

R$^4$ is independently selected from:
a) hydrogen,
b) aryl, substituted aryl, heterocycle, substituted heterocycle, C$_1$–C$_6$ alkyl, C$_2$–C$_6$ alkenyl, C$_2$–C$_6$ alkynyl, C$_1$–C$_6$ perfluoroalkyl, F, Cl, R$^8$O—, R$^8$C (O)NR$^8$—, CN, NO$_2$, (R$^8$)$_2$N—C(NR$^8$)—, R$^8$C (O)—, —N(R$^8$)$_2$, or R$^9$OC(O)NR$^8$—, and
c) C$_1$–C$_6$ alkyl substituted by C$_1$–C$_6$ perfluoroalkyl, R$^8$O—, R$^8$C(O)NR$^8$—, (R$^8$)$_2$N—C(NR$^8$)—, R$^8$C (O)—, —N(R$^8$)$_2$, or R$^9$OC(O)NR$^8$—;

R$^{5a}$ and R$^{5b}$ are independently hydrogen, C$_1$–C$_6$ alkyl, cyclopropyl, trifluoromethyl and halogen;

R$^6$ and R$^7$ are independently selected from:
H; C$_{1-4}$ alkyl, C$_{3-6}$ cycloalkyl, aryl, heterocycle, unsubstituted or substituted with one or two:
a) C$_{1-4}$ alkoxy,
b) halogen, or
c) substituted or unsubstituted aryl or substituted or unsubstituted heterocycle;

R$^8$ is independently selected from hydrogen, C$_1$–C$_6$ alkyl, 2,2,2-trifluoroethyl, benzyl and aryl;

R$^9$ is independently selected from C$_1$–C$_6$ alkyl and aryl;

A$^1$ and A$^2$ are independently selected from: a bond, —CH=CH—, —C≡C—, —C(O)—, —C(O)NR$^8$—, O, —N(R$^8$)—, or —S(O)$_m$;

V is selected from:
a) heterocycle selected from pyrrolidinyl, imidazolinyl, pyridinyl, thiazolyl, oxazolyl, indolyl, quinolinyl, isoquinolinyl, triazolyl and thienyl,
b) aryl,
c) C$_1$–C$_{20}$ alkyl wherein from 1 to 4 carbon atoms are replaced with a heteroatom selected from O, S, and N, and
d) C$_2$–C$_{20}$ alkenyl;

X is a bond, —S(O)$_m$—, O or —C(=O)—;
m is 0, 1 or 2;
n is 0, 1, 2, 3 or 4;
p is 0, 1, 2, 3 or 4, provided that p is not 0 if X is a bond or O;
q is 0, 1 or 2, provided that q is not 0 or 1 if X is O;
r is 0 to 5; and
u is independently 0 or 1;
or an optical isomer or a pharmaceutically acceptable salt thereof.

8. The compound according to claim 5 which inhibits farnesyl-protein transferase of the formula D:

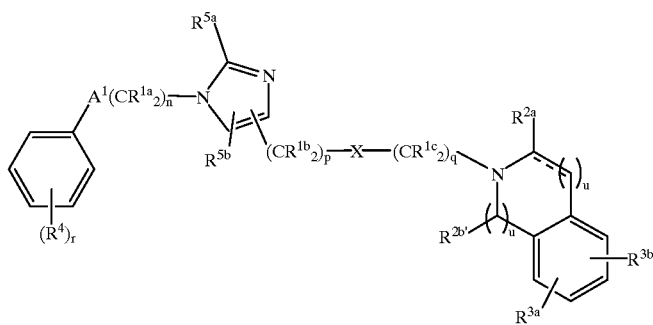

D wherein:

$R^{1a}$ and $R^{1c}$ are independently selected from: hydrogen, $C_3$–$C_{10}$ cycloalkyl or $C_1$–$C_6$ alkyl;

$R^{1b}$ is independently selected from:
  a) hydrogen,
  b) aryl, heterocycle, $C_3$–$C_{10}$ cycloalkyl, $R^8O$—, —$N(R^8)_2$, F or $C_2$–$C_6$ alkenyl,
  c) $C_1$–$C_6$ alkyl unsubstituted or substituted by aryl, heterocycle, $C_3$–$C_{10}$ cycloalkyl, $C_2$–$C_6$ alkenyl, $R^8O$—, or —$N(R^8)_2$;

$R^{2a}$ and $R^{2b'}$ are independently selected from selected from: H; $C_1$–$C_6$ alkyl,

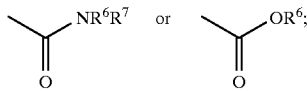

$R^{3a}$ and $R^{3b}$ are independently selected from:
  a) hydrogen,
  b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8{}_2N$—$C(NR^8)$—, CN, $NO_2$, $R^8C(O)$—, $N_3$, —$N(R^8)_2$, or $R^9OC(O)NR^8$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8{}_2N$—$C(NR^8)$—, CN, $R^8C(O)$—, $N_3$, —$N(R^8)_2$, and $R^9OC(O)$—$NR^8$—;

$R^4$ is independently selected from:
  a) hydrogen,
  b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, —$N(R^8)_2$, or $R^9OC(O)NR^8$—, and
  c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —$N(R^8)_2$, or $R^9OC(O)NR^8$—;

$R^{5a}$ and $R^{5b}$ are independently hydrogen, ethyl, cyclopropyl or methyl;

$R^6$ and $R^7$ are independently selected from:
  H; $C_{1-4}$ alkyl, $C_{3-6}$ cycloalkyl, aryl, heterocycle, unsubstituted or substituted with one or two:
    a) $C_{1-4}$ alkoxy,
    b) halogen, or
    c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$A^1$ is selected from: a bond, —C(O)—, O, —$N(R^8)$—, or —$S(O)_m$;

X is a bond, —$S(O)_m$—, O or —C(=O)—;

n is 0, 1 or 2; provided that n is not 0 or 1 if $A^1$ is a bond, O, —$N(R^8)$—, or $S(O)_m$;

m is 0, 1 or 2;

p is 0, 1, 2, 3 or 4;

q is 0, 1 or 2, provided that q is not 0 or 1 if X is O;

r is 1 or 2; and u is independently 0 or 1;

or an optical isomer or pharmaceutically acceptable salt thereof.

9. The compound according to claim 6 which inhibits farnesyl-protein transferase of the formula D1:

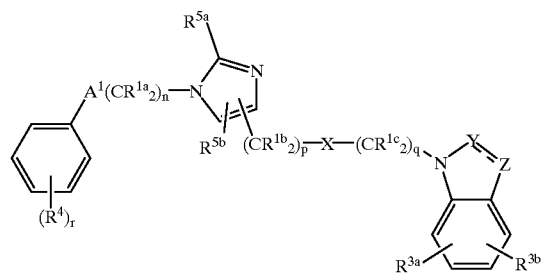

D1 wherein $R^{1a}$ and $R^{1c}$ are independently selected from: hydrogen, $C_3$–$C_{10}$ cycloalkyl or $C_1$–$C_6$ alkyl;

$R^{1b}$ is independently selected from:
  a) hydrogen,
  b) aryl, heterocycle, $C_3$–$C_{10}$ cycloalkyl, $R^8O$—, —$N(R^8)_2$, F or $C_2$–$C_6$ alkenyl,
  c) $C_1$–$C_6$ alkyl unsubstituted or substituted by aryl, heterocycle, $C_3$–$C_{10}$ cycloalkyl, $C_2$–$C_6$ alkenyl, $R^8O$—, or —$N(R^8)_2$;

$R^{2a}$ is selected from selected from: H; $C_1$–$C_6$ alkyl, $NH_2$,

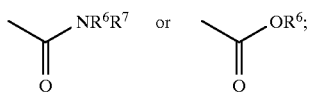

$R^{3a}$ and $R^{3b}$ are independently selected from:
 a) hydrogen,
 b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8{}_2N$—$C(NR^8)$—, CN, $NO_2$, $R^8C(O)$—, $N_3$, —$N(R^8)_2$, or $R^9OC(O)NR^8$—,
 c) unsubstituted $C_1$–$C_6$ alkyl,
 d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8{}_2N$—$C(NR^8)$—, CN, $R^8C(O)$—, $N_3$, —$N(R^8)_2$, and $R^9OC(O)$—$NR^8$—;

$R^4$ is independently selected from:
 a) hydrogen,
 b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, —$N(R^8)_2$, or $R^9OC(O)NR^8$—, and
 c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —$N(R^8)_2$, or $R^9OC(O)NR^8$—;

$R^{5a}$ and $R^{5b}$ are independently hydrogen, ethyl, cyclopropyl or methyl;

$R^6$ and $R^7$ are independently selected from:
 H; $C_{1-4}$ alkyl, $C_{3-6}$ cycloalkyl, aryl, heterocycle, unsubstituted or substituted with one or two:
  a) $C_{1-4}$ alkoxy,
  b) halogen, or
  c) substituted or unsubstituted aryl or substituted or unsubstituted heterocycle;

$R^8$ is independently selected from hydrogen, $C_{1-C6}$ alkyl, 2,2,2-trifluoroethyl, benzyl and aryl;

$R^9$ is independently selected from $C_1$–$C_6$ alkyl and aryl;

$A^1$ is selected from: a bond, —C(O)—, O, —$N(R^8)$—, or —$S(O)_m$;

X is a bond, —$S(O)_m$—, O or —C(=O)—;

Y is selected from: $CR^{2a}$, C=NH or N;

Z is selected from: $CR^{2a}$, or N; provided that at least Y or Z is N;

n is 0, 1 or 2; provided that n is not 0 or 1 if $A^1$ is a bond, O, —$N(R^8)$—, or $S(O)_m$;

m is 0, 1 or 2;

p is 0, 1, 2, 3 or 4;

q is 0, 1 or 2, provided that q is not 0 or 1 if X is O;

r is 1 or 2; and y is 1 or 2;

or an optical isomer or pharmaceutically acceptable salt thereof.

10. The compound according to claim 7 which inhibits farnesyl-protein transferase of the formula E:

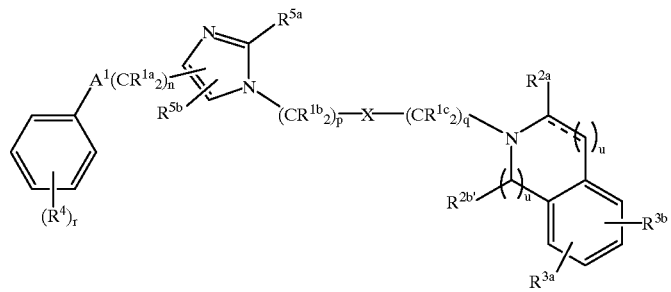

E wherein:
 $R^{1a}$ and $R^{1c}$ are independently selected from: hydrogen, $R^8O$—, —$N(R^8)_2$, F, $C_3$–$C_{10}$ cycloalkyl or $C_1$–$C_6$ alkyl;

$R^{1b}$ is independently selected from:
  a) hydrogen,
  b) aryl, heterocycle, $C_3$–$C_{10}$ cycloalkyl, $R^8O$—, —$N(R^8)_2$, F or $C_2$–$C_6$ alkenyl,
  c) $C_1$–$C_6$ alkyl unsubstituted or substituted by aryl, heterocycle, $C_3$–$C_{10}$ cycloalkyl, $C_2$–$C_6$ alkenyl, $R^8O$—, or —$N(R^8)_2$;

$R^{2a}$ and $R^{2b'}$ are independently selected from selected from: H; $C_1$–$C_6$ alkyl,

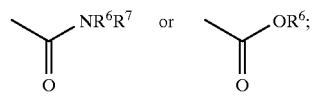

$R^{3a}$ and $R^{3b}$ are independently selected from:
  a) hydrogen,
  b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8{}_2N$—$C(NR^8)$—, CN, $NO_2$, $R^8C(O)$—, $N_3$, —$N(R^8)_2$, or $R^9OC(O)NR^8$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8{}_2N$—$C(NR^8)$—, CN, $R^8C(O)$—, $N_3$, —$N(R^8)_2$, and $R^9OC(O)$—$NR^8$—;

$R^4$ is independently selected from:
a) hydrogen,
b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, —$N(R^8)_2$, or $R^9OC(O)NR^8$—, and
c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —$N(R^8)_2$, or $R^9OC(O)NR^8$—;

$R^{5a}$ and $R^{5b}$ are independently hydrogen, ethyl, cyclopropyl or methyl;

$R^6$ and $R^7$ are independently selected from:
H; $C_{1-4}$ alkyl, $C_{3-6}$ cycloalkyl, aryl, heterocycle, unsubstituted or substituted with one or two:
a) $C_{1-4}$ alkoxy,
b) halogen, or
c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

X is a bond, —$S(O)_m$—, O or —$C(=O)$—;

n is 0 or 1;

m is 0, 1 or 2;

p is 0, 1, 2, 3 or 4, provided that p is not 0 if X is a bond or O;

q is 0, 1 or 2, provided that q is not 0 or 1 if X is O;

r is 1 or 2; and u is independently 0 or 1;

or an optical isomer or pharmaceutically acceptable salt thereof.

11. The compound according to claim 8 which inhibits farnesyl-protein transferase of the formula F:

$R^{2a}$ and $R^{2b'}$ are independently selected from selected from: H; $C_1$–$C_6$ alkyl, <chemical structures: >=NR^6R^7 or >=OR^6, with C=O>

$R^{3a}$ and $R^{3b}$ are independently selected from:
a) hydrogen,
b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8{}_2N$—$C(NR^8)$—, CN, $NO_2$, $R^8C(O)$—, $N_3$, —$N(R^8)_2$, or $R^9OC(O)NR^8$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8{}_2N$—$C(NR^8)$—, CN, $R^8C(O)$—, $N_3$, —$N(R^8)_2$, and $R^9OC(O)$—$NR^8$—;

$R^{5a}$ and $R^{5b}$ are independently hydrogen, ethyl, cyclopropyl or methyl;

$R^6$ and $R^7$ are independently selected from:
H; $C_{1-4}$ alkyl, $C_{3-6}$ cycloalkyl, aryl, heterocycle, unsubstituted or substituted with one or two:
a) $C_{1-4}$ alkoxy,
b) halogen, or
c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

X is a bond, —$S(O)_m$—, O or —$C(=O)$—;

m is 0, 1 or 2;

F

<chemical structure of formula F: imidazole ring with $R^{5a}$, $R^{5b}$ substituents, connected via $CR^{1a}{}_2$ to a phenyl bearing NC group, and via $(CR^{1b}{}_2)_p$—X—$(CR^{1c}{}_2)_q$ to a nitrogen-containing bicyclic system bearing $R^{2a}$, $R^{2b'}$, $R^{3a}$, $R^{3b}$> wherein:
$R^{1a}$ and $R^{1c}$ are independently selected from: hydrogen, $C_3$–$C_{10}$ cycloalkyl or $C_1$–$C_6$ alkyl;

$R^{1b}$ is independently selected from:
a) hydrogen,
b) aryl, heterocycle, $C_3$–$C_{10}$ cycloalkyl, $R^8O$—, —$N(R^8)_2$ or F,
c) $C_1$–$C_6$ alkyl unsubstituted or substituted by aryl, heterocycle, $C_3$–$C_{10}$ cycloalkyl, $R^8O$—, or —$N(R^8)_2$;

p is 0, 1, 2, 3 or 4;

q is 0, 1 or 2, provided that q is not 0 or 1 if X is O; and u is independently 0 or 1;

or an optical isomer or pharmaceutically acceptable salt thereof.

12. The compound according to claim 10 which inhibits farnesyl-protein transferase of the formula G:

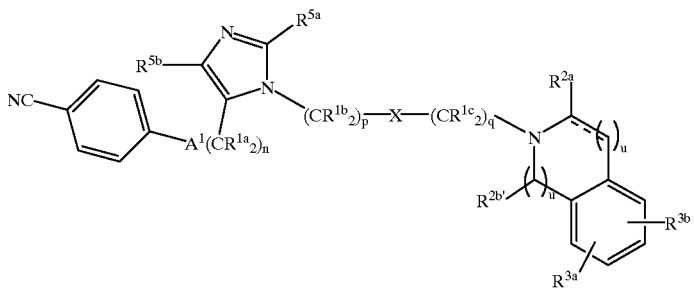

G wherein:

R$^{1a}$ and R$^{1c}$ are independently selected from: hydrogen, R$^8$O—, —N(R$^8$)$_2$, F, C$_3$–C$_{10}$ cycloalkyl or C$_1$–C$_6$ alkyl;

R$^{1b}$ is independently selected from:
a) hydrogen,
b) aryl, heterocycle or C$_3$–C$_{10}$ cycloalkyl,
c) C$_1$–C$_6$ alkyl unsubstituted or substituted by aryl, heterocycle, C$_3$–C$_{10}$ cycloalkyl, C$_2$–C$_6$ alkenyl, R$^8$O—, or —N(R$^8$)$_2$;

R$^{2a}$ and R$^{2b}$ are independently selected from selected from: H; C$_1$–C$_6$ alkyl,

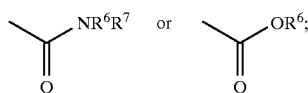

R$^{3a}$ and R$^{3b}$ are independently selected from:
a) hydrogen,
b) unsubstituted or substituted aryl, unsubstituted or substituted heterocycle, unsubstituted or substituted C$_3$–C$_{10}$ cycloalkyl, unsubstituted or substituted C$_2$–C$_6$ alkenyl, C$_2$–C$_6$ alkynyl, halogen, C$_1$–C$_6$ perfluoroalkyl, R$^9$O—, R$^9$S(O)$_m$—, R$^8$C(O)NR$^8$—, (R$^8$)$_2$NC(O)—, R$^9$C(O)O—, R$^8$$_2$N—C(NR$^8$)—, CN, NO$_2$, R$^8$C(O)—, N$_3$, —N(R$^8$)$_2$, or R$^9$OC(O)NR$^8$—,
c) unsubstituted C$_1$–C$_6$ alkyl,
d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^9$O—, R$^9$S(O)$_m$—, R$^8$C(O)NR$^8$—, (R$^8$)$_2$NC(O)—, R$^8$$_2$N—C(NR$^8$)—, CN, R$^8$C(O)—, N$_3$, —N(R$^8$)$_2$, and R$^9$OC(O)—NR$^8$—;

R$^{5a}$ and R$^{5b}$ are independently hydrogen, ethyl, cyclopropyl or methyl;

R$^6$ and R$^7$ are independently selected from:
H; C$_{1-4}$ alkyl, C$_{3-6}$ cycloalkyl, aryl, heterocycle, unsubstituted or substituted with one or two:
a) C$_{1-4}$ alkoxy,
b) halogen, or
c) substituted or unsubstituted aryl or substituted or unsubstituted heterocycle;

R$^8$ is independently selected from hydrogen, C$_1$–C$_6$ alkyl, 2,2,2-trifluoroethyl, benzyl and aryl;

R$^9$ is independently selected from C$_1$–C$_6$ alkyl and aryl;

A$^1$ is selected from: a bond, —C(O)—, O, —N(R$^8$)—, or —S(O)$_m$;

X is a bond, —S(O)m—, O or —C(=O)—;

m is 0, 1 or 2;

n is 0, 1 or 2; provided that n is not 0 if A$^1$ is a bond, O, —N(R$^8$)—, or S(O)$_m$;

p is 1, 2 or 3;

q is 0, 1 or 2, provided that q is not 0 or 1 if X is O; and u is independently 0 or 1;

or an optical isomer or pharmaceutically acceptable salt thereof.

13. A compound which inhibits farnesyl-protein transferase which is:

7-Bromo-2-(1-(4-cyanobenzyl)-5-imidazolylmethyl)-1,2,3,4-tetrahydroisoquinoline 2-(1-(4-Cyanobenzyl)-5-imidazolylmethyl)-1,2,3,4-tetrahydroisoquinoline 5,7-Dichloro-2-(1-(4-cyanobenzyl)-5-imidazolylmethyl)-1,2,3,4-tetrahydroisoquinoline 3(S)-Carboethoxy-2-(1-(4-cyanobenzyl)-5-imidazolylmethyl)-1,2,3,4-tetrahydroisoquinoline 3(R)-Carboethoxy-2-(1-(4-cyanobenzyl)-5-imidazolylmethyl)-1,2,3,4-tetrahydroisoquinoline 7-Nitro-2-(1-(4-cyanobenzyl)-5-imidazolylmethyl)-1,2,3,4-tetrahydroisoquinoline 7-Amino-2-(1-(4-cyanobenzyl)-5-imidazolylmethyl)-1,2,3,4-tetrahydroisoquinoline tris 7-Acetamido-2-(1-(4-cyanobenzyl)-5-imidazolylmethyl)-1,2,3,4-tetrahydroisoquinoline 7-Iodo-2-(1-(4-cyanobenzyl)-5-imidazolylmethyl)-1,2,3,4-tetrahydroisoquinoline 5-Bromo-2-(1-(4-cyanobenzyl)-5-imidazolylmethyl)-1,2,3,4-tetrahydroisoquinoline 5-(2,4-Dichlorophenyl)-2-(1-(4-cyanobenzyl)-5-imidazolylmethyl)-1,2,3,4-tetrahydroisoquinoline 5-(4-Cyanobenzyl)-2-(1-(4-cyanobenzyl)-5-imidazolylmethyl)-1,2,3,4-tetrahydroisoquinoline 5-(2-(3-Tolyl)vinyl)-2-(1-(4-cyanobenzyl)-5-imidazolylmethyl)-1,2,3,4-tetrahydroisoquinoline 5-(2-(3-Tolyl)ethyl)-2-(1-(4-cyanobenzyl)-5-imidazolylmethyl)-1,2,3,4-tetrahydroisoquinoline 7-Phenyl-2-(1-(4-cyanobenzyl)-5-imidazolylmethyl)-1,2,3,4-tetrahydroisoquinoline 7-(2-Tolyl)-2-(1-(4-cyanobenzyl)-5-imidazolylmethyl)-1,2,3,4-tetrahydroisoquinoline N-(2,3-Dimethylphenyl)-2-(1-(4-cyanobenzyl)-5-imidazolylmethyl)-1,2,3,4-tetrahydroisoquinoline-3 (S)-carboxamide N-(3-Chlorobenzyl) 2-(1-(4-cyanobenzyl)-5-imidazolylmethyl)-1,2,3,4-tetrahydroisoquinoline-3 (S)-carboxamide N-(3-Chlorobenzyl),N-methyl 2-(1-(4-cyanobenzyl)-5-imidazolylmethyl)-1,2,3,4-tetrahydroisoquinoline-3(S)-carboxamide N-(2,3-Dimethylphenyl)-2-(1-(4-cyanobenzyl)-5-imidazolylmethyl)-1,2,3,4-tetrahydroisoquinoline-3(R)-carboxamide 3(S)-Carboethoxy-7-phenyl-2-(1-(4-cyanobenzyl)-5-imidazolylmethyl)-1,2,3,4-tetrahydroisoquinoline 3(S)-Carboxylic acid-7-phenyl-2-(1-(4-cyanobenzyl)-5-imidazolylmethyl)-1,2,3,4-tetrahydroisoquinoline N-(3-chlorobenzyl) 7-phenyl-2-(1-(4-cyanobenzyl)-5-imidazolylmethyl)-1,2,3,4-tetrahydroisoquinoline-3(s)-carboxamide 3(S)-Hydroxymethyl-7-phenyl-2-(1-(4-cyanobenzyl)-5-imidazolylmethyl)-1,2,3,4-tetrahydroisoquinoline 1(R,S)-n-Butyl-7-bromo-2-(1-(4-cyanobenzyl)-5-imidazolylmethyl)-1,2,3,4-tetrahydroisoquinoline 1-(1-(4-Cyanobenzyl)-5-imidazolylmethyl)indole 5-Bromo-1-(1-(4-cyanobenzyl)-5-imidazolylmethyl)indole 4-Bromo-1-(1-(4-cyanobenzyl)-5-imidazolylmethyl)indole 4-Phenyl-1-(1-(4-cyanobenzyl)-5-imidazolylmethyl)indole 4-(2-Methylphenyl)-1-(1-(4-cyanobenzyl)-5-imidazolylmethyl)indole 6-Bromo-2-(1-(4-cyanobenzyl)-5-imidazolylmethyl)-3,4-dihydro-1(H)-isoquinolinone 6-Bromo-2-(1-(4-cyanobenzyl)-5-imidazolylmethyl)-1,2,3,4-tetrahydroisoquinoline 7-Bromo-2-(1-(4-cyanobenzyl)-5-imidazolylacetyl)-1,2,3,4-tetrahydroisoquinoline 5-Chloro-2-carboethoxy-1-(1-(4-cyanobenzyl)-5-imidazolylmethyl)indole 1-(4-cyanobenzyl)-5-(1-indolinylmethyl)imidazole 1-(4-cyanobenzyl)-5-(1-indazolylmethyl)imidazole 1-(4-cyanobenzyl)-5-(1-tetrahydroquinolinylmethyl)imidazole 5-(1-benzotriazolylmethyl)-1-(4-cyanobenzyl)imidazole 5-(1-benzoimidazolylmethyl)-1-(4-cyanobenzyl)imidazole 5-[1-(7-azaindolyl)methyl]-1-(4-cyanobenzyl)imidazole 5-[1-(4-azabenzimidazolyl)methyl]-1-(4-cyanobenzyl)imidazole 1-(4-cyanobenzyl)-5-(2-tetrahydroisoquinolinylmethyl)imidazole 5-(2-benzotriazolylmethyl)-1-(4-cyanobenzyl)imidazole 1-(4-cyanobenzyl)-5-(1-isatinylmethyl)imidazole 5-[1-(5-azabenzimidazolyl)methyl]-1-(4-cyanobenzyl)imidazole 5-[3-(5-azabenzimidazolyl)methyl]-1-(4-cyanobenzyl)imidazole 4-{5-[4-(3-Bromophenyl)-4,5,6,7-tetrahydroimidazo[4,5-c]pyridin-1-ylmethyl]imidazol-1-ylmethyl}benzonitrile 6,7-Dimethoxy-2-(1-(4-cyanobenzyl)-5-imidazolylmethyl)1,2,3,4-tetrahydroisoquinoline 1(R,S)-(2-Phenethyl)-6-methoxy-2-(1-(4-cyanobenzyl)-5-imidazolylmethyl)-1,2,3,4-tetrahydroisoquinoline 1-(4-Cyanobenzyl)-5-(2-amino-1-benzimidazolylmethyl)imidazole 1-(4'-cyanobenzyl)-5-(2-amino-1-(3-benzyl-2-imino-1-benzimidazolylmethyl)imidazole or an optical isomer or a pharmaceutically acceptable salt thereof.

14. The compound according to claim 13 which is:

3(R)-Carboethoxy-2-(1-(4-cyanobenzyl)-5-imidazolylmethyl)-1,2,3,4-tetrahydroisoquinoline

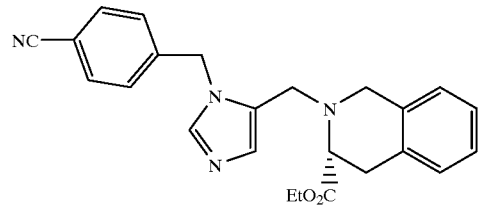

or an optical isomer or a pharmaceutically acceptable salt thereof.

15. The compound according to claim 13 which is:

7-Phenyl-2-(1-(4-cyanobenzyl)-5-imidazolylmethyl)-1,2,3,4-tetrahydroisoquinoline

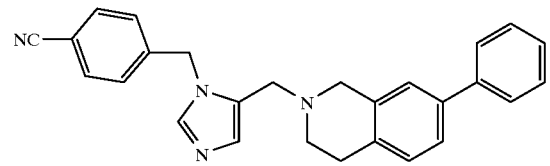

or a pharmaceutically acceptable salt thereof.

16. The compound according to claim 13 which is:

N-(3-Chlorobenzyl) 2-(1-(4-cyanobenzyl)-5-imidazolylmethyl)-1,2,3,4-tetrahydroisoquinoline-3(S)-carboxamide

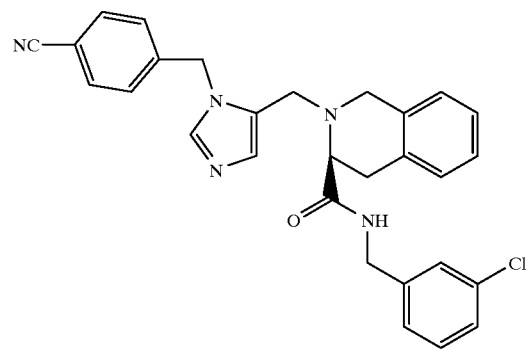

or an optical isomer or a pharmaceutically acceptable salt thereof.

17. The compound according to claim 13 which is:

1(R,S)-n-Butyl-7-bromo-2-(1-(4-cyanobenzyl)-5-imidazolylmethyl)-1,2,3,4-tetrahydroisoquinoline

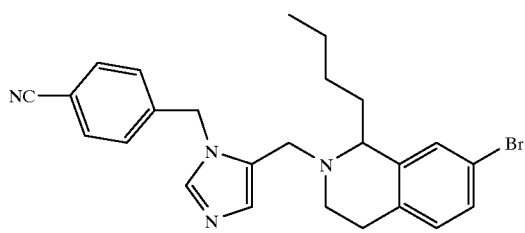

or an optical isomer or a pharmaceutically acceptable salt thereof.

18. The compound according to claim 13 which is:

1-(1-(4-Cyanobenzyl)-5-imidazolylmethyl)indole

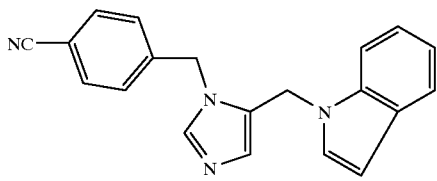

or an optical isomer or a pharmaceutically acceptable salt thereof.

19. The compound according to claim 13 which is:

1-(4-cyanobenzyl)-5-(1-indolinylmethyl)imidazole

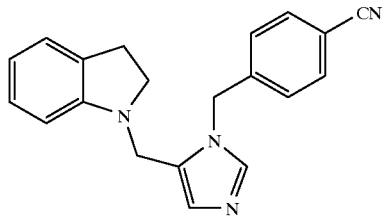

or an optical isomer or a pharmaceutically acceptable salt thereof.

20. The compound according to claim 13 which is:

1-(4-cyanobenzyl)-5-(1-indazolylmethyl)imidazole

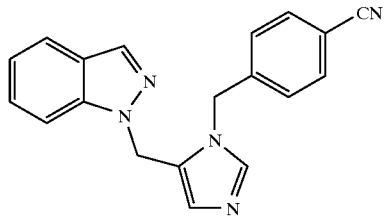

or an optical isomer or a pharmaceutically acceptable salt thereof.

21. The compound according to claim 13 which is:

1-(4-cyanobenzyl)-5-(1-tetrahydroquinolinylmethyl) imidazole

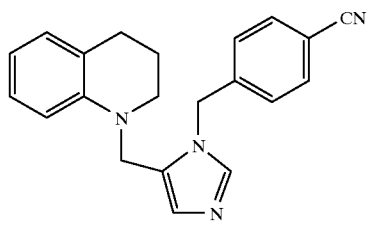

or an optical isomer or a pharmaceutically acceptable salt thereof.

22. The compound according to claim 13 which is:

5-(1-benzoimidazolylmethyl)-1-(4-cyanobenzyl) imidazole

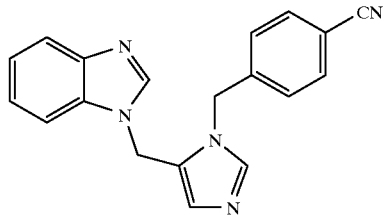

or an optical isomer or a pharmaceutically acceptable salt thereof.

23. The compound according to claim 13 which is:

1-(4-cyanobenzyl)-5-(2-tetrahydroisoquinolinylmethyl) imidazole

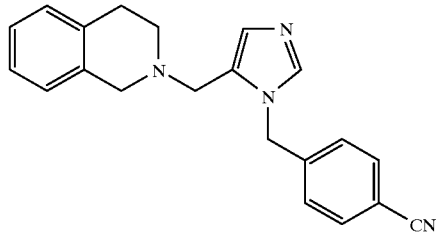

or an optical isomer or a pharmaceutically acceptable salt thereof.

24. The compound according to claim 13 which is:

6,7-Dimethoxy-2-(1-(4-cyanobenzyl)-5-imidazolylmethyl)1,2,3,4-tetrahydroisoquinoline

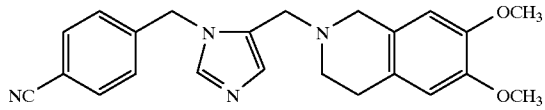

or an optical isomer or a pharmaceutically acceptable salt thereof.

25. The compound according to claim 13 which is:

1-(4'-cyanobenzyl)-5-(2-amino-1-(3-benzyl-2-imino-1-benzimidazolylmethyl)imidazole

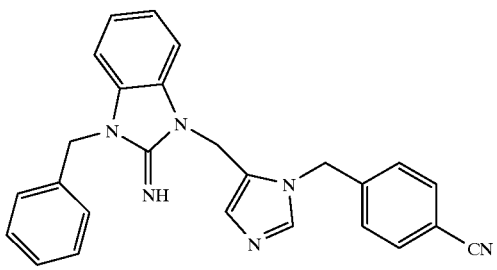

or an optical isomer or a pharmaceutically acceptable salt thereof.

26. A pharmaceutical composition comprising a pharmaceutical carrier, and dispersed therein, a therapeutically effective amount of a compound of claim 1.

27. A pharmaceutical composition comprising a pharmaceutical carrier, and dispersed therein, a therapeutically effective amount of a compound of claim 2.

28. A pharmaceutical composition comprising a pharmaceutical carrier, and dispersed therein, a therapeutically effective amount of a compound of claim 5.

29. A pharmaceutical composition comprising a pharmaceutical carrier, and dispersed therein, a therapeutically effective amount of a compound of claim 7.

30. A pharmaceutical composition comprising a pharmaceutical carrier, and dispersed therein, a therapeutically effective amount of a compound of claim 13.

31. A method for inhibiting farnesyl-protein transferase which comprises administering to a mammal in need thereof a therapeutically effective amount of a composition of claim 26.

32. A method for inhibiting farnesyl-protein transferase which comprises administering to a mammal in need thereof a therapeutically effective amount of a composition of claim 27.

33. A method for inhibiting farnesyl-protein transferase which comprises administering to a mammal in need thereof a therapeutically effective amount of a composition of claim 28.

34. A method for inhibiting farnesyl-protein transferase which comprises administering to a mammal in need thereof a therapeutically effective amount of a composition of claim 29.

35. A method for inhibiting farnesyl-protein transferase which comprises administering to a mammal in need thereof a therapeutically effective amount of a composition of claim 30.

36. A method for treating cancer which comprises administering to a mammal in need thereof a therapeutically effective amount of a composition of claim 26.

37. A method for treating cancer which comprises administering to a mammal in need thereof a therapeutically effective amount of a composition of claim 27.

38. A method for treating cancer which comprises administering to a mammal in need thereof a therapeutically effective amount of a composition of claim 28.

39. A method for treating cancer which comprises administering to a mammal in need thereof a therapeutically effective amount of a composition of claim 29.

40. A method for treating cancer which comprises administering to a mammal in need thereof a therapeutically effective amount of a composition of claim 30.

41. A method for treating neurofibromin benign proliferative disorder which comprises administering to a mammal in need thereof a therapeutically effective amount of a composition of claim 27.

42. A method for treating blindness related to retinal visualization which comprises administering to a mammal in need thereof a therapeutically effective amount of a composition of claim 27.

43. A method for treating infections from hepatitis delta and related viruses which comprises administering to a mammal in need thereof a therapeutically effective amount of a composition of claim 27.

44. A method for preventing restenosis which comprises administering to a mammal in need thereof a therapeutically effective amount of a composition of claim 27.

45. A method for treating polycystic kidney disease which comprises administering to a mammal in need thereof a therapeutically effective amount of a composition of claim 27.

46. A pharmaceutical composition made by combining the compound of claim 1 and a pharmaceutically acceptable carrier.

47. A pharmaceutical composition made by combining the compound of claim 2 and a pharmaceutically acceptable carrier.

48. A process for preparing a pharmaceutical composition comprising combining a compound of claim 1 and a pharmaceutically acceptable carrier.

49. A process for preparing a pharmaceutical composition comprising combining a compound of claim 2 and a pharmaceutically acceptable carrier.

* * * * *

UNITED STATES PATENT AND TRADEMARK OFFICE
CERTIFICATE OF CORRECTION

PATENT NO. : 5,977,134
DATED : November 2, 1999
INVENTOR(S) : Terrence M. Ciccarone, Wasyl Halczenko, John H. Hutchinson, William C. Lumma, Jr., Gerald E. Stokker, Craig A. Stump and Theresa M. Williams It is certified that error appears in the above-identified patent and that said Letters Patent is hereby corrected as shown below:

Column 91; claim 1,
Lines 56-61, the structure should read:

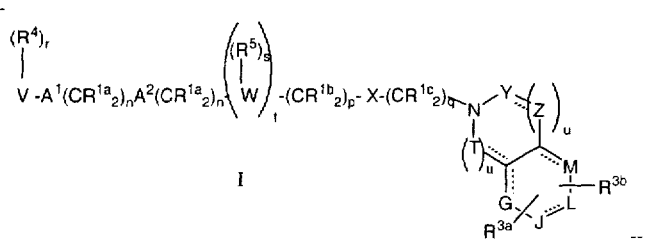

I

Column 92,
Lines 54-61, the structure should read :

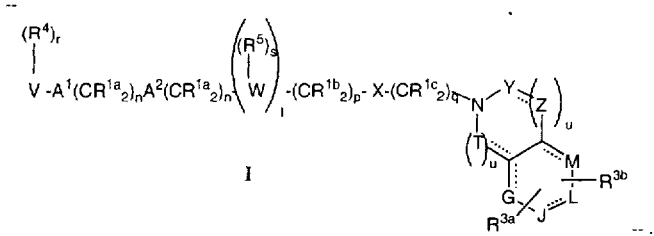

I

Column 95, claim 2,
Lines 33-48, the structure should read :

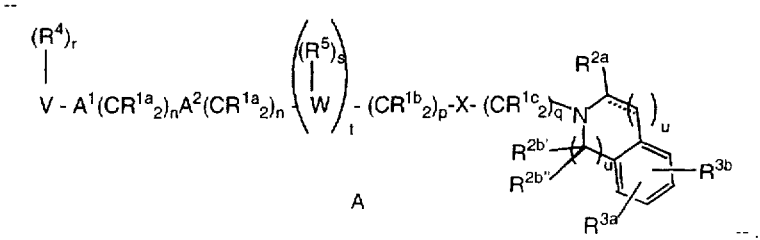

A

UNITED STATES PATENT AND TRADEMARK OFFICE
CERTIFICATE OF CORRECTION

PATENT NO. : 5,977,134                                   Page 2 of 3
DATED      : November 2, 1999
INVENTOR(S): Terrence M. Ciccarone, Wasyl Halczenko, John H. Hutchinson, William C. Lumma, Jr., Gerald E. Stokker, Craig A. Stump and Theresa M. Williams It is certified that error appears in the above-identified patent and that said Letters Patent is hereby corrected as shown below:

Column 91, claim 1,
Lines 56-61, the structure should read:

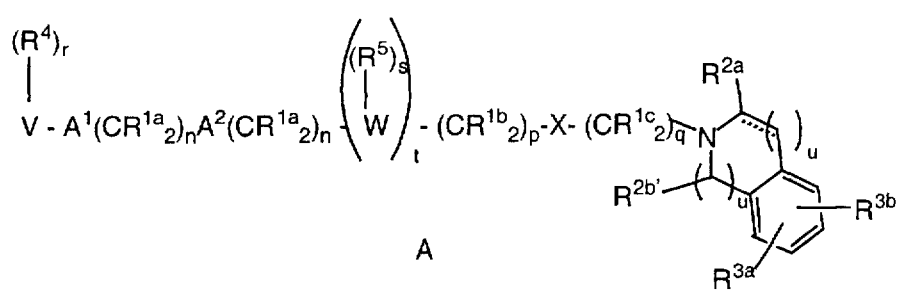

Column 92,
Lines 54-61, the structure should read:

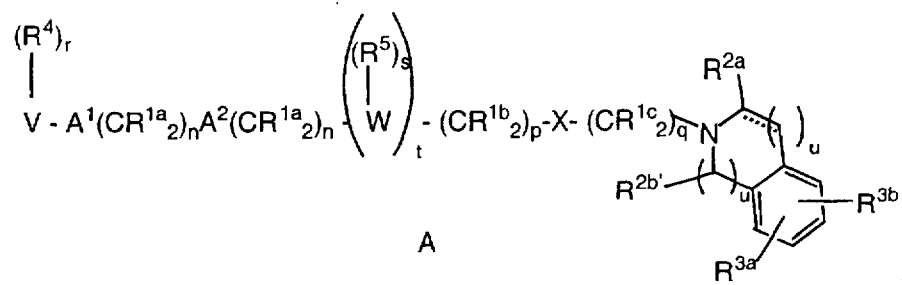

Column 94, claim 1,
Line 66, should read -- T is selected from: N, $CR^{2b'}$ or $CR^{2b'}R^{2b''}$; -- .

Column 95, claim 1,
Line 3, should read -- c) $C_1$-$C_{20}$ alkyl wherein from 1 to 4 carbon atoms are --.

Column 98, claim 3,
Lines 39-46, should read -- $R^{2a}$ and $R^{2b'}$ are independently selected from: H; $C_1$-$C_6$ alkyl,

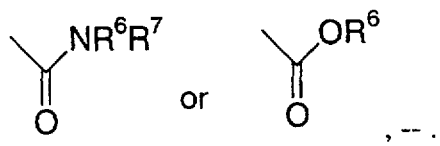

, -- .

UNITED STATES PATENT AND TRADEMARK OFFICE
CERTIFICATE OF CORRECTION

PATENT NO. : 5,977,134
DATED : November 2, 1999
INVENTOR(S) : Terrence M. Ciccarone, Wasyl Halczenko, John H. Hutchinson, William C. Lumma, Jr., Gerald E. Stokker, Craig A. Stump and Theresa M. Williams It is certified that error appears in the above-identified patent and that said Letters Patent is hereby corrected as shown below:

Column 100, claim 4,
Lines 14-19, the structure should be:

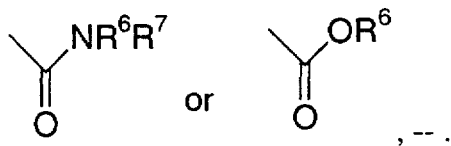

, -- .

Column 104, claim 6,
Line 63, should read -- $C_1$-$C_{20}$ alkyl wherein from 1 to 4 carbon atoms are -- .

Column 114, claim 13,
Lines 42-44, should read:
-- 7-Amino-2-(1-(4-cyanobenzyl)-5-imidazolylmethyl)-1,2,3,4-tetrahydroisoquinoline tris
7-Acetamido-2-(1-(4-cyanobenzyl)-5-imidazolylmethyl)-1,2,3,4-tetrahydroisoquinoline --.

Signed and Sealed this

Ninth Day of April, 2002

*Attest:*

*Attesting Officer*

JAMES E. ROGAN
*Director of the United States Patent and Trademark Office*